United States Patent
Eigler et al.

(10) Patent No.: US 7,509,169 B2
(45) Date of Patent: Mar. 24, 2009

(54) IMPLANTABLE PRESSURE TRANSDUCER SYSTEM OPTIMIZED FOR ANCHORING AND POSITIONING

(75) Inventors: Neal L. Eigler, Pacific Palisades, CA (US); Brian M. Mann, Marina Del Rey, CA (US); James S. Whiting, Los Angeles, CA (US); Werner Hafelfinger, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 374 days.

(21) Appl. No.: 11/115,991

(22) Filed: Apr. 27, 2005

(65) Prior Publication Data

US 2005/0288722 A1 Dec. 29, 2005

Related U.S. Application Data

(63) Continuation of application No. 11/111,691, filed on Apr. 21, 2005, and a continuation-in-part of application No. 10/672,443, filed on Sep. 26, 2003, now Pat. No. 7,149,587.

(60) Provisional application No. 60/564,315, filed on Apr. 22, 2004, provisional application No. 60/413,758, filed on Sep. 26, 2002.

(51) Int. Cl.
 *A61N 1/00* (2006.01)
(52) U.S. Cl. ....................................... 607/27
(58) Field of Classification Search ......... 607/126–128, 607/130–132, 119, 120, 122; 600/375
See application file for complete search history.

(56) References Cited

U.S. PATENT DOCUMENTS

| | | | |
|---|---|---|---|
| 3,397,699 A * | 8/1968 | Kohl | 604/105 |
| 3,672,352 A | 6/1972 | Summers | |
| 4,144,890 A * | 3/1979 | Hess | 607/130 |
| 4,679,144 A | 7/1987 | Cox et al. | |
| H356 H * | 11/1987 | Stokes et al. | 607/126 |
| 4,899,751 A | 2/1990 | Cohen | |
| 4,899,752 A | 2/1990 | Cohen | |
| 4,899,758 A | 2/1990 | Finkelstein et al. | |
| 4,967,749 A | 11/1990 | Cohen | |
| 4,972,847 A * | 11/1990 | Dutcher et al. | 607/131 |

(Continued)

FOREIGN PATENT DOCUMENTS

EP 0 472 411 A1 2/1992

(Continued)

OTHER PUBLICATIONS

Steinhaus, David M., et al., "*Initial Experience with an Implantable Hemodynamic Monitor*," Circulation, vol. 93, No. 4, pp. 745-752, Feb. 15, 1996.

(Continued)

*Primary Examiner*—George Manuel
(74) *Attorney, Agent, or Firm*—Knobbe, Martens, Olson & Bear, LLP

(57) ABSTRACT

This invention relates generally to systems and methods for optimizing the performance and minimizing complications related to implanted sensors, such as pressure sensors, for the purposes of detecting, diagnosing and treating cardiovascular disease in a medical patient. Systems and methods for anchoring implanted sensors to various body structures is also provided.

30 Claims, 18 Drawing Sheets

U.S. PATENT DOCUMENTS

| | | |
|---|---|---|
| 5,103,828 A | 4/1992 | Sramek |
| 5,163,429 A | 11/1992 | Cohen |
| 5,190,528 A | 3/1993 | Fonger et al. |
| 5,314,418 A | 5/1994 | Takano et al. |
| 5,324,325 A * | 6/1994 | Moaddeb .................. 607/120 |
| 5,324,327 A | 6/1994 | Cohen |
| 5,344,439 A * | 9/1994 | Otten ........................ 607/126 |
| 5,368,040 A | 11/1994 | Carney |
| 5,398,692 A | 3/1995 | Hickey |
| 5,464,434 A | 11/1995 | Alt |
| 5,498,524 A | 3/1996 | Hall |
| 5,535,752 A | 7/1996 | Halperin et al. |
| 5,743,267 A | 4/1998 | Nikolic et al. |
| 5,749,909 A | 5/1998 | Schroeppel et al. |
| 5,752,976 A | 5/1998 | Duffin et al. |
| 5,758,652 A | 6/1998 | Nikolic |
| 5,776,178 A * | 7/1998 | Pohndorf et al. ............ 607/127 |
| 5,861,003 A | 1/1999 | Latson et al. |
| 5,861,018 A | 1/1999 | Fierbach |
| 5,904,708 A | 5/1999 | Goedeke |
| 5,919,210 A | 7/1999 | Lurie et al. |
| 5,921,935 A | 7/1999 | Hickey |
| 5,976,174 A | 11/1999 | Ruiz |
| 6,024,756 A | 2/2000 | Huebsch et al. |
| 6,178,349 B1 | 1/2001 | Kieval |
| 6,223,081 B1 | 4/2001 | Kerver |
| 6,223,087 B1 | 4/2001 | Williams |
| 6,234,973 B1 | 5/2001 | Meador et al. |
| 6,240,321 B1 * | 5/2001 | Janke et al. ................ 607/122 |
| 6,309,350 B1 * | 10/2001 | VanTassel et al. ........... 600/300 |
| 6,328,699 B1 | 12/2001 | Eigler et al. |
| 6,553,263 B1 | 4/2003 | Meadows et al. |
| 6,623,521 B2 * | 9/2003 | Steinke et al. .............. 623/1.16 |
| 6,629,951 B2 | 10/2003 | Laufer et al. |
| 6,760,628 B2 | 7/2004 | Weiner et al. |
| 6,890,546 B2 * | 5/2005 | Mollison et al. ............ 424/430 |
| 6,939,376 B2 * | 9/2005 | Shulze et al. .............. 623/1.42 |
| 6,994,717 B2 * | 2/2006 | Konya et al. ................ 606/200 |
| 2002/0077555 A1 | 6/2002 | Schwartz |
| 2003/0055344 A1 | 3/2003 | Eigler et al. |
| 2004/0148003 A1 * | 7/2004 | Udipi et al. ................ 623/1.11 |

FOREIGN PATENT DOCUMENTS

| | | |
|---|---|---|
| EP | 1 050 265 A2 | 11/2000 |
| EP | 1 057 448 A1 | 12/2000 |
| WO | WO 96/11722 | 4/1996 |
| WO | WO 99/56812 | 11/1999 |

OTHER PUBLICATIONS

Soufer, Robert, "*Treating a Sick Heart*," Heart Disease, Nova Online web page, © 1997, WGBH.

Neergaard, Lauran, "*Daily Monitoring, Thanks to the Internet*," CHealth web page, Feb. 22, 2000, © 2000, HEALTHBEAT.

* cited by examiner

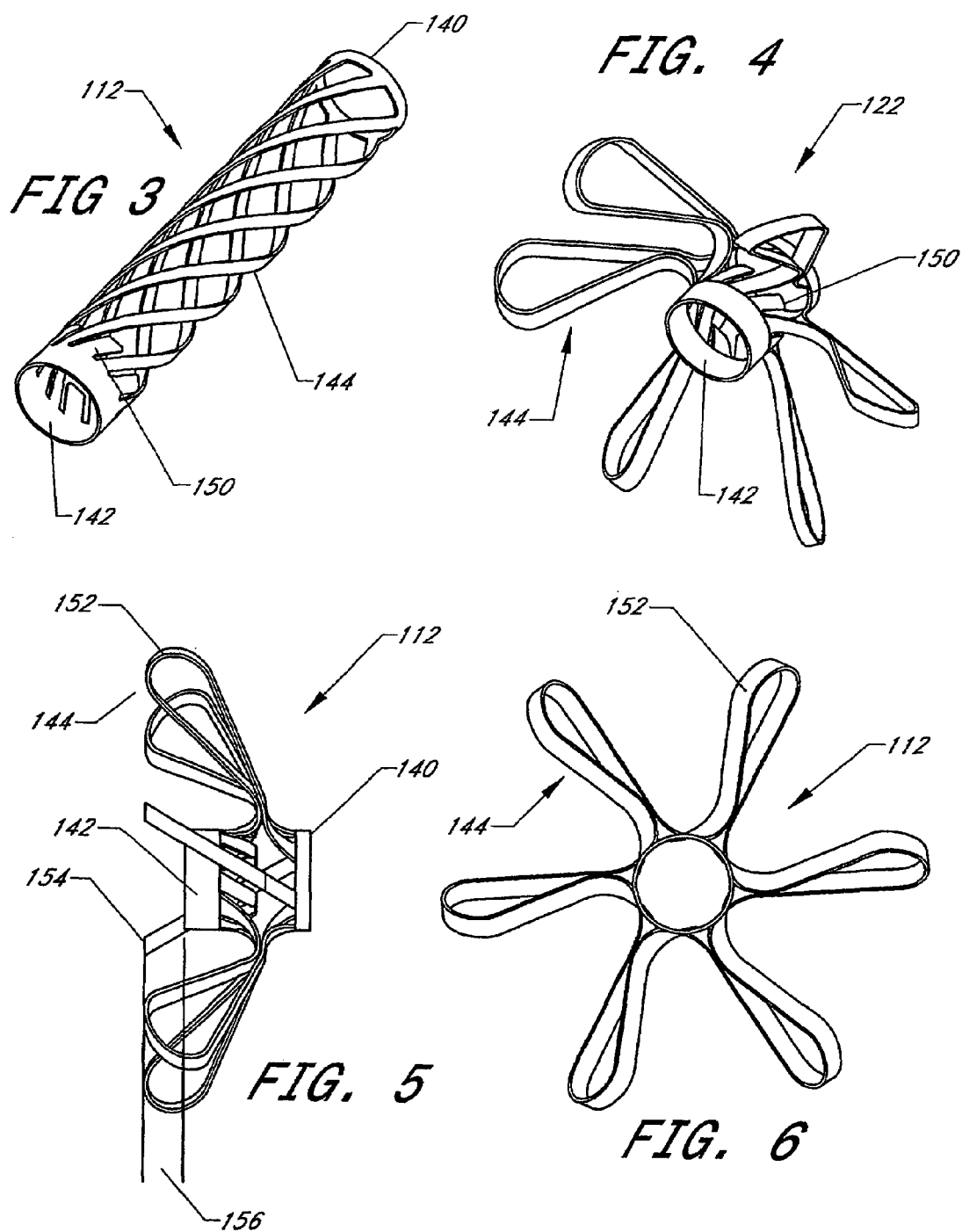

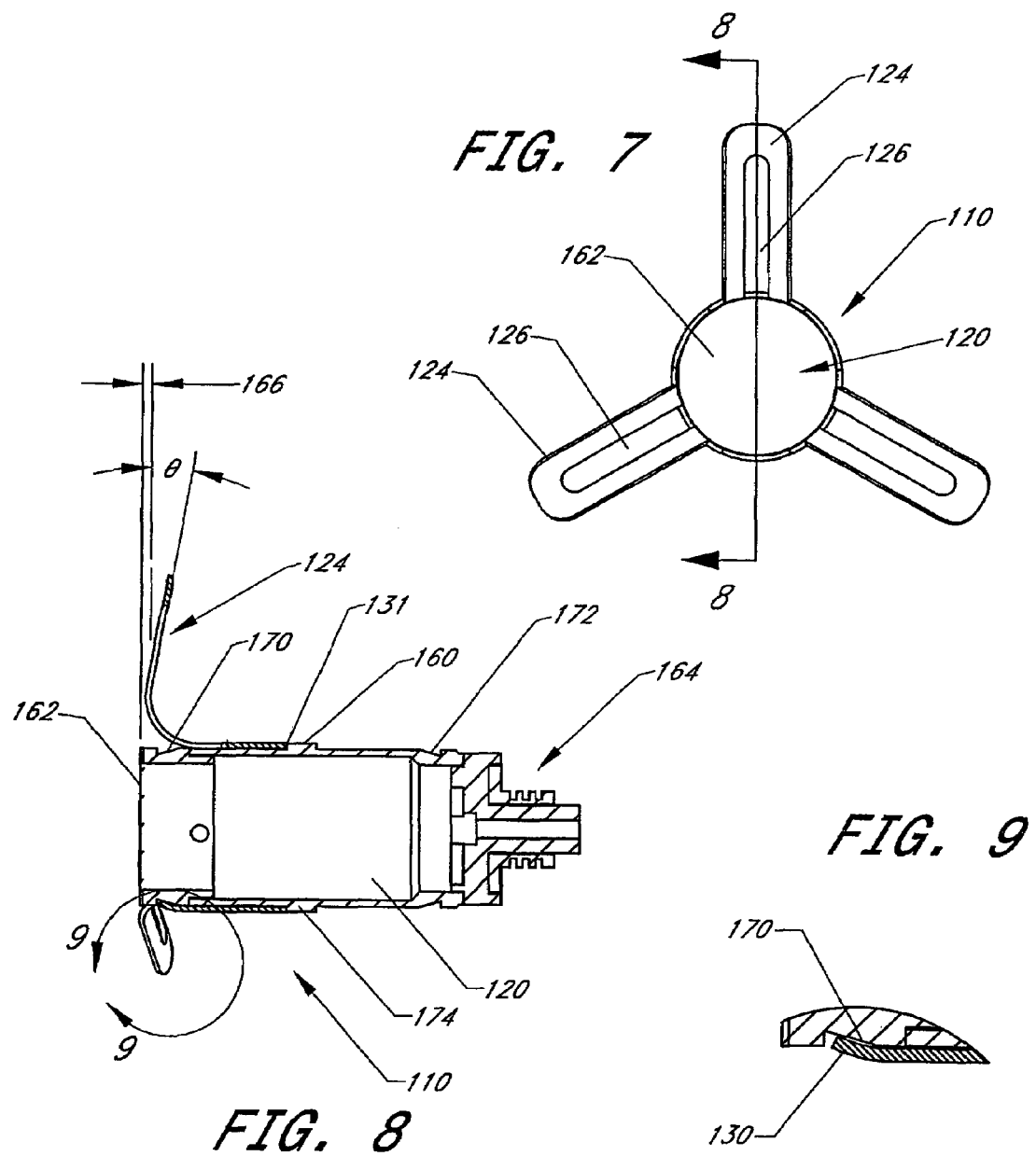

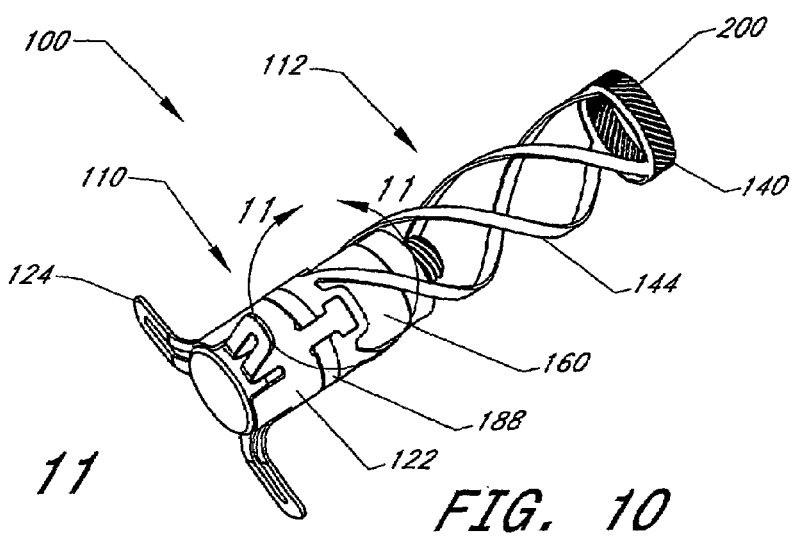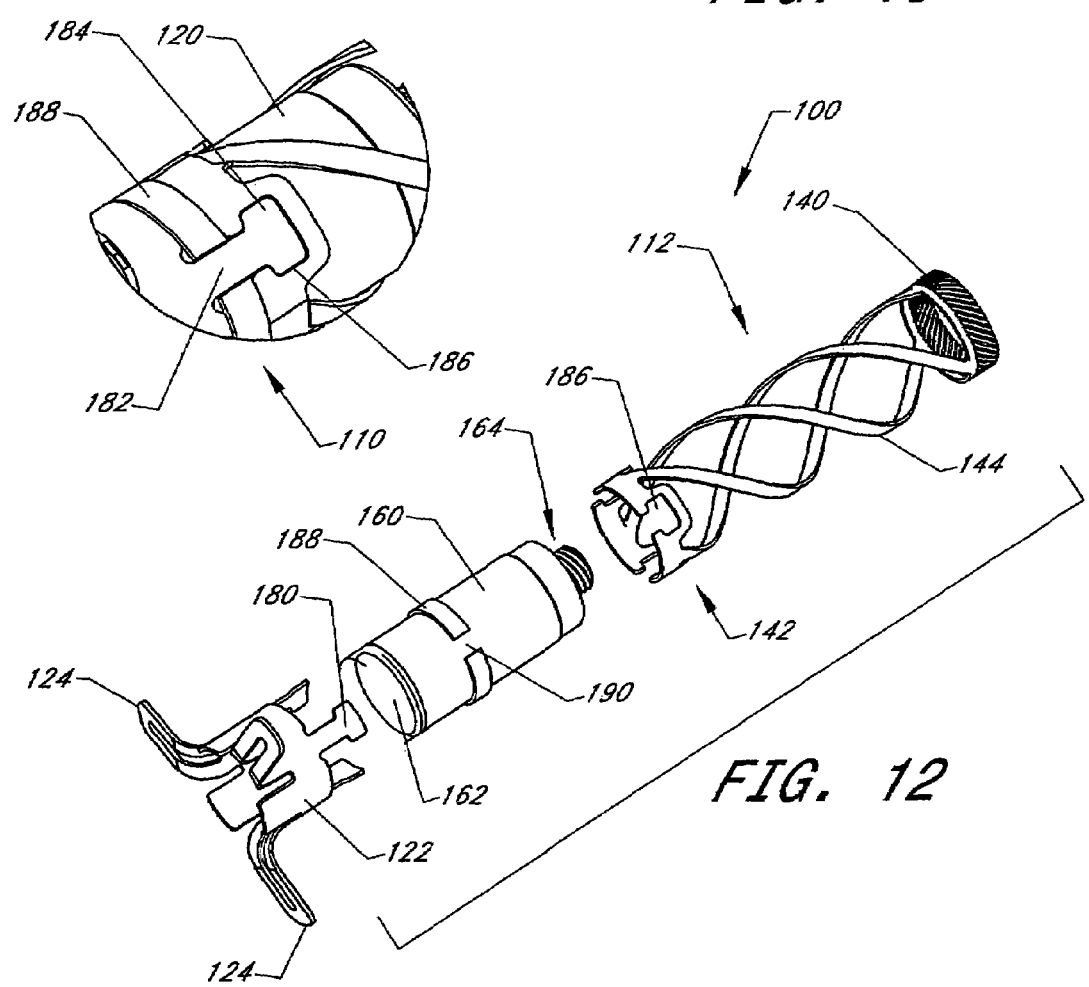

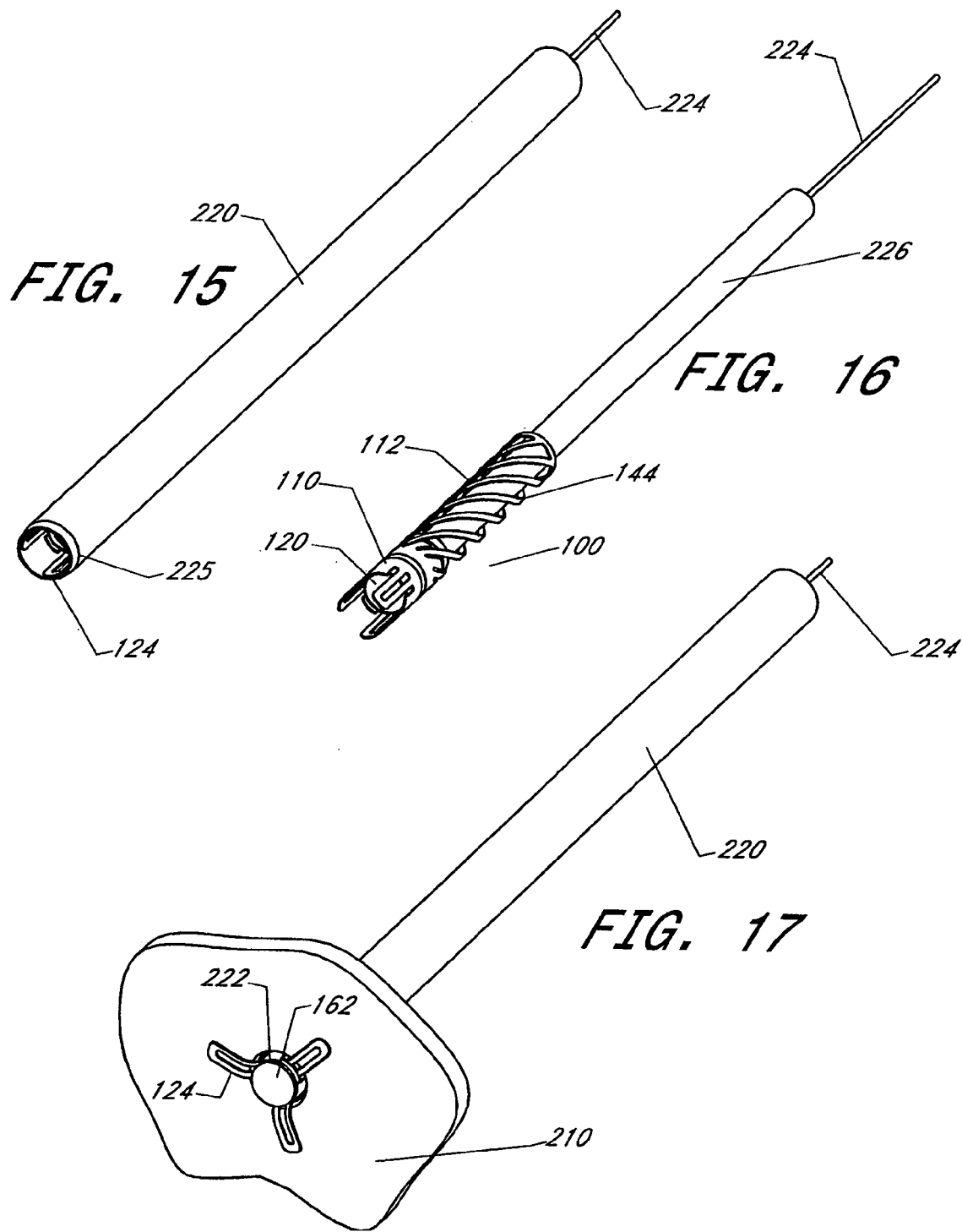

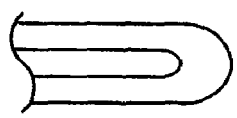 Single, straight
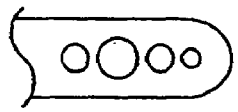 Holes, diverse
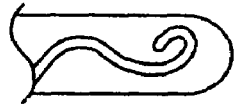 Curved
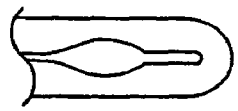 Varying width
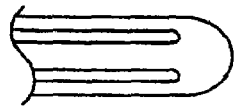 Multiple
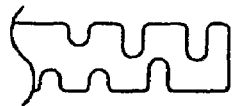 Keyed
 Combos
 Curved leg
*FIG. 26*

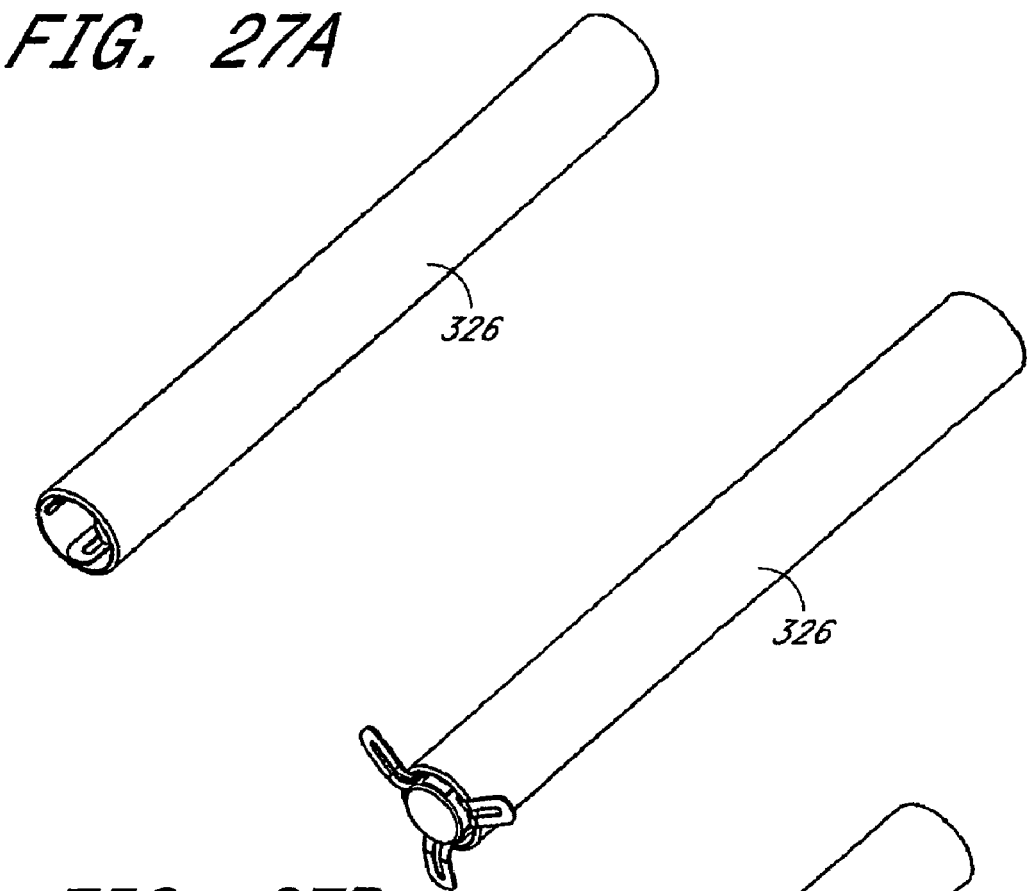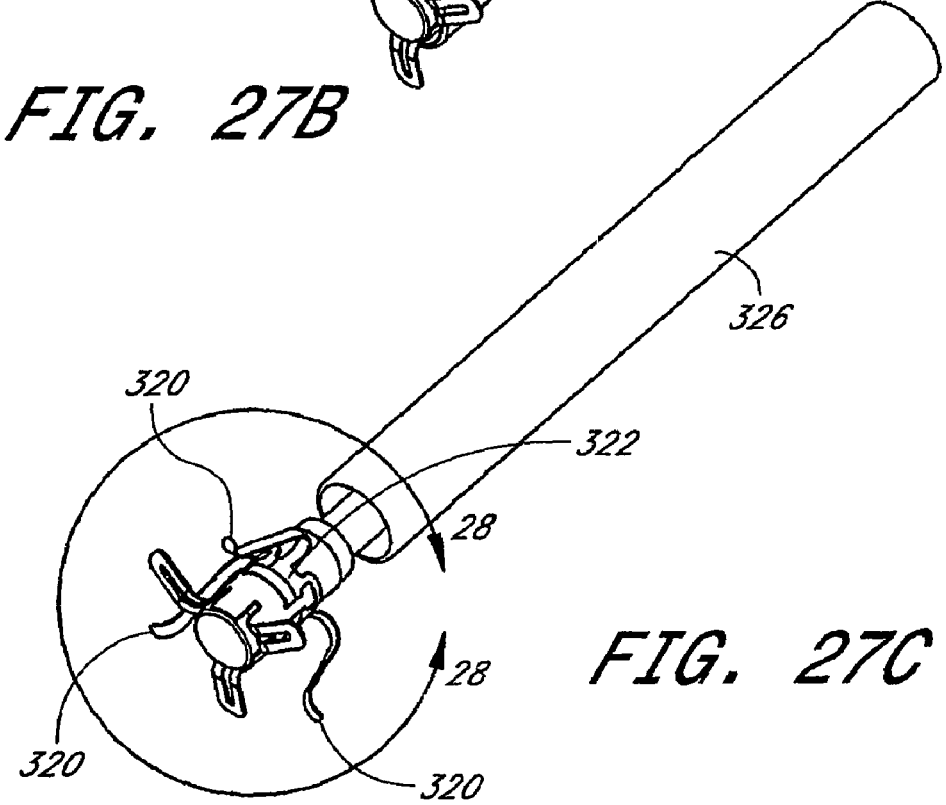

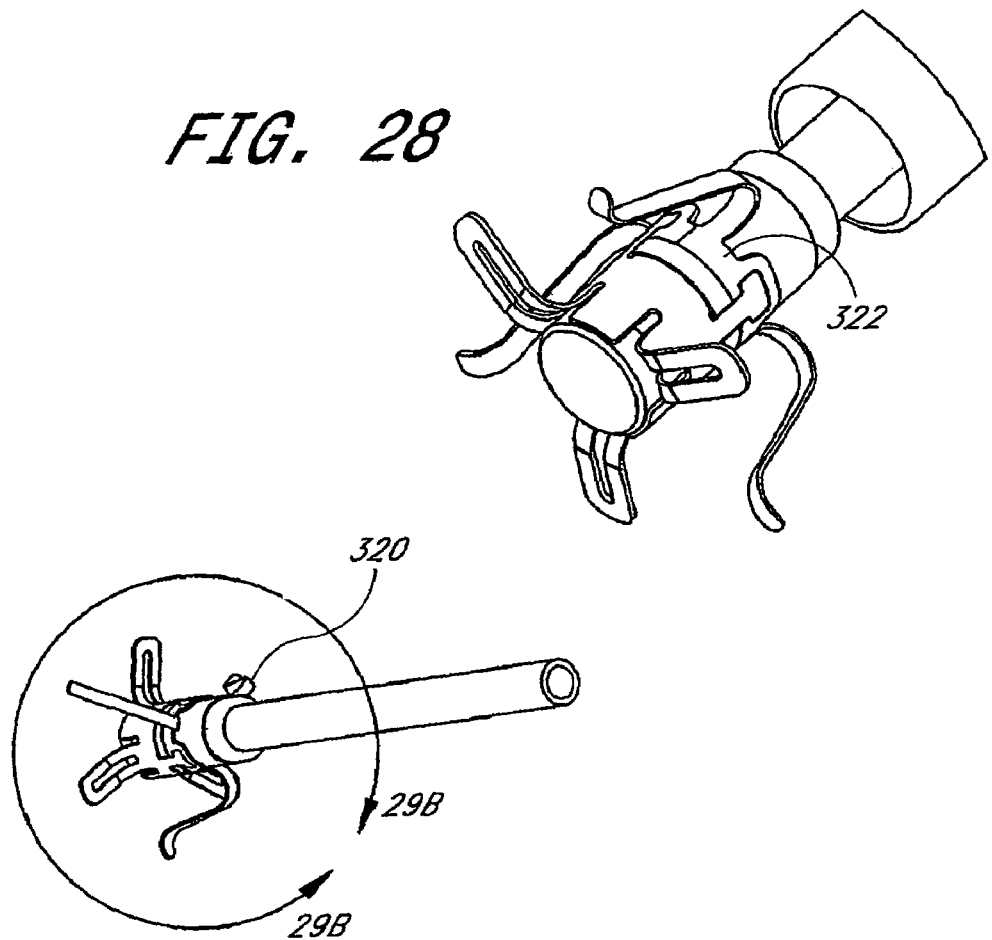
FIG. 28
FIG. 29A
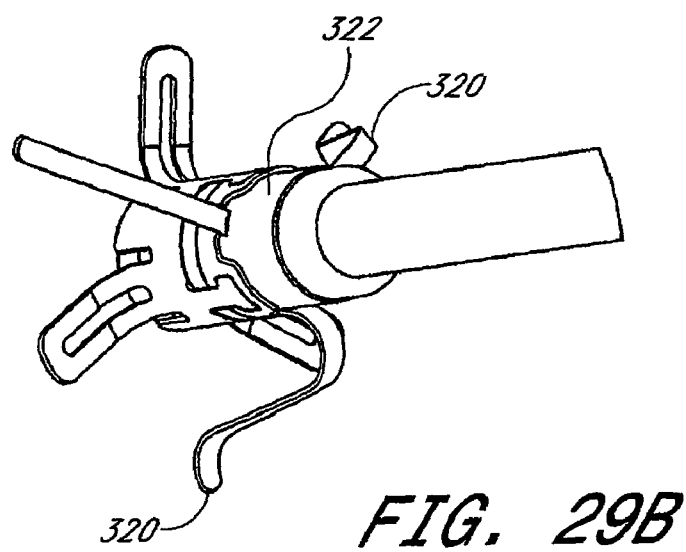
FIG. 29B

IMPLANTABLE PRESSURE TRANSDUCER SYSTEM OPTIMIZED FOR ANCHORING AND POSITIONING

CROSS-REFERENCE TO RELATED APPLICATIONS

The present application is a continuation of co-pending U.S. application Ser. No. 11/111,691 filed Apr. 21, 2005, which 1) claims priority under 35 U.S.C. §119(e) to U.S. Provisional Application No. 60/564,315 filed Apr. 22, 2004, and 2) is also a continuation-in-part of U.S. application Ser. No. 10/672,443 filed Sep. 26, 2003, now U.S. Pat. No. 7,149,587 which claims priority under 35 U.S.C. §119(e) to U.S. Provisional Application No. 60/413,758 filed Sep. 26, 2002, the disclosures of which are incorporated by reference herein in their entirety.

BACKGROUND OF THE INVENTION

1. Field of the Invention

This invention relates generally to systems and methods for optimizing the performance and minimizing complications related to implanted sensors, such as pressure sensors, for the purposes of detecting, diagnosing and treating cardiovascular disease in a medical patient.

2. Description of the Related Art

There are approximately 60 million people in the U.S. with risk factors for developing chronic cardiovascular diseases, including high blood pressure, diabetes, coronary artery disease, valvular heart disease, congenital heart disease, cardiomyopathy, and other disorders. Another 10 million patients have already suffered quantifiable structural heart damage but are presently asymptomatic. Still yet, there are about 5 million patients with symptoms relating to underlying heart damage defining a clinical condition known as congestive heart failure (CHF). Although survival rates have improved, the mortality associated with CHF remains worse than many common cancers. The number of CHF patients is expected to grow to 10 million within the coming decade as the population ages and more people with damaged hearts survive.

CHF is a condition in which a patient's heart works less efficiently than it should, and a condition in which the heart fails to supply the body sufficiently with the oxygen-rich blood it requires, either during exercise or at rest. To compensate for this condition and to maintain blood flow (cardiac output), the body retains sodium and water such that there is a build-up of fluid hydrostatic pressure in the pulmonary veins that drain the lungs, which is generally equivalent to the left atrial pressure. As hydrostatic pressure exceeds oncotic pressure and lymph flow, fluid transudates from the pulmonary veins into the pulmonary interstitial spaces, and eventually into the alveolar air spaces. This complication of CHF is called pulmonary edema, which can cause shortness of breath, hypoxemia, acidosis, respiratory arrest, and death. Although CHF is a chronic condition, the disease often requires acute hospital care. Patients are commonly admitted for acute pulmonary congestion accompanied by serious or severe shortness of breath.

One relatively new approach for treating cardiovascular disease is to implant sensors, such as pressure sensors in various chambers of the heart or adjacent vasculature such as the pulmonary arteries or veins, for the purposes of detecting early cardiac decompensation and prevention of pulmonary congestion and edema. Another potential advantage of implanted pressure transducers is that they may be useful in preventing overtreatment with resultant hypoperfusion of vital organs such as the kidneys. Such an approach utilizing a left atrial pressure transducer coupled with a medical therapy optimization system is described by Eigler et al. in U.S. Pat. No. 6,328,699, herein incorporated by reference.

One particular type and method of sensor placement is known as transmural placement where the sensor device enters the desired location by perforation of the tissue wall separating the outside the structure to inside the structure. Generally the sensor device resides on both sides and within a wall separating parts of the body, parts of an organ such as the heart, or separating a body structure form the rest of the body (the wall of a blood vessel). Sensor packages can be transmurally placed in the left atrium of the heart by a minimally invasive percutaneous catheter based procedure known as transseptal catheterization as originally described by Ross (Ross, J., Jr.: Transseptal left heart catheterization: A new method of left atrial puncture. Ann. Surg. 1949:395, 1959) and Cope in 1959 (Cope, C.: Technique for transseptal catheterization of the left atrium: Preliminary report. J. Thorac. Surg. 37:482, 1959), and modified by Brockenbrough and Braunwald in 1960 (Brockenbrough E C, Braunwald E: A new technique for left ventricular angiocardiography and transseptal left heart catheterization. Am J Cardiol 6:1062, 1960) and subsequently by Ross in 1966 (Ross J Jr.: Considerations regarding the technique for transseptal left heart catheterization. Circulation 34:391, 1966), all herein incorporated by reference. More invasive surgical procedures can transmurally place sensor devices in any cardiac chamber or blood vessel of sufficient size including the pulmonary arteries and veins.

Implantable pressure transducers are known in the art. For example, U.S. Pat. Nos. 4,023,562, 4,407,296, 4,407,296, 4,485,813, 4,432,372, 4,774,950, 4,899,751, 4,899,752, 4,986,270, 5,027,816, 4,353,800, 4,846,191, and 6,379,308 describe various types of pressure sensors. However, pressure sensors that are currently described in the art are not suitable for chronic implantation in the body for several reasons. For example, some pressure transducers are not hermetically sealed, or otherwise properly protected, and thus susceptible to degradation by bodily fluids. Other transducers are constructed such that their specific geometries or components cause thrombus formation, a potentially life threatening condition. Several transducers are constructed in a manner that result in significant "drift" of the pressure sensor, either due to tissue overgrowth or some other mechanism, thus resulting in inaccurate pressure measurements, which in many cases cannot be properly or easily recalibrated. Thus, there still remains a need in the art for an implantable sensor, such as a pressure transducer, that is stable, safe, effective, accurate, and, if needed, easily recalibrated.

This invention relates generally to systems and methods for optimizing the performance and minimizing complications related to implanted sensors, such as pressure sensors, for the purposes of detecting, diagnosing and treating cardiovascular disease in a medical patient. Systems and methods for anchoring implanted sensors to various body structures are also provided.

SUMMARY OF THE INVENTION

Several embodiments of the present invention relate generally to implantable physiological sensors. In one embodiment, a pressure sensor, or pressure transducer, that is suitable for chronic implantation in the body is provided. In another embodiment, a pressure transducer system that exhibits long-term stability following chronic implantation in the cardiovascular system is provided. In one embodiment, the pressure transducer remains stable despite the biological reactions that these systems induce. The sensors and methods described in some of the embodiments facilitate optimal healing and subsequent stability of transmurally implanted pressure sensors. Several embodiments of the current invention are particularly advantageous because they reduce the risk of thrombus formation and are not as susceptible to tissue overgrowth that causes drift of the pressure sensor. Other embodiments of the invention are designed to optimize performance. In one embodiment, deployment devices, anchoring means and/or retrieval tools are provided in conjunction with the sensor. In another embodiment, the sensor is at least partially enclosed in protective packaging. In another embodiment, the sensor is designed to minimize viscoelastic drift. In yet another embodiment, temperature compensation is provided. In a further embodiment, the effects of output artifacts, or side loading, are minimized.

In some embodiments, the implantable pressure sensing system, comprises one or more sensing interfaces. The phrase "sensing interface" as used herein shall be given its ordinary meaning and shall also include one or more materials or structures that protects a sensor from direct exposure to the environment (e.g., blood, tissue, etc.) while still preserving the sensor's sensing function. Sensing interfaces include, but are not limited to, diaphragms, hydrogels, metallic foils, plastics, membranes and other materials. In several embodiments, at least a portion of the sensing interface is configured to minimize thrombosis. As used herein the phrase "reduce thrombosis" shall be given its ordinary meaning and shall also include the partial prevention, reduction, hindrance or destruction of a blood clot or thrombus by, for example: (1) pharmacological agents that affect clot or thrombus formation, growth, or dissolution; (2) the promotion of neoendothelial overgrowth by, for example, providing growth channels or biological agents that facilitate tissue growth; and/or (3) comprising a thrombosis resistant coating or a coating that reduces platelet (or other blood component) activation or aggregation.

In one embodiment, an implantable pressure sensing system is provided, comprising a pressure sensor assembly, said pressure sensor assembly comprising a sensing interface having a first face and a second face and at least one pressure sensing unit comprising a sensing surface and non-sensing surface, wherein said pressure sensing unit contacts said second face of said sensing interface, and a sensor housing, wherein said sensor housing is hermetically sealed to said pressure sensor assembly, wherein at least portion of said sensing interface is adapted to reduce thrombosis. In some embodiments, said sensing interface of the pressure sensor assembly comprises a diaphragm. In some embodiments, at least one said pressure sensing unit comprises a strain gauge. In one embodiment, said sensing interface and said pressure sensing unit are integrally formed in a micro electromechanical systems device. Said diaphragm may comprise a plurality of grooves to facilitate tissue ingrowth. At least a portion of said diaphragm may have a biocompatible coating. Said biocompatible coating may be bio-stable or bio-erodable. Said biocompatible coating may be resistant to thrombus formation, capable of controlling tissue ingrowth, configured to reduce formation of fibrous tissue or not reduce growth of endothelial tissue. In some embodiments, at least a portion of said sensor housing is configured to resist transmission of side-load forces to said sensing interface under physiologic conditions. Said sensor housing may comprise a side-loading force absorbing structure about the sensing interface. In some embodiments, at least a portion of said sensor housing has a polished surface and/or a thrombosis-resistant coating. In one embodiment, said sensor housing comprises one or more materials selected from the group consisting of nitinol, stainless steel alloys, titanium alloys, cobalt chromium, tantalum, a ceramic, a glass or combination thereof. In some embodiments, the invention further comprises a drug-eluting component. Said drug-eluting component may comprise a plurality of reservoirs on the surface of said sensor housing with depots of one or more releasable treatment agents. Said drug-eluting component may further comprise a drug for controlling neointimal thickness. In some embodiments, said diaphragm is configured to resist the inhibition of diaphragm motion by overlying tissue overgrowth. In some embodiments, said diaphragm has a compliance substantially lower than the compliance of physiological levels of overlying tissue overgrowth. In one embodiment, said diaphragm has an average thickness sufficient to provide a compliance substantially lower than the compliance of physiological levels of overlying tissue overgrowth while capable of a displacement sufficient for said strain gauges to generate a usable sensor signal over a physiological range of blood pressures. In one embodiment, said diaphragm has a diameter of about 2.5 mm and an average thickness of about 25 microns to about 76 microns. In another embodiment, said diaphragm has a diameter of about 2.5 mm and an average thickness of about 76 microns to about 127 microns. In still another embodiment, said diaphragm has a diameter of about 2.5 mm, an average thickness of about 50 microns, and a displacement of about 4 nm at about the center of said diaphragm. In one embodiment, said diaphragm has a compliance of about 10,000 times less or lower than the compliance of physiological levels of overlying tissue overgrowth. In another embodiment, said diaphragm has a compliance of about 100,000 times less or lower than the compliance of physiological levels of overlying tissue overgrowth. In one embodiment, said first face and said second face of said diaphragm are generally flat to enhance diaphragm displacement capability. Said diaphragm may comprise a material selected from a group consisting of titanium or Ti 4-6. In some embodiments, the sensor housing further comprises a filling material within the sensor housing. In some embodiments, the filling material is selected from one or more of the group comprising helium, argon or other noble gas, an electrical insulating liquid, or a moisture absorbent material.

In one embodiment, an implantable pressure sensing system is provided, comprising a pressure transducer assembly comprising a micro electromechanical systems pressure transducer; said pressure transducer having a first face with a sensing surface and a non-sensing surface, and a second face having a connection area and a non-connection area, a sensor housing, wherein said sensor housing is hermetically sealed to said pressure transducer assembly, wherein said sensing surface of the pressure transducer is configured to reduce thrombosis. Said sensor housing may be hermetically sealed to said pressure transducer assembly at the non-sensing surface of said first face. In other embodiments, said sensor housing is hermetically sealed to said pressure transducer assembly at the non-connection area of said second face. In one embodiment, said sensor housing is hermetically sealed to said pressure transducer assembly with a gold-silicon bonding layer.

In one embodiment, a device for monitoring a patient is provided, comprising a means for sensing a physiological parameter, an implantable means for housing the sensing means, a means for interfacing the sensing means with the patient environment, and a means for reducing thrombosis on the interfacing means.

In one embodiment, an implantable pressure sensing system is provided, comprising a pressure transducer assembly comprising a micro electromechanical systems pressure transducer; said pressure transducer having a first face with a sensing surface and a non-sensing surface, a second face having a connection area and a non-connection area, and a sensor housing, wherein said sensor housing is hermetically sealed to said pressure transducer assembly. Said sensor housing may be hermetically sealed to said pressure transducer assembly at the non-sensing surface of said first face, or at the non-connection area of said second face. In some embodiments, said sensor housing is hermetically sealed to said pressure transducer assembly with a gold-silicon bonding layer.

In one embodiment, an implantable sensing system is provided, comprising a biocompatible sensor housing, a pressure sensing interface hermetically sealed to the sensor housing, and a plurality of strain gauges joined to the pressure interface, wherein the plurality of pressure sensors are arranged in a Wheatstone bridge configuration. In some embodiments, at least one said pressure sensors comprises a silicon strain gauge. Said silicon strain gauge may further comprise an insulation layer. In a further embodiment, said insulation layer comprises silicon dioxide grown on the bottom of said silicon strain gauge. In some embodiments, the plurality of pressure sensors comprises an inner set of strain gauges and an outer set of strain gauges, wherein said inner set is generally located about the center of said second face of said sensing interface and said outer set is generally located near the periphery of said second face of said sensing interface. In some embodiments, said inner set of strain gauges and said outer set of strain gauges may be generally oriented orthogonally on said second face of said sensing interface, or may be generally oriented about 180 degrees apart on said second face of said sensing interface. Some embodiments of the invention further comprise a temperature compensation system. Said temperature compensation system may comprise a temperature sensing element capable of providing temperature-related information over a physiological range of temperatures. Said temperature compensation system may be a temperature compensating arrangement integral with said plurality of strain gauges, wherein said plurality of strain gauges are resistive strain gauges arranged in a Wheatstone bridge configuration. In one embodiment, at least one strain gauge has a frequency response from about 500 Hz to about 2000 Hz. In other embodiments, at least one strain gauge has a frequency response less than about 500 Hz. In one embodiment, at least one strain gauge has a frequency response greater than about 2000 Hz. The invention may further comprise at least one semiconductor component configured to at least one function selected from the group comprising: power control, pressure signal transduction, local signal processing and data telemetry.

In one embodiment, an implantable pressure sensor is provided, comprising a means for pressure sensing in the body, a means for housing said sensing means chronically in a body, and a means for providing temperature correction for the pressure sensing means.

In one embodiment, a method for monitoring a patient is provided, comprising, providing a hermetically sealed pressure transducer in a body, detecting a pressure signal with the hermetically sealed pressure transducer; and modulating the pressure signal with a temperature-related signal. In some embodiments, the temperature-related signal originates from a temperature sensor. In some embodiments, the temperature-related signal originates from a plurality of resistive strain gauges in a Wheatstone bridge configuration.

In one embodiment, a physiological lead system is provided, comprising an elongate member having a proximal end and a distal end, a lead system located generally at the distal end of said elongate member; and a distal anchor assembly engaged to said elongate member, said distal anchor assembly comprising at least one protruding member with at least one tissue ingrowth path. In some embodiments, at least one said tissue ingrowth path comprises a straight, fixed-width slit. In one embodiment, at least one said tissue ingrowth path comprises a hole in said protruding member. In one embodiment, said protruding member comprises a plurality of holes of similar diameters. In one embodiment, said protruding member comprises a plurality of holes of different diameters. In one embodiment, at least one said tissue ingrowth path comprises a curved slit. In one embodiment, at least one said tissue ingrowth path comprises a variable width slit. In one embodiment, at least one said tissue ingrowth path comprises a groove. In one embodiment, at least one said protruding member has a curved or angled configuration. In some embodiments, the curved or angled configuration of said protruding member lies in the same plane as the longitudinal axis of said elongate member. In another embodiment, the curved or angled configuration of said protruding member lies in the same plane as a perpendicular radial cross section of said elongate member.

In another embodiment said distal anchor assembly is engaged to said elongate member at a separation distance from said lead system such that said lead system is substantially unaffected by forces acting said distal anchor assembly.

In another embodiment, the physiological lead system further comprises a proximal anchor assembly engaged to said elongate member generally between said distal anchor assembly and the proximal end of said elongate member. In one embodiment, at least a portion of said distal anchor assembly has a biocompatible coating. In one embodiment, at least a portion of one said tissue ingrowth path has a biocompatible coating. In one embodiment, the invention further comprises a drug-eluting system. In a further embodiment, said drug-eluting system comprises a coating on said distal anchor assembly. The drug-eluting coating may be configured for a particular elution rate or elution duration. Said drug-eluting system may further comprise a drug for controlling neointimal thickness. In some embodiments, at least a portion of said distal anchor assembly has a biocompatible coating. Said biocompatible coating may be bio-stable or bio-erodable. Said biocompatible coating may be resistant thrombus formation, capable of controlling tissue ingrowth, resistant to corrosion, capable of reducing formation of fibrous tissue, and/or configured not prevent growth of endothelial tissue. In one embodiment, said biocompatible coating comprises a corticosteroid. In one embodiment, said biocompatible coating comprises parylene. Said elongate member may further comprise a removable stylet and a stylet lumen.

In one embodiment, a sensor is designed to minimize viscoelastic drift. The thickness of epoxy adhesive attaching strain gauges to diaphragm may be minimized by growing a silicon dioxide or other insulating layer on the bottom of the silicon strain gauges or the metallic diaphragm, so that adhesive does not also have to serve as an insulating layer.

In one embodiment, viscoelastic drift is calibrated, predicted, and corrected. In one embodiment, viscoelastic properties of the pressure transducer are characterized during pre-implant calibration. In one embodiment, known viscoelastic properties are used in combination with the recorded pressure variations over time to obtain pressure measurements that are corrected for viscoelastic drift. In one embodiment, a software algorithm is used to automatically correct for viscoelastic drift due to varying average pressure.

In one embodiment, effects of side loading on the sensor are minimized. In one embodiment, at least a portion of the casing adjacent to the diaphragm is made substantially inflexible and non-distortable such that the diaphragm is not distorted by side-load forces under physiologic conditions. In one embodiment, a fixation anchor attachment to the housing is located as far as possible from the portion of the housing that supports the diaphragm, so that forces exerted by the anchor legs cause less distortion of the diaphragm. In one embodiment, strain gauges are oriented 90° from each other rather than the standard 180° orientation, and connected in a Wheatstone bridge configuration such that differential resistance changes between the strain gauges substantially cancel, while common-mode changes in resistance are additive. Any feature mentioned above may be used in combination with others.

In one embodiment, thrombogenicity of the sensor is minimized by polishing, including electropolishing, coating, including parylene, a small surface area, a low profile, a profile configured to reduce flow disruption and/or encouraging rapid tissue overgrowth/ingrowth.

In one embodiment, materials that promote rapid tissue coverage, heal without chronic inflammation, and develop a thin covering of neointima are provided. These may include alloys of stainless steel, Nitinol, titanium alloys, cobalt chromium and/or tantalum.

In one embodiment, pressure artifacts due to atrial wall stresses are minimized by providing features on the sensor housing that reduce the coupling of these stresses to the sensor diaphragm. In one embodiment, the sensor housing comprises grooves, threads, or tabs generally around its distal circumference to anchor tissue overgrowth, reducing the coupling of stress within the tissue to the sensor diaphragm. In one embodiment, the sensor housing comprises a cylindrical rim that extends distally beyond and surrounding the sensor diaphragm, providing a barrier protecting the diaphragm from the transmission of tissue stresses.

In another embodiment, coupling of wall stresses is minimized by providing for drug delivery from a ring or band about the distal circumference of the sensor housing. The drug may include an antiproliferative agent such as paclitaxel or sirolimus, as is known in the field of drug eluting stents to prevent restenosis. Other bioactive drugs to reduce proliferation, thrombosis or inflammation, as are known to those skilled in the medical arts may also be used. In one embodiment, a source of ionizing radiation is provided in a band around the distal circumference of the sensor. It is known by those skilled in the art that ionizing radiation reduces or prevents tissue proliferation following tissue injury. In one embodiment, the sensor diaphragm comprises a radioactive source such as Phosphorus-32 or Strontium-90, which are known to emit beta particles that can reduce tissue proliferation.

In one embodiment, improved sensor reliability and accuracy is provided.

In one embodiment, improved sensor positioning stability is provided.

In one embodiment, elution of one or more drugs to reduce neointimal thickness is provided.

In one embodiment, slow release of low doses over longer periods is provided.

In one embodiment, slots, grooves, or holes in distal anchor legs to minimize path lengths for tissue ingrowth are provided.

In one embodiment, an implantable pressure monitor is provided, said monitor comprising distal anchors, said anchors comprising one or more legs, said legs configured with one or more slots for the purpose to advantageously promote more rapid tissue overgrowth in a deployed position, which will advantageously aid in securement of the device to the septum wall and prevent thrombus formation. In another embodiment, the slots in the legs can vary in width. In another embodiment, the slots in the legs can be curved or serpentine. In another embodiment, the slots in the legs may be replaced by one or more holes of equal or diverse diameters. In yet another embodiment, the legs can be keyed or slotted at right angles to their long axes from one or both sides.

In one embodiment, surface grooves are formed on the diaphragm to promote rapid tissue ingrowth. The shape of groove long axis may be linear, serpentine, circumferential or any other beneficial groove shape. The cross-sectional shape of groove may be rectangular, triangular ("Vee"), semi-round or any other beneficial shape. The grooves may be filled with or coated by bio-stable or bio-erodable polymer or other coating agents, including one or more drugs that control tissue growth rate or thrombus formation In one embodiment, biocompatible coatings such as parylene are provided. Such coatings may minimize platelet adhesion and aggregation, provide electrical insulation (for pacing) and/or prevent corrosion of metallic components.

In one embodiment, the invention comprises a coating on the diaphragm surface and/or on anchor surfaces that inhibits or minimizes the formation of undesirable fibrous tissue, while not preventing the beneficial growth of an endothelial covering.

In one embodiment, a plurality of small indentations or holes in the device or anchor surfaces are provided to serve as depots for controlled release of antiproliferative substances In one embodiment the invention, a pressure transducer is provided that is designed so that calibration parameters are minimally affected by tissue overgrowth, and may include a very low compliance diaphragm compared with tissue overgrowth, and/or diaphragm thickness maximized to minimize compliance, consistent with sufficient compliance to derive adequate transducer signal. In one embodiment, the 2.5 mm diameter diaphragm is between about 0.001 to 0.003 inches (25 to 76 microns) thick. In another embodiment, the diaphragm thickness is between about 0.003 to 0.005 inches (76 to 127 microns). In one embodiment, a 2.5 mm diameter by 50-micron thick titanium foil diaphragm has a displacement at its center of only about 4 nm per mm Hg pressure change. In one embodiment, a pressure transducer diaphragm constructed of Ti 6-4 with material properties comprising of approximately $R_0=1.1$ mm, $v=0.31$, $t=0.05$ mm, and $E=100$ GPa is provided. In another embodiment, a low compliance pressure transducer is fabricated from, for example, silicon, using micro electromechanical systems (MEMS) techniques. In one embodiment, a diaphragm is manufactured to maximize flatness, which maximizes gain for a given diaphragm thickness, is provided.

In one embodiment, a pressure sensor includes temperature compensation so that pressure measurements will be minimally affected by temperature change is provided. In one embodiment, an apparatus to measure temperature at the site of the sensor is provided. In one embodiment, the temperature compensation or modulation is achieved by using multiple resistive strain gauges arranged in a Wheatstone bridge, such that the electrical voltage output of the bridge is proportional to the ratio of two or more resistances, all of which depend on temperature in a similar way, thus reducing the affect of temperature on the pressure reading. It can also be achieved by selecting resistive strain gauges with essentially identical temperature coefficients, and connecting the strain gauges in a Wheatstone bridge configuration.

In one embodiment, an internal thermometer that is independent of pressure is provided where prior to implantation calibrating the temperature coefficient of the pressure reading based on this measured temperature. After implantation the measured temperature is used to select the appropriate pressure calibration coefficients. In one embodiment, a band-gap voltage reference is used to create a current proportional to absolute temperature that is then compared to the temperature-independent voltage reference, thereby deriving a measure of temperature.

In one embodiment, the device can be easily recalibrated using non-invasive method, such as a Valsalva maneuver and/or offset calibration, where the gain is not affected by tissue.

In one embodiment, complete encasement of system within a hermetic housing is provided to protect against the damaging effects of bodily fluids. The sensor may be enclosed in metal packaging. Environmental pressure may be coupled to sensor through a diaphragm bonded to the metal housing.

In one embodiment, a delivery catheter permits simultaneous measurement of fluid pressure from the catheter tip during transducer package transit and deployment. The delivery catheter is configured to be sufficiently large in diameter to allow the catheter to be filled with a continuous cylindrical column of fluid surrounding the sensor module and its lead. The delivery catheter permits injection of radiographic contrast material with the transducer system in its lumen to localize positioning during transducer system deployment. Positioning can be determined under fluoroscopy by contrast injection and pressure measurement thought side arm port the delivery catheter. In one embodiment, after the distal anchor legs expand to assume their expanded state on a distal side of the septum wall, contrast material is injected to assure correct positioning in the left atrium. The catheter is further retracted while holding the stylet and sensor assembly in place until the distal edge of the catheter is coincident with the proximal end of the sensor assemble, which can be verified by visualizing the alignment of the radiopaque markers on the sensor assembly and the delivery catheter under fluoroscopy. Further contrast is injected while the entire catheter, stylet and sensor assembly are retracted in 1 to 2 mm increments until contrast material is fluoroscopically observed exiting the tip of the catheter into the right atrium. At this point further retraction of the catheter will expose the proximal anchor, allowing it to relax to its expanded state on a proximal side of the septum wall.

In one embodiment, the proximal portion of the catheter may contain a hemostatic assembly or adapter to prevent back bleeding through the catheter around the pressure transducer system and to prevent the entrainment of air during transducer insertion and advancement. In one embodiment, the introducer sheath is made of transparent tubing, such as acrylic, advantageously allowing the operator to verify that all air bubbles have been flushed from the introducer sheath before it is inserted through the hemostatic adapter of the delivery sheath.

In one embodiment, the transducer module and/or its fixation anchors may have radiographic markers to enhance visualization during deployment. The legs of the distal anchor may be positioned at the distal end of the delivery catheter, which can be visually verified under fluoroscopy by noting the alignment of the distal radiopaque marker on the distal end of the delivery catheter with that on the distal end of the sensor assembly.

In one embodiment, the sensor lead is configured to accept a stylet that is preferably configured to provide sufficient column strength to allow the anchor and sensor assembly to be held in place relative to the septum during deployment, while the catheter is retracted to expose and deploy the distal anchor legs. Alternatively, the catheter can be held in place and the stylet and sensor assembly can be advanced to deploy the distal anchor legs.

In one embodiment, a physiological sensing device optimized for placement in the left atrium of the heart by a percutaneous catheter-based procedure that traverses the intra-atrial septum is provided.

In one embodiment, a physiological sensing device optimized for placement in a pulmonary vein by an open surgical procedure is provided.

In one embodiment, a transducer system optimized for placement through the free wall of the left atrium, or through the wall of the left atrial appendage, or across the right atrial free wall or right atrial appendage or transmurally into the main or branch pulmonary arteries by a minimally invasive thorascopic surgical procedure or by a traditional open surgical approach is provided.

In one embodiment, intrathoracic pressure may be monitored by placement of the pressure transducer system through the chest wall or diaphragmatic respiratory muscles by local puncturing techniques, under direct or fiberoptic endoscopic vision, or by robotic surgical manipulation.

In one embodiment, a physiological sensing device is provided, wherein internal transducer components comprises a transducer, power, and communications components are enclosed in a hermetic casing or housing called a transducer module. The casing comprises metal, ceramic, or glass, alone or in combination, or other constituents known to skilled artisans for constructing hermetic packaging. The distal end of the module comprises at least one hermetic diaphragm designed to translate or flex in response to pressure changes at the desired location. The diaphragm or membrane is mechanically coupled to enclosed transducer components. The sensor package may be provided in a wide range of sizes and shapes. The sensor package is cylindrical in shape with a distal end and a proximal end. In one embodiment, the module is between about 1 mm and 5 mm long, and 3 mm in diameter. In another embodiment, the module is between about 5 mm and about 15 mm long. In another embodiment, the package is about 8 mm long, and about 3 mm in diameter. In one embodiment, the package is less than about 1 mm in diameter. In another embodiment, the package is less than about 10 mm long. In one embodiment, the package may be rectangular, square, spherical, oval, elliptical or any other shape suitable for implantation. In one embodiment, the sensor package is rigid, and in another embodiment, the sensor package is flexible. In one embodiment, the sensor module includes a cylindrical housing comprising one or more component pieces of titanium CP, titanium 6-4, or other suitable biocompatible metallic alloy or other material suitable for making a hermetic package such as ceramic material like alumina or zirconia. One embodiment of the invention comprises a titanium cylindrical housing, and a diaphragm comprising a titanium foil that is diffusion bonded or otherwise hermetically affixed to the titanium housing. In another embodiment, the diaphragm and housing may be machined, lapped, or otherwise manufactured from titanium bar or rod stock so that part of the cylindrical housing and the diaphragm are one piece.

In one embodiment, enclosed transducer components are provided, comprising semiconductors that control power, pressure signal transduction, local signal processing, and data telemetry. Resistive strain gauges are bonded, or otherwise coupled, to the inside surface of the diaphragm.

In one embodiment, a titanium cylindrical housing comprising an application-specific integrated circuit (ASIC) or "measurement electronics" is provided. Measurement electronics are contained within the housing and electrically connected to the strain gauges by fine gold wires or other means of electrical connection. In one embodiment, the proximal end of the housing is sealed by a zirconia ceramic feedthrough that is brazed to a titanium cylinder. In one embodiment, the housing contains a gaseous atmosphere. In one embodiment, a gaseous atmosphere is provided, which may comprise helium, argon, or any other advantageous gas or combination of gases known to skilled artisans. In one embodiment, a moisture-absorbant material is included within the housing. In one embodiment, the housing is evacuated prior to sealing. An electrical insulating liquid such as an oil or other electrically insulating liquids known to skilled artisans may be contained within the housing. In one embodiment, the implanted module contains an internal power source, such as a battery. In another embodiment, the module is powered transcutaneously by induction of radio frequency current in an implanted wire coil connected directly to the module or connected by a flexible lead containing electrical conductors, to charge a internal power storage device such as a capacitor. In one embodiment, the pressure sensor is fabricated by micro electro-mechanical systems (MEMS) techniques.

In one embodiment, a method for hermetically sealing a silicon device is provided. The silicon device is coupled to a sensor, such as a pressure transducer, which benefits from having direct contact with its environment (the body). In one embodiment, a method to hermetically seal the non-sensing portion of a silicon device while allowing the sensing portion (e.g. the pressure transducer) to have direct contact with the body is provided. A silicon chip, a gold preform and a metallic housing are each primed for sealing and are assembled. The assembly is then heated to react the gold preform to the silicon chip and to form a molten gold-silicon alloy in-situ to bind said metallic housing to the non-sensing portion of the silicon chip. In this way, the non-sensing portion of the silicon chip is hermetically sealed, while still permitting exposure of the sensing portion of the silicon chip to the environment In one embodiment, a physiological sensor system is provided with a configuration similar to a cardiac pacemaker, with a hermetically sealed housing implanted under the patient's skin (subcutaneous) and a flexible lead containing signal conductors with a hermetically sealed pressure transducer module at its distal end. The signal conductors may be electrical, fiber optic, or any other means of signal conduction known to skilled artisans. The lead may have a stylet lumen to aid with transducer deployment in the body of a medical patient. The lead may have a lumen for connection of the sensor module to a reference pressure. In one embodiment, the housing contains a battery, microprocessor and other electronic components, including transcutaneous telemetry means for transmitting programming information into the device and for transmitting physiological data out to an external programmer/interrogator.

In one embodiment, an implanted pressure sensor-lead combination is provided that is an integral part of a cardiac rhythm management system such as a pacemaker or defibrillator or various other implantable cardiovascular therapeutic systems known to skilled artisans.

In one embodiment, a physiologic sensor system is provided, in which the signal processing, and patient signaling components are located in a device external to the patient's body in communication with an implanted subcutaneous housing via any one or more of the various forms of telemetry well known in the art, such as two-way radio frequency telemetry. The subcutaneous housing can comprise only a tuned electrical coil antenna, or a coil antenna in conjunction with other components. Other designs for antennae are well known to those skilled in the art and are can be used in accordance with several embodiments of the present invention. In still another embodiment, the sensor module is directly connected to a coil antenna by short lead or lead of zero length such that the entire system resides in the heart. Such a system may have a small internal battery or power could be delivered transcutaneously by magnetic inductance or electromagnetic radiation of a frequency suitable for penetrating the body and inducing a voltage in the implanted coil antenna. In one embodiment, radiofrequency electromagnetic radiation is used with a frequency of about 125 MHz. In one embodiment, an implantable pressure sensing module that also comprises one or more sensors in addition to the pressure transducer is provided.

In one embodiment, a physiologic sensor system is provided, comprising a plurality of pressure transducers to measure pressures in the transmural space or locations proximal to the transmural space, or to measure differential pressure between the distal diaphragm and another location.

In one embodiment, a physiologic sensor system is provided, comprising a pressure transducer and one or more other types of sensors, said sensors including accelerometers, temperature sensors, electrodes for measuring electrical activity such as the intracardiac electrogram (IEGM), oxygen partial pressure or saturation, colorimetric sensors, chemical sensors for glucose or for sensing other biochemical species, pH sensors, and other sensor types that may be advantageous for diagnostic purposes, or for controlling therapy.

In one embodiment, pressure sensors with a frequency response of between about 500 and 2000 Hz are provided.

In one embodiment, pressure sensors with a frequency response of less than about 500 Hz and greater than 2000 Hz are provided.

In one embodiment, an implantable pressure sensor module comprising a separate hydrophone sensor is provided.

In one embodiment, an implantable sensor module that serves dual diagnostic and therapeutic functions is provided. Said sensor module contains at least one electrode for stimulating the organ in which it is placed. Said electrode or electrodes may be used for electrical pacing the left atrium In one embodiment, a method for generating a signal indicative of pressure in the left atrium is provided, based on components of a pressure waveform that are relative to each other and therefore do not have to be compensated for atmospheric pressure and are not subject to offset drift. In one embodiment, a method for generating a signal is provided, wherein the components of a pressure waveform comprise the pressure differential between the mean and respirator minima of the left atrial pressure waveform. The components of a pressure waveform comprise the relative heights and/or shapes of the left atrial "a," "c," and "v" waves. Decreased left ventricular compliance is the diagnosis when the "a" wave increases without shortening of the atrioventricular (AV) delay or in the presence of mitral stenosis. Increases in the "v" wave amplitude and merging with the "c" wave to produce a "cv" wave is usually indicative of acute mitral valve regurgitation. In another embodiment, atrial fibrillation and atrial flutter are detected by analysis of the LAP waveform. In another embodiment, spectral analysis of the LAP versus time signal is performed.

In one embodiment, a physiologic sensor system comprising components to obtain a signal indicative of pressure relative to atmospheric pressure is provided. An implanted apparatus for measuring absolute pressure at a location within the body is provided as above, which further communicates this information, as either an analog or digital signal, to an external signal analyzer/communications device. The external signal analyzer/communications device further contains a second pressure transducer configured to measure the atmospheric (barometric) pressure. The analyzer/communications device performs a calculation using the absolute pressure from the implanted module and the atmospheric pressure to obtain the internal pressure relative to atmospheric pressure, that is, difference between the absolute pressure at the location within the body and the absolute barometric pressure outside the body. In one embodiment, gauge pressure measurements are performed only when the implanted apparatus is queried by the external analyzer/communications device. In one embodiment, this is accomplished by having the external device supply operating power to the implant module to make the measurement. In another embodiment, this is accomplished by requiring a proximity RF link to be present between the external and implantable modules, immediately before, after and/or during the measurement. In another embodiment, differential pressure is obtained by the lead containing a lumen that communicates a reference pressure to the sensor module as well known to skilled artisans.

In one embodiment, an implantable pressure sensor module is provided, wherein the module is associated with proximal and distal anchoring systems that assure localized fixation of the distal end of the module and that the transducer diaphragm is essentially coplanar with the plane of the blood contacting surface of the desired chamber or vessel. The anchoring device is configured to cross the septum between the right and left atrium and trap itself between the two chambers such that a pressure-sensing member is exposed to the left atrium. In one embodiment, the distal anchor legs bend outwards until they are substantially perpendicular to the longitudinal axis of the cylindrical base portion of the sensor module. In alternative embodiments, the distal anchor legs bend proximally until they are oriented at more than 90° to the longitudinal axis of the cylindrical base portion of the sensor module. In such embodiments, the angle θ (which represents the amount beyond a perpendicular to the longitudinal axis that the distal anchor legs can bend) can be between about 0° and about 20°. In some embodiments, the angle θ can be between about 5° and about 15°. In one specific embodiment, the angle θ can be about 10°. In one embodiment, the angle θ will preferably be reduced to zero degrees when the distal anchor is deployed on a distal side of a septum wall with a proximal anchor on the proximal side of the wall due to the opposing force of the proximal anchor. In one embodiment, the angle θ is selected along with a spring constant of the distal anchor legs such that an opposing force applied by the proximal anchor through a septum wall of a particular thickness will cause the angle θ to be substantially reduced to zero or to deflect a small amount in the distal direction so as to conform with a substantially concave left atrial septal surface. In one embodiment, the distal anchor legs are configured such that when both the distal and the proximal anchors are deployed, contact between the distal anchors and the septal wall is distributed over the entire proximal side surface area of the distal anchor legs to minimize pressure-induced necrosis of the septum. The device is configured in a manner that will allow it to position the pressure-sensing member at a desired location relative to the septal wall while conforming to anatomical variations. In one embodiment, the diaphragm is essentially coplanar with the left atrial side of the intra-atrial septum. In one embodiment, the term "essentially coplanar" is defined as the plane defined by the outer surface of the diaphragm is within about ±0.5 mm distance of the plane tangential to the left atrial side of the intra-atrial septum at the location it is traversed by the pressure-monitoring module. In another embodiment, this distance is defined as about ±1 mm. In yet another embodiment of the present invention, this distance is defined as about ±2 mm. In one embodiment, the device is designed such that the diaphragm will not be recessed within the septal wall. In one embodiment the device is designed so that the surface of the diaphragm is positioned between 1 mm and 3 mm distally into the left atrium from the left atrial side of the intra-atrial septum.

According to one embodiment, the sensor system comprises a proximal anchor having one or more helical legs extending between a proximal ring and a distal ring. In one embodiment, the helical path of the proximal anchor legs passes through 360 degrees between the proximal ring and the distal ring. In alternative embodiments, the proximal anchor can be longer and/or the legs can pass through 720 degrees. In one embodiment, the legs pass through a substantially whole number of complete circles between the proximal and distal rings.

In one embodiment, an implantable sensor module is provided, comprising a proximal anchor having anchor legs, wherein the at least one of the anchor legs is configured to bend outwards and distally until in their fully expanded state, each leg forms a loop with a distal most edge that is positioned substantially distally from the distal edge of the distal ring. In one embodiment of the proximal anchor, the anchor assembly is configured such that, in a free space (i.e. with no tissue or material between the proximal and distal anchors), the distal edge of the proximal anchor leg loops and the proximal tissue-contacting surface of the distal anchor can actually overlap by up to about 0.06". In some embodiments the overlap can be between about 0.03" and about 0.05", and in one embodiment, the distance is about 0.04". In some non-overlapping embodiments, the distance between the distal edge of the proximal anchor leg loops and the distal edge of the distal ring of the proximal anchor can be between about 0.040" and about 0.070". In some embodiments, the distance is between about 0.050" and about 0.060", and in one particular embodiment, the distance is about 0.054".

In one embodiment, an implantable sensor module is provided, comprising a proximal anchor having anchor legs with sufficient resilience that they relax to positions that overlap the plane of the relaxed distal anchors, assuring that the assembly will be securely anchored to even the thinnest of septum walls. In one embodiment, an implantable sensor module comprises a proximal anchor, wherein the material and dimensions of the proximal anchor legs are selected such that the elasticity of the legs is matched to that of the tissue wall with which it is to be in contact, minimizing pressure-induced tissue necrosis and erosion of the device through the septum. In one embodiment, the device also comprises a distal anchor having one or more legs.

In one embodiment, an implantable sensor module is provided, comprising a proximal anchor with one or more barbs oriented such that the sensor module can be pulled proximally through an opening in a septal wall, but such that the barbs prevent the module from being pushed distally through such opening. In one embodiment, the barbs comprise angled metallic tabs.

In one embodiment, an implantable pressure sensor module is provided, wherein the module comprises a hermetically sealed pressure transducer module configured to be supported by the proximal and distal anchors. The proximal and distal anchors of this embodiment are configured to be movable between a collapsed delivery position and an expanded position in which the proximal and distal anchors secure the module to a wall of an organ within a patient. Said implantable pressure sensor module wherein the forward orientation of the distal anchors legs project distally beyond the pressure-sensing diaphragm, and protect the diaphragm from being damaged during handling or catheter passage into the body.

In one embodiment, a system for diagnosing and/or treating a medical condition in a patient is provided, using a device to measure pressure comprising a pressure-sensing module configured to be implanted within a patient, a proximal anchor comprising at least one helical leg configured to expand from a compressed state to a relaxed state, and a distal anchor comprising at least one leg configured to expand from a compressed state to an expanded state. In one embodiment, said proximal anchor and said distal anchor are configured to sandwich an atrial septum wall (or the left atrial free wall, the pulmonary vein wall, or any other suitable wall of a heart or a blood vessel) between the proximal anchor leg and the distal anchor leg and to support the module in the septum wall. In one embodiment, said system further comprises a delivery system, such as a catheter, configured to deploy the sensor, the proximal anchor and the distal anchor in the septum wall.

In one embodiment, a system for monitoring a patient for congestive heart failure is provided, comprising an implantable pressure transducer and a means for contacting a proximal side or wall and a distal side or wall of an organ to anchor said pressure transducer to the organ wall. Said system for monitoring a patient for congestive heart failure may further comprise a means for delivering said implantable transducer and means for contacting to said organ wall.

In one embodiment, a method of monitoring congestive heart failure in a patient is provided, comprising providing a pressure sensor secured to a proximal anchor and a distal anchor, and delivering the pressure sensor through a hole in an atrial septum of the patient's heart. The method further comprises deploying the pressure sensor with the proximal anchor on a proximal side of the septum, and the distal anchor on a distal side of the septum, and monitoring a fluid pressure in the left atrium of the patient's heart.

In one embodiment, a method of monitoring congestive heart failure within a patient is provided, comprising providing an implantable pressure transducer and coupling said implantable pressure transducer to a means for anchoring said pressure transducer in an organ wall. The method may further comprise delivering said pressure transducer and said means for anchoring to said organ wall, and causing said means for anchoring said pressure transducer in said organ wall to expand, thereby capturing said organ wall and anchoring said pressure transducer thereto.

In one embodiment, a method of anchoring a device in the heart of a patient is provided, comprising providing an implantable cardiac anchoring device comprising a proximal anchor having at least one helical leg and a distal anchor having at least one linear leg, attaching an implantable pressure-sensing module to the implantable cardiac anchoring device, positioning a tubular delivery catheter in a wall of a patient's heart, and inserting the implantable module and the implantable cardiac anchoring device into the tubular delivery catheter. The method further includes deploying the sensor and the implantable cardiac anchoring device such that the sensor is retained in a transverse orientation relative to the wall.

In one embodiment, an implantable sensor module is provided, comprising a substantially cylindrical body connected to the distal end of a lead, and a lead-attachment interface comprises a series of annular notches which can be engaged by a tightly-wound coil. The lead-attachment mechanism can be welded in place, such as by laser welding, on the sensor. The lead-attachment interface can comprise screw threads.

In one embodiment, an implantable sensor module having a substantially cylindrical body is provided, to which is attached a distal anchor assembly, wherein the distal anchor assembly is secured to the sensor by struts or locking tabs on the anchor, which engage an angled annular groove which circumscribes a distal portion of the sensor, and comprises locking tabs extending distally from the distal anchor that are bent slightly radially inwards such that they will engage the distal annular groove in the sensor.

In one embodiment, an implantable sensor module having a substantially cylindrical body is provided, to which is attached a proximal anchor assembly, wherein the proximal anchor assembly comprises locking tabs configured to engage a proximal annular groove in the sensor module body.

In one embodiment, an implantable sensor module having a substantially cylindrical body is provided, to which is attached a proximal and/or distal anchor assembly, wherein the proximal and/or distal anchor assembly is secured to the sensor by struts or locking tabs on the anchor, which engage an angled annular groove which circumscribes a proximal and/or distal portion of the sensor, and wherein the proximal and/or distal anchor tabs are spot-welded to their respective annular flanges to prevent rotation of the anchors relative to the sensor module.

In one embodiment, an implantable sensor module having a substantially cylindrical body is provided, to which is attached a proximal and/or distal anchor assembly, wherein the proximal and/or distal anchor assembly is secured to the sensor by struts or locking tabs on the anchor, which engage angled notches that receive the locking tabs in a single rotational orientation on the sensor, effectively preventing rotation of the anchors with respect to the module.

In one embodiment, an implantable sensor module with a distal sensor membrane and a distal anchor is provided, wherein the distal anchor is configured to position the plane of the sensor membrane at a predetermined distance from the plane of the distal anchor. In one embodiment, the distance is preferably zero, i.e., the pressure-sensing face is preferably substantially co-planar with the distal-most point of a deployed distal anchor. In alternative embodiments, the sensor is moved distally such that the pressure-sensing face extends distally outwards from the distal anchor. Alternatively still, the sensor is supported within the distal anchor such that the sensor face is recessed within the distal anchor. The location of the sensor face relative to the distal anchor is varied by changing the location of the distal annular groove and/or by varying a size of the locking tabs.

In one embodiment, an implantable sensor module having a substantially cylindrical body is provided, said module having proximal and distal anchor assemblies, wherein the components are attached to one another with interlocking mechanical fasteners. The proximal anchor, the distal anchor, and the sensor may include interlocking structures configured to mechanically interconnect the assembly components in such a way as to limit both axial and rotational movement of the components relative to one another. The distal anchor comprises a plurality of fingers that extend proximally from the cylindrical base portion, each finger comprising a narrow neck section and a wider proximal tab section. The proximal anchors may comprise correspondingly shaped slots in the distal ring to receive the fingers of the distal anchor. The sensor also includes corresponding interlocking structures configured to engage structures on the distal and/or proximal anchors.

In one embodiment, an implantable sensor module having a substantially cylindrical body is provided, said module having proximal and distal anchor assemblies, wherein the sensor includes raised sections around the circumference of the cylindrical body positioned so as to leave gaps for receiving the neck sections of the fingers, providing a secure and substantially immobile connection between the proximal anchor, the sensor, and the distal anchor. The raised sections are machined into the cylindrical body of the sensor. The raised sections comprise independent segments welded, adhered, or otherwise secured to the cylindrical body of the sensor. The interlocking structures may also be welded together once they are assembled, thereby further securing the connection.

In one embodiment, one or more radiopaque markers are used in conjunction with deployment of the physiological sensor. In one embodiment, radiopaque markers can be applied to the legs of the distal anchor. In one embodiment, radiopaque markers can be applied to the proximal ring of the proximal anchor. In one embodiment, radiopaque markers can be applied to other portions of the proximal or distal anchors, or on the sensor. In one embodiment, radiopaque markers are preferably placed in "low flex zones," such as the tips of the distal anchor legs and the proximal ring of the proximal anchor. In one embodiment, radiopaque markers are made of noble metals, such as gold, platinum/ iridium, tantalum, etc. In one embodiment, radiopaque markers are attached to the anchor by selective plating or ion beam deposition. In one embodiment, radiopaque markers could be micro rivets and/or rings that are mechanically attached to portions of the system components. In one embodiment, the radiopaque material can be selected to have a galvanic corrosion potential that is substantially similar to a galvanic corrosion potential of the material from which the anchors and/or sensor are made. If the anchors are to be made of nitinol, the radiopaque markers can be made of tantalum. In one embodiment, an electrically insulating coating (conformal coatings) such as parylene or other biocompatible synthetic material can be used to cover the radiopaque markers in order to isolate the marker and anchor section from exposure to the blood or other bodily fluid.

Several embodiments of the present invention provides these advantages, along with others that will be further understood and appreciated by reference to the written disclosure, figures, and claims included herein.

BRIEF DESCRIPTION OF THE DRAWINGS

The structure and operation of the invention will be better understood with the following detailed description of embodiments of the invention, along with the accompanying illustrations, in which:

FIG. 3 is a perspective view of one embodiment of a proximal anchor in a compressed state.

FIG. 4 is a perspective view of the proximal anchor of FIG. 3 in an expanded state.

FIG. 5 is a side view of the proximal anchor of FIG. 4.

FIG. 6 is a front view, looking proximally at the proximal anchor of FIG. 5.

FIG. 7 is a front view, looking proximally at a distal anchor and a sensor mounted to the distal anchor.

FIG. 8 is a cross-sectional view of the distal anchor and sensor of FIG. 7 taken through line 8-8.

FIG. 9 is a detail view of a portion of the distal anchor and sensor of FIG. 8, taken at line 9-9.

FIG. 10 is a perspective view of one embodiment of an assembly of a proximal anchor, a distal anchor, and a sensor.

FIG. 11 is a detail view of a portion of the assembly of FIG. 10, taken through line 11-11.

FIG. 12 is an exploded view of the proximal anchor, distal anchor and sensor of FIG. 10.

FIG. 15 is a perspective view of a delivery catheter with a portion of a distal anchor visible at the distal end of the delivery catheter.

FIG. 16 is a perspective view of the assembly of FIG. 15 shown with the delivery catheter removed to show detail.

FIG. 17 is a perspective view of a distal anchor and a sensor deployed on a distal side of an atrial septum wall.

FIG. 26 illustrates various embodiments of the distal anchor legs.

FIGS. 27A to 27C depict deployment of one embodiment of the distal anchor legs.

FIG. 28 is a perspective view of the distal anchor legs from FIG. 27C.

FIGS. 29A and 29B are perspective views of the distal anchor legs from FIG. 27C.

DETAILED DESCRIPTION OF THE PREFERRED EMBODIMENT

Figure 1:
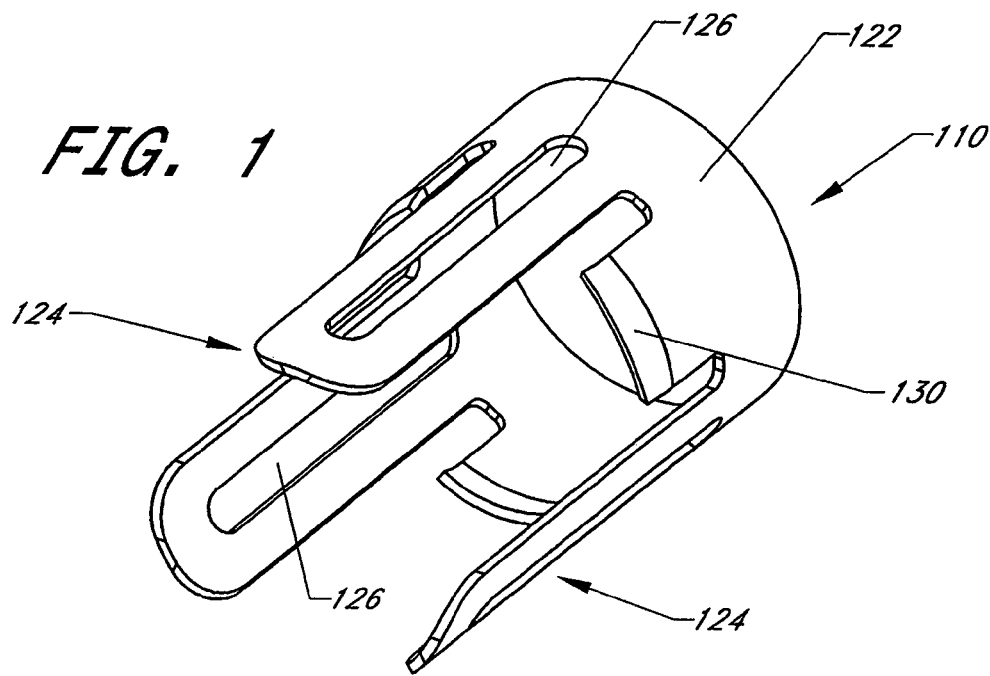
FIG. 1 is a perspective view of one embodiment of a distal anchor in a compressed state for deployment in a patient.

Several embodiments of the present invention relate generally to implantable physiological sensors. Physiological sensors include, but are not limited, to pressure sensors. In one embodiment, a pressure transducer system that is stable following implantation in the medical patient is provided. The sensors and methods described in some of the embodiments are designed for optimal healing and stability of implanted sensors. Several embodiments of the current invention are advantageous because they reduce the risk of thrombus formation. Other embodiments minimize tissue overgrowth that causes pressure sensor drift. Other embodiments of the invention are designed to isolate the sensor diaphragm from stresses in the tissue surrounding the sensor assembly. Other embodiments of the invention are designed to optimize performance. In one embodiment, deployment devices and/or anchoring means are provided integral to or accompanying the sensor. In a further embodiment, the sensor is enclosed in protective packaging. In another embodiment, the sensor is designed to minimize viscoelastic drift. In yet another embodiment, temperature compensation is provided. In a further embodiment, the effects of pressure waveform artifacts due to non-pressure mechanical forces (e.g. "side loading"), are minimized.

Implantable Device Thrombosis and Tissue Overgrowth

Transmural placement of traditional physiologic sensing apparatuses, particularly for the measurement of cardiac chamber or vascular pressures, have a number of limitations that affect long term reliable sensing and may promote serious complications. One area of particular concern is the placement of these devices through the walls of the heart to contact the blood contained in the left atrium or adjacent regions of the left-side of the heart. These devices can activate thrombus formation (blood clots, mural thrombi) on their exposed surfaces or over adjacent injured tissue. Left-sided thrombi have the potential to embolize to arteries of the systemic circulation causing catastrophic complications such as cerebral vascular accidents (stroke) and embolic infarctions of other vital organs.

Several embodiments of the present invention are designed to accommodate for the long-term presence of a device in the left atrium and its attendant risk of thromboembolic events, including stroke. In some embodiments, the surface properties of the device, such as its material constituents and its roughness, the size of the device, and/or the shape of the device are designed to minimize the risk of thromboembolic events. In one embodiment, a pressure transducer system having a relatively small surface area is provided. This embodiment is particularly advantageous because a smaller surface area accelerates healing and decreases the chance of clot formation on the device or adjacent injured wall.

Severe local tissue injury and inflammation promotes thrombus formation. Clots can form as platelets are activated in regions of high blood shear rate or where fibrin is deposited in regions of stasis, classically in the presence of atrial fibrillation. Also, the overall prothrombotic state of the patient is important. Accordingly, in several embodiments, appropriate pharmacologic prophylaxis, including, but not limiting to antiplatelet, antithrombin, and/or antiproliferative drugs, are administered before, during, and/or after implantation of the sensor. In one embodiment, pharmacologic treatments are used to accelerate or facilitate coverage of the device with new tissue growth (overgrowth), which is referred to as a neoendocardium in the case of the heart or a neointima in the case of a blood vessel. As used herein, the terms neoendocardium, neointima, tissue overgrowth, tissue in-growth are used interchangeably. Once tissue overgrowth occurs there often develops a new lining of cells that normally form the blood tissue interface call a neoendothelium. Generally, a functional neoendothelium reduces the risk of an underlying implanted device generating mural thrombus.

In several embodiments of the current invention, one or more of the following factors is addressed in order to decrease the risk of thrombus formation: a rough implant surface, the extent of adjacent tissue injury, interruption of laminar blood flow during deployment, high shear rate of the blood contacting the implant, local blood stasis, and delayed coverage of the device by body tissues.

According to our own studies with stents, we have observed that when a relatively a rough metallic surface (bead blasted nitinol or 316 L stainless) is exposed to rapid blood flow with a high shear rate, exaggerated platelet activation and aggregation are triggered resulting in the formation of platelet-rich thrombi. Accordingly, in several embodiments, at least a portion of the metallic surface of the device is electropolished to reduce the risk of acute thrombosis. In one embodiment, the entire metallic surface is electropolished. In another embodiment, chemical, mechanical, and/or sonic treatments, including, but not limited to passivation and oxygen cleaning, are used to achieve similar effects to electropolishing.

Stent studies have also shown that thrombosis is most likely during the first two to three weeks after implantation until a neoendothelium is present. Further, when tissue overgrowth is delayed or prevented, such as by treatment with intravascular radiation therapy (brachytherapy) at the time of implantation, there is an increased risk for delayed thrombosis (months later). Accordingly, in several embodiments of the present invention, antiplatelet agents are administered to the patient to reduce the risk of thrombosis. In one embodiment, aspirin and/or clopidogrel, are administered to reduce the incidence of thrombosis.

Although not wishing to be bound by the following theory, it is believed that as soon as the device's appropriate surface is covered by an overgrowth of proliferating tissue (neointima), especially when the neointima contains a blood lining barrier of cells called a neoendothelium, the risk of thrombosis is substantially reduced or essentially eliminated. Tissue overgrowth is the natural healing response to local vascular mechanical injury. The sequence of healing events include coverage of the device with plasma proteins such as albumen and fibrin during the initial hours to days, recruitment of blood mononuclear cells over the first week that signal vascular smooth muscle cells in the vessel wall to migrate to the lumen surface, proliferate, and secrete a proteoglycan extracellular matrix. One of the important signals for turning off smooth muscle cell proliferation is in-growth of vascular endothelial cells from adjacent, uninjured tissue. In several embodiments of the current invention, the device is designed to facilitate or accelerate tissue in-growth. In one embodiment, in-growth is enhanced by providing shallow channels on the surface of the device oriented in the direction of blood flow to aid this migration. In some embodiments, complete coverage should take about 2 to 3 weeks, and the rapidity of this overgrowth is desirable because it lowers the risk of thromboembolism and shortens the need for adjunctive antiplatelet medication.

Tissue thickness tends to reach a maximum after about 4 to 6 months, averaging about 300 to 400 microns thick depending on the stent and study. When this thickening encroaches on the vessel lumen causing luminal narrowing of more than 50% of the vessels reference diameter, it is called restenosis. After the first 6 months, the extracellular matrix is gradually replaced by collagen and the tissue distribution may change (remodeling) but generally the tissue remains intact and stable for many years thereafter. The tissue remains pliable and only rarely, if ever, becomes atherosclerotic or calcified. The maximal thickness of tissue overgrowth is highly variable but is well known to depend on and a variety of host risk factors, such as diabetes and smaller vessel size. Tissue thickness also depends on mechanical factors including the extent of tissue injury and device design characteristics. In one embodiment of the present invention, the pressure transducer system is designed to have a lower profile or less strut protrusion into the blood stream, thereby promoting a thinner covering of neointima. In other embodiments, the sensor system is designed to develop a thin layer of neointima that provides remodeling benefits to reduce turbulent bloodflow about the sensor system.

Several embodiments of the present invention provide a physiological sensor system that is constructed from a material that is minimally reactive, stable, and that promotes a favorable healing response. Several embodiments of the present invention are particularly advantageous because they minimize thrombotic potential, promote rapid tissue coverage, heal without chronic inflammation, and/or develop a thin neointima with beneficial remodeling features. Other advantages of some embodiments include sensor reliability and accuracy, positioning stability and clinical efficacy for diagnosing and directing therapy in chronic CHF. In one embodiment, the sensor system comprises one or more of the following materials: alloys of stainless steel, nitinol, titanium, cobalt chromium, and tantalum. One skilled in the art will understand that several other biocompatible materials may be used. These materials are typically minimally reactive or non-reactive. Using minimally reactive or non-reactive materials is particularly advantageous because they are hemocompatible and do not promote an inflammatory tissue reaction, known to pathologists as a foreign body reaction, consisting of granulomas containing macrophages and giant cells. This type of tissue reaction may be associated with higher thrombotic complication rates, more exuberant tissue proliferation and thickening, calcification and possibly even late tissue breakdown and delayed exposure of bare reactive surfaces to blood once again promoting thrombus formation.

In some embodiments, the implantable sensor system will be operable to elute one or more drugs that affect neointimal tissue thickness or thrombosis risk. In some embodiments, a component of the sensor will elute the drug. In an alternative embodiment, a separate device, administered in conjunction with the sensor, will elute the drug. In one embodiment, antiproliferative drugs, such as from biostable or bioerrodable polymeric coatings (including, but not limited to, sirolimus and paclitaxel) are used to control neointimal tissue thickness and virtually eliminate restenosis. In some embodiments, pharmacologic treatment will reduce tissue thickness by more than 50%, to an average of about 120 microns. In certain embodiments of the invention, more precise control of drug delivery is desired because high drug doses may in some cases create toxic reactions or prevent any effective tissue coating and increase the likelihood of late (after three weeks) stent thrombosis. Accordingly, in several embodiments of the present invention, low doses of one or more of these drugs eluted over longer periods are provided. The skilled artisan will understand that while reduced neointimal thickness may be desirable, it is desirable for implant surfaces in contact with blood be covered with at least a thin layer of endothelial cells. One skilled in the art will understand that endothelial cells grow over the surface of an implanted surface from its contact with existing tissue. In one embodiment, one or more pathways or channels are provided to encourage the ingrowth of endothelial cells while reducing neointimal thickness. In one embodiment, anti-thrombotic compounds are eluted from the implanted device. Elution of anti-thrombotic compounds may be used as a bridge to reduce the thrombosis risk until such time the device can develop a neoendocardium covering.

One skilled in the art will understand that an antiproliferative and/or antiplatelet drug regimen can be adjusted to the type of sensor implanted, the location of the implant, and the condition of the patient, and other factors. For example, pharmacologic treatment can be administered in accordance with U.S. Pat. No. 6,152,144 (Lesh) and U.S. Pat. No. 6,485,100 (Roue et al), herein incorporated by reference, which describe permanently implanted devices placed in the left atrium to repair transmural congenital defects of the intra-atrial septum. In one embodiment of the present invention, thromboemboli are prevented with antiplatelet therapy consisting of about six months of aspirin therapy. In one embodiment, aspirin therapy is augmented with a second antiplatelet agent, such as clopidogrel, for approximately the first three months.

In one embodiment of the invention, the sensor system is designed to minimize tissue erosion that may be related to mismatching of the elasticity of the anchoring portions versus the surrounding tissue. It is well known to those skilled in the art that orthopedic prostheses that differ significantly in elasticity from bone produce stress shielding of the bone, resulting in its weakening and producing problems with the prostheses. It is also well known to skilled artisans that soft tissue prostheses such as fabric patches and tubes used in vessel replacement and repair are best tolerated when their elasticity is similar to that of the surrounding tissues to which they are attached. In one embodiment, the elasticity mismatch of the sensor system and the surrounding tissue can be assessed by calculating the difference in the elastic modulus ($dyn/cm^2$) between the sensor system material and the surrounding body tissue at a given pressure. The elastic modulus can be measured by calculating the change in stress over the change in strain of a given material or tissue.

Several embodiments of the current invention are designed to treat CHF. CHF patients have a high incidence of thromboembolic stroke in part because they have a high frequency of known risk factors for left atrial thrombi including: generally enlarged and diseased left atria; mitral valve disease with mitral regurgitation is present in 50%; about 80% of patients are age 65 or older; about one third have atrial fibrillation; atherosclerosis, diabetes and hypertension are also very common. Thromboembolic events typically, but not always, result from the interaction of multiple risk factors. Accordingly, several embodiments of the invention are particularly advantageous for CHF patients because they minimize the incidence of a thromboembolic event by providing an implantable device with reduced thrombogenic effect. Moreover, in accordance with some embodiments of the present invention, a transmurally implanted left atrial pressure transducer device that promotes rapid healing with non-thrombogenic tissue overgrowth is highly desirable for preventing additional thromboembolic complications associated with the implanted devices in patients with CHF.

Several embodiments of the present invention comprise one or more anchors, described below, to affix the sensing device to tissue. To hasten and optimize tissue overgrowth, one embodiment minimizes the path lengths for tissue to in-grow over the distal anchor fixated to the left atrial side of the septum by creating slots or holes in the distal anchor legs. In one embodiment, within several weeks after implantation, the entire device is covered with new tissue, including precursor fibrous tissue and endothelium. A covering of endothelium is desirable because it prevents the formation of blood clots that, if formed, could break loose and cause a blocked artery elsewhere in the body, most dangerously in the brain. A covering of fibrous tissue is also a common component of the body's healing response to injury and/or foreign bodies. In another embodiment, a biocompatible polymeric coating such as parylene is placed on the fixation anchors and diaphragm to minimize platelet adhesions and aggregation, to provide electrical insulation, and to prevent corrosion of underlying metallic constituents. In yet another embodiment, surface grooves or channels are used in at least a portion of the implant to facilitate tissue growth. In one embodiment, at least one groove can be formed on the diaphragm surface or on the anchor legs to serve a similar purpose. The groove's long axes can be linear, circumferential, and serpentine or any other beneficial shape and the groove's cross section can be rectangular, semi-round, or any other beneficial shape. In one embodiment, the grooves, wells, or portions or all of the exposed surfaces are filled with or coated by biostable or bioerrodable polymer or polymers containing agents, including one or more drugs that control the thickness of neointimal tissue overgrowth, or prevent local thrombus formation.

Although tissue overgrowth of the implanted pressure sensor can reduce the thrombosis risk posed by the device, an excessive growth of fibrous tissue on the left atrial surface of the pressure sensor may be undesirable because it may interfere with accurate transmission of fluid pressure in the left atrium to a relatively compliant diaphragm. In addition, uneven contraction of fibrous tissue over time may cause artifactual changes in the pressure waveform, which could confound interpretation of the data. In one embodiment, a coating on the diaphragm surface and or the anchor surfaces inhibits or reduces the formation of undesirable fibrous tissue, while not preventing the beneficial growth of an endothelial covering. Coatings with these properties are well known in the art of implanting medical devices, particularly intravascular stents, into the blood stream. Surface coating materials include, but are not limited to, parylene, polyvinylpyrrolidone (PVP), phosphoryl choline, hydrogels, albumen, polyethylene oxide and pyrolyzed carbon. In another embodiment, parylene is placed on the fixation anchors and diaphragm to minimize platelet adhesion and aggregation, to provide electrical insulation, and to prevent corrosion of underlying metallic constituents.

In one embodiment, at least some areas of the sensor package and diaphragm are electropolished. Electropolished surfaces are known by those skilled in the art to reduce the formation of thrombosis prior to endothelialization, which helps prevent device thrombosis and leads to a reduced burden of fibrotic tissue upon healing. Metallic intracoronary stents currently approved for clinical use are electropolished for this purpose.

Release of antiproliferative substances, including radiation and certain drugs, are also known to be effective in limiting tissue overgrowth after vascular stenting. Such drugs include, but are not limited to, Sirolimus, Everolimus, Tacrolimus and related antirejection compounds, Taxol and other Paclitaxel derivatives, corticosteroids, anti-inflammatory anti-macrophage agents such as 2-chlorodeoxyadenosine (2-CDA), antisense RNA and ribozymes targeted to cell cycle regulating proteins and other targets, and other cell cycle inhibitors, endothelial promoting agents including estradiol, antiplatelet agents such as platelet glycoprotein IIb/IIIa inhibitors (ReoPro), anti-thrombin compounds such as unfractionated heparin, low-molecular weight heparin, hirudin, hirulog, etc., thrombolytics such as tissue plasminogen activator (tPA). These drugs may be released from biodegradable or biostable polymeric surface coatings or from chemical linkages to the external metal surface of the device. Alternatively, a plurality of small indentations or holes can be made in the surfaces of the device or its retention anchors that serve as depots for controlled release of the above mentioned antiproliferative substances, as described by Shanley et al. in U.S. Publication No. 2003/0068355, published Apr. 10, 2003, incorporated by reference herein.

Affects of Tissue Growth on Pressure Sensor Calibration

As described above, tissue overgrowth is desirable to reduce the incidence of thrombosis. Although tissue overgrowth has clear benefits, it may also pose some challenges for implanted pressure sensors because the overlying tissue can be a major source of drift, thereby causing the transducer to lose calibration. For example, calibration issues can occur with an implanted pressure transducer that relies on the displacement of an exteriorly exposed mechanical member, such as a membrane or diaphragm, that actuates protected internal components such as piezoresistive strain gauges or other types of transducers that generate a signal related to the pressure change. For transducers that have a linear relationship between the pressure change and the transducer output and to the extent that tissue overgrowth interferes with the displacement of the mechanical member in response to a given pressure change, the sensitivity or "gain" (slope) of the transducer output/input relationship will be reduced or drift. Likewise, if tissue coverage causes displacement of the mechanical member, errors or drift in offset or "zero" (y-intercept) will occur. When these tissue effects cause errors in physiologic pressure measurement that affect diagnosis and treatment decisions, the transducer requires recalibration. Transducers that have non-linear calibration relationships will also be affected by tissue overgrowth and experience drift.

The process of tissue coverage is generally dynamic. As healing takes place the thickness of tissue increases over about 4 to 6 months; thereafter, the thickness may gradually decline or increase (remodel) over the next several years. In addition to tissue thickness effects on drift, the biochemical constituents of the tissue change as the matrix material is replaced with collagen and may have different material properties such as elasticity, that may further contribute to transducer drift.

Recalibration of implanted pressure transducers is typically performed by comparison with a calibrated standard. This most often has meant that the patient is required to undergo periodic invasive catheterization procedures. Thus, in several embodiments of the present invention, a pressure transducer with calibration parameters that are minimally affected by tissue overgrowth, thereby reducing the need for invasive recalibration, is provided. These embodiments are advantageous because they do not subject the patient to the risk, discomfort, and expense of such procedures. In some embodiments, a pressure transducer that promotes reduced but effective tissue overgrowth is provided. This is desirable because it reduces the risk of thromboembolic complications. Typically; if tissue overgrowth causes an essentially linear sensor to drift with respect to both gain and offset, recalibration against a standard at a minimum of two different pressures is required. A pressure sensor that drifts with respect to offset only may be more simply recalibrated against a standard at a single pressure only. Accordingly, several embodiments of the present invention provide pressure transducers that either do not require calibration or can be easily recalibrated using non-invasive methods. Methodology and apparatus to non-invasively assess implanted transducer calibration and automatically recalibrate has been described in U.S. Patent Application Publication No. US 2004/0019285 A1, herein incorporated by reference.

Protective Packaging

Electronic and mechanical devices are frequently placed in environments that may damage the components unless some form of protection is provided. For example, some electronic medical devices implanted into a body may be exposed to body fluids that may cause unprotected semiconductor circuits and non-electronic components to fail. Accordingly, in several embodiments of the current invention, at least a portion of the sensor system is protected against the damaging effects of bodily fluids. In one embodiment, the device is contained in hermetic packaging to limit exposure to these harmful elements.

In some embodiments, a traditional approach to creating protective packaging for implantable medical devices is used. This generally involves the complete encasement of the silicon or semiconductor components of the device in a hermetic package. Such packages typically utilize a metal such as titanium, or a ceramic material like alumina or zirconia. Various glass materials can also be employed. In other embodiments, the sensor is enclosed in a metal packaging and the environmental pressure is coupled to the sensor through a diaphragm bonded to the packaging. Such approaches place an interface between the environment and the sensor for the electronic components to interact with the environment and to protect the integrity of the device. Such a diaphragm can be made from the same or similar materials as the housing to facilitate bonding and hermetic sealing of the diaphragm with the housing or protective barrier of the device. Further methods of hermetic sealing are described below.

Delivery and Deployment of the Pressure Transducer

Additional embodiments that enhance or optimize the transmurally implanted transducer's capabilities are provided. With respect to deployment apparatus and methodology, in one embodiment, the transducer module is delivered to its desired location by a catheter or sheath that transverses the wall of the desired chamber or vessel and can be loaded with the transducer module system with its fixation anchors in a constrained or folded configuration. In another embodiment, the delivery catheter permits simultaneous measurement of fluid pressure from the catheter tip during transducer package transit and deployment. In a further embodiment, the delivery catheter permits injection of radiographic contrast material with the transducer system in its lumen to localize positioning during transducer system deployment. In another embodiment, the transducer module and/or its fixation anchors have radiographic markers to enhance visualization during deployment.

Viscoelastic Drift

In several embodiments of the instant invention, the pressure transducer is optimized for assuring performance and minimizing complications. In one embodiment, the transducer is designed such that viscoelastic drift is minimized. After prolonged exposure to a large change in average ambient pressure, such as the change to lower pressures during travel to high altitude, some pressure transducers undergo viscoelastic drift whereby their components undergo elastic deformation with prolonged time constants lasting hours to days or more before returning to the pre-stressed state. This phenomenon may result in a baseline shift that persists until another large change in average ambient pressure sets into motion another viscoelastic drift to another new baseline. In one embodiment of the present invention, the viscoelastic properties of the pressure transducer are characterized during pre-implant calibration. In one embodiment, the known viscoelastic properties are used in combination with the recorded pressure variations over time to obtain pressure measurements that are corrected for viscoelastic drift.

Figure 22:
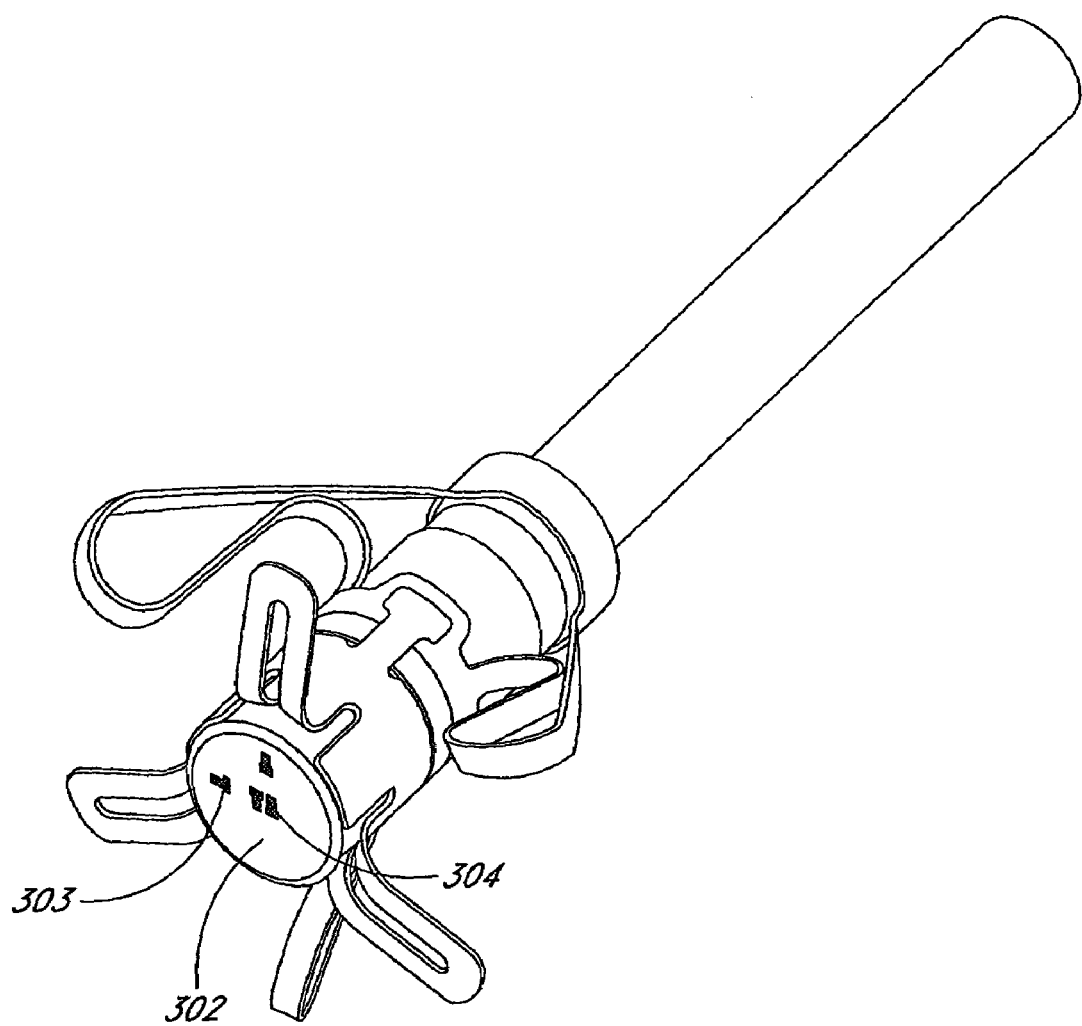
FIG. 22 is a schematic view of an implantable transmural pressure sensor.

In one embodiment, the diaphragm has a plurality of resistive strain gauges coupled to the diaphragm's internal surface. In one embodiment, shown in FIG. 22, the diaphragm 302 has two or four resistive strain gauges 303, 304 adhered to the diaphragm's internal surface by an adhesive. The adhesive normally serves two purposes: i) fixation of the strain gauges to the diaphragm and ii) electrical insulation of the strain gauges to prevent a short circuit to the case. In one embodiment, to accomplish the latter, the adhesive is of a thickness that is substantial enough to exhibit some viscoelastic displacement in response to a change in the shape of the diaphragm, resulting in transducer drift in response to large prolonged change in average pressure, such as occurs when the patient travels to a much higher or lower altitude. In one embodiment, a silicon dioxide insulation layer is grown on the bottom of the silicon strain gauges providing additional electrical isolation and consequently minimizing the thickness of adhesive and resulting viscoelastic drift.

In another embodiment, a software algorithm is used to automatically correct for viscoelastic drift. In another embodiment, a secondary diaphragm may be located on other portions of the module. In one embodiment, a secondary diaphragm is used to measure pressure at a second site or to measure a differential pressure between the distally located diaphragm and the secondary diaphragm. In one embodiment, the second diaphragm may be used to provide additional calibration information for the first diaphragm, and/or vice versa.

Figure 24:
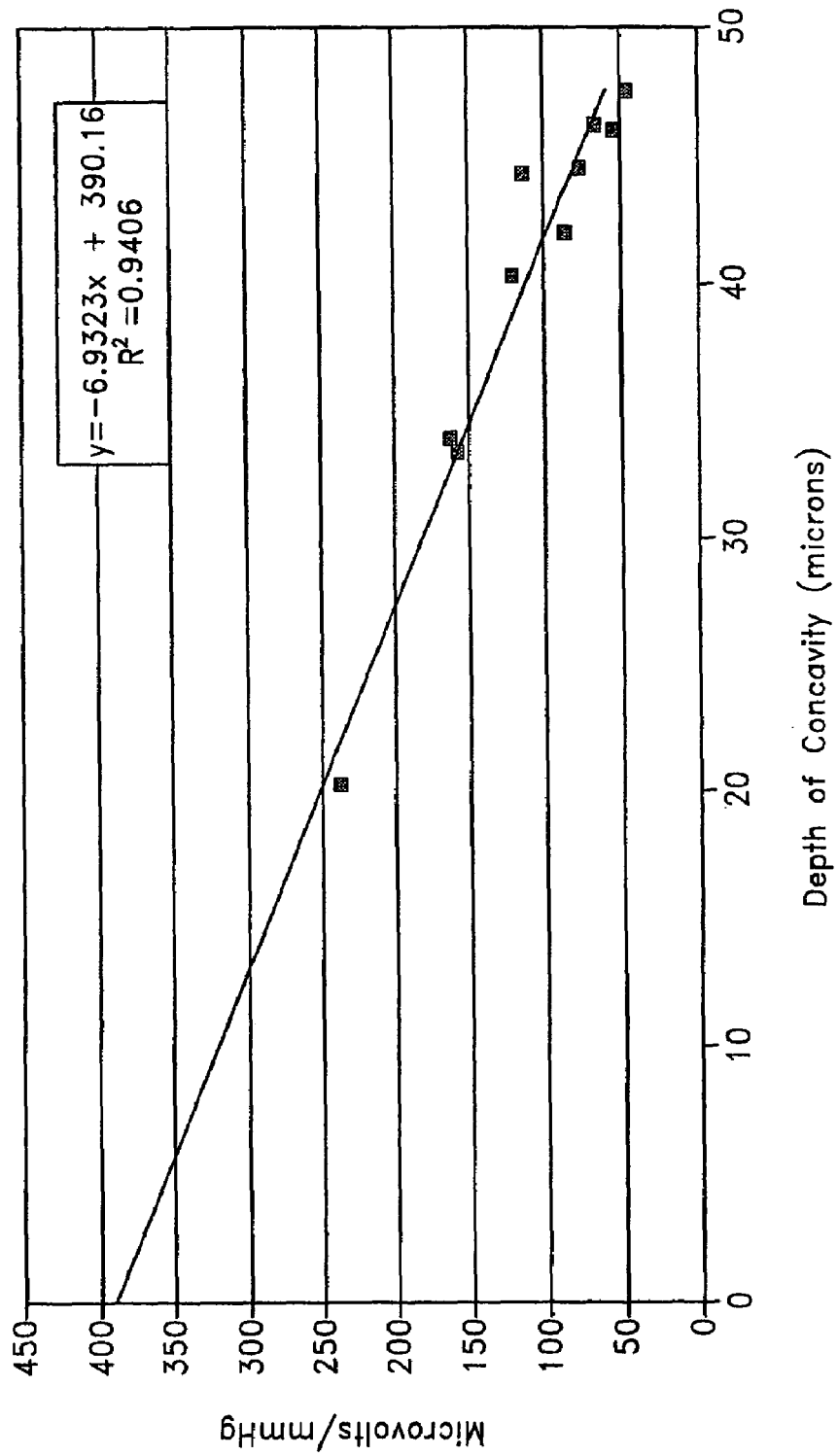
FIG. 24 shows the results of an experiment evaluating the effect of diaphragmatic concavity (depth of a central concavity) in a 25 micron thick, 2.5 mm diameter titanium foil membrane on transducer sensitivity (gain).

FIG. 24 shows the results of an experiment evaluating the effect of diaphragmatic concavity (depth of a central concavity) in a 25 micron thick, 2.5 mm diameter titanium foil membrane on transducer sensitivity (gain). These data suggest that the lesser the concavity (or convexity for that matter), that is, the flatter the diaphragm, the higher the gain. Accordingly, in one embodiment, a diaphragm that is both essentially non-compliant and essentially flat is used to minimize the effects of tissue overgrowth on reducing transducer gain (non-compliance), while optimizing intrinsic gain (flatness). In another embodiment, the diaphragm thickness is maximized to maximize flatness and minimize compliance, consistent with the sufficient compliance to derive a useable transducer signal.

Temperature Compensation

In one embodiment, the pressure sensor includes temperature compensation so that pressure measurements will be minimally affected or unaffected by temperature change. In one embodiment, apparatus to measure the temperature at the site of the sensor is provided. In one embodiment, temperature compensation or modulation is achieved by using multiple resistive strain gauges arranged in a Wheatstone bridge, such that the electrical voltage output of the bridge is proportional to the ratio of two or more resistances, as is well known in the art of electrical measurements. By selecting resistive strain gauges with substantially identical temperature coefficients, the intrinsic output of the bridge is made to be temperature independent. However, in one embodiment, the overall response of the pressure transducer may still be temperature dependent due to other factors, such as the different thermal expansions of the various components and contents of the device. Another embodiment of temperature compensation utilizes an internal thermometer comprising, for example, a resistor whose resistance depends upon temperature in a reproducible way, and which is placed in a location isolated from the transducer diaphragm so that its resistance does not depend on pressure variations. Prior to implanting the device, calibration data is collected consisting of the output of the transducer versus pressure as a function of the reading of the internal thermometer. After implantation, the signal from the internal thermometer is used together with the transducer output and the calibration data to determine the temperature compensated pressure reading. In one embodiment, a band gap voltage reference is used to create a current proportional to absolute temperature that is then compared to the temperature-independent voltage reference. Such methods are well known in the art of CMOS integrated circuit design.

Output Artifacts—Minimizing Effects of Side Loading

Another characteristic of some pressure transducers is that output artifacts can occur when structures adjacent to the mechanical members are stressed. Forces placed on the module casing that distort the mechanical diaphragm are known as side-loads. Side-loads exerted by tissue contact with the transducer module housing and/or its anchors, and/or forces exerted on the module by its lead, may produce non-pressure-signal artifacts in the output signal. Side-loads may develop during the healing process as tissues encroach on the side areas adjacent to the mechanical member supporting the pressure-sensing diaphragm, causing differential loading of said member. Accordingly, in one embodiment of the invention, the pressure transducer is designed to minimize output artifacts.

In one embodiment, the casing adjacent to the diaphragm is made substantially inflexible and non-distortable such that the diaphragm is not distorted by side-loads under physiologic conditions.

Figure 23A:
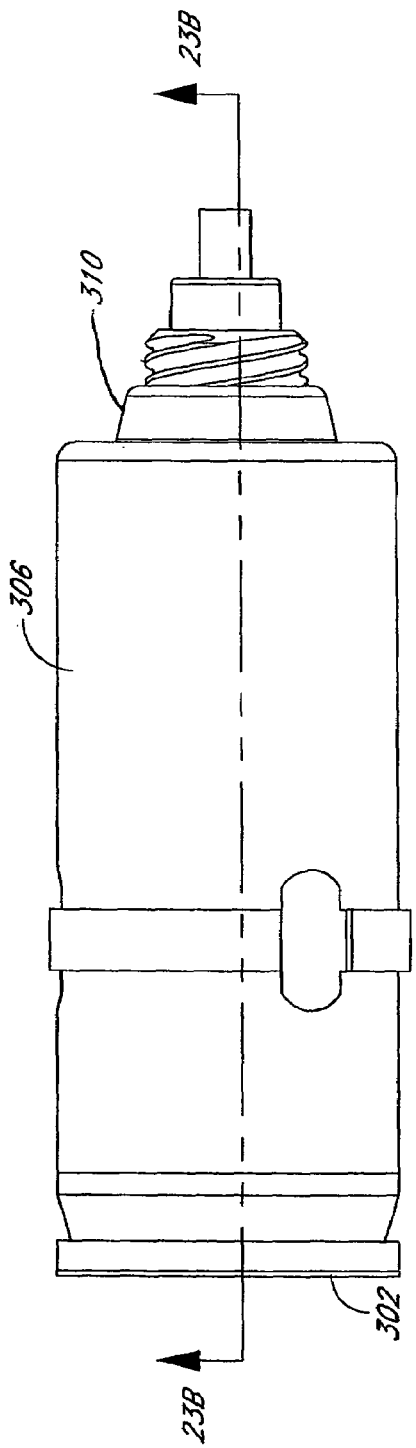
FIGS. 23A and 23B are elevational and cross sectional views of one embodiment of the implantable pressure sensor.
Figure 23B:
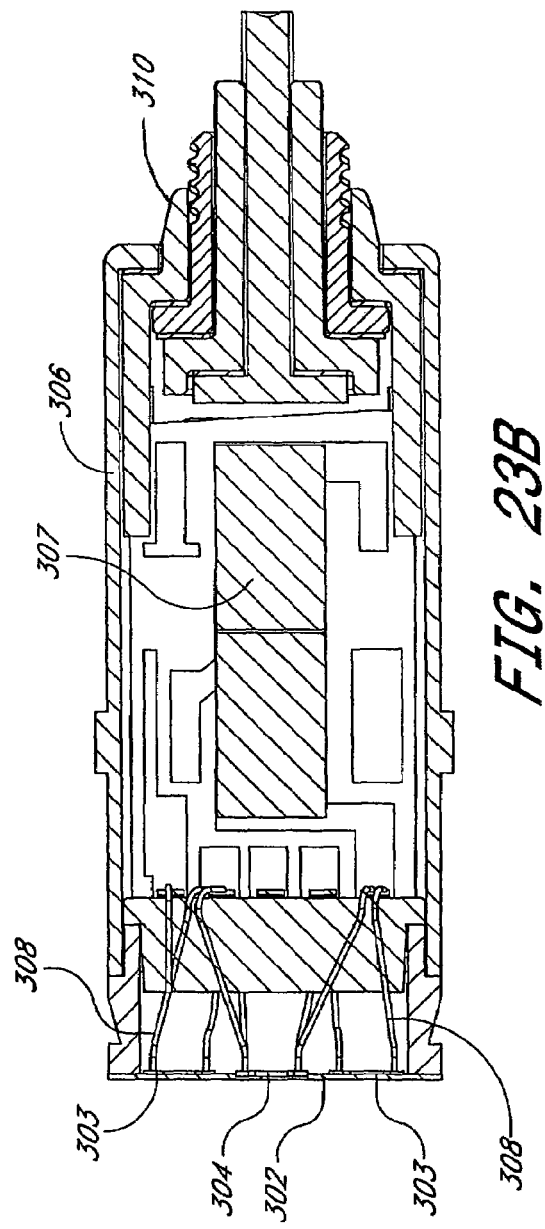

Another embodiment, shown in FIGS. 23A and 23B, comprises two sets of adherent strain gauges, an inner set 304 near the center of the diaphragm where tangential strain is relatively high and an outer set 303 near the periphery of the diaphragm where radial strain is also high but of opposite polarity. Electrically, this arrangement is connected to form a Wheatstone bridge circuit. In order to make the overall transducer relatively small, compromises are made on the supporting structure of the diaphragm. Because the supporting structure is not absolutely rigid, forces applied to the side of the structure will result in a small deformation of the diaphragm. The radial strain gauges are the most affected by this "side load." Prior art approaches to strain gauge mounting provide for the two radial strain gauges to be placed 180° apart. Side forces in line with these gauges would result in maximum signal change on the bridge since the effects are additive. Also side forces 90° from the radial strain gauge axis would produce another maximum but opposite polarity signal change on the bridge. In one embodiment of this invention, the radial strain gauges are oriented 90° from each other rather than the standard 180° orientation. This results in a partial canceling of the side load force effects, as the signal effects are substantially subtractive rather than additive. In this embodiment, the orthogonal arrangement of the radial strain gauges has been experimentally measured to reduce side loading effects on pressure readings by about two-thirds compared to when the radial gauges are affixed about 180 degrees apart.

In a further embodiment, the regions of the transducer module casing where the proximal and distal anchors are affixed are located as far proximal from the distal diaphragm as possible so that differential tension on the anchor legs causes less loading on the module casing near the diaphragm and thereby less distortion of the diaphragm than if the fixation regions were more distal and closer to diaphragm.

The skilled artisan will realize that various combinations of the embodiments described above may be beneficial. Therefore, a further embodiment represents any combination of the above embodiments, including increased casing wall thickness or rigidity, orthogonal placement of outer strain gauges, and/or proximal fixation of anchors utilized to increase pressure transducer insensitivity to side-loads.

Locations and Insertion Routes

In several embodiments, a physiological sensing device comprising implantable, transmurally-placed pressure transducer systems for measuring fluid pressure within a cardiac chamber or a blood vessel is provided. In one embodiment, the transducer system is implantable within any hollow viscous within the body of a medical patient. In one embodiment, the transducer system is optimized for placement in the left atrium of the heart by a percutaneous catheter-based procedure that traverses the intra-atrial septum. In another embodiment, the transducer system is optimized for placement in a pulmonary vein by an open surgical procedure.

As used herein, the terms "proximal" and "distal" are used to describe relative positions, locations and/or orientations of various components. As used herein, the term "distal" is used in its ordinary sense, and generally refers to objects and locations that are further along a trans-vascular path from an operator of a trans-vascular device. Similarly, the term "proximal" is used in its ordinary sense, and refers without limitation, to objects and locations that are closer along a trans-vascular path to an operator of a trans-vascular device. For example, in some embodiments the most proximal end of a catheter is the end that is operated by a clinician performing a procedure within a patient with the catheter. Similarly, in such embodiments the distal-most end of a catheter is the end placed furthest into the body of the patient and furthest from the clinician performing the procedure. The terms "proximal" and "distal" are used herein with reference to certain embodiments of the orientation of certain components during a procedure. The skilled artisan will recognize however, that in alternative embodiments the directions of "proximal" and "distal" as used herein may be reversed with respect to a single component used in a similar procedure.

Several embodiments of the current invention comprise permanently implantable transmurally-placed pressure transducer systems for measuring fluid pressure within a cardiac chamber or a blood vessel, or any other hollow viscous or fluid filled space within the body of a medical patient. The term "permanently implantable" as used herein shall be given its ordinary meaning and shall refers to any and all such devices that are intended for implanted for more than about one week and are therefore potentially or substantially permanent. In one embodiment, the transducer system is optimized for placement in the left atrium of the heart by a percutaneous catheter procedure traversing the intra-atrial septum. In another embodiment, the transducer system is optimized for placement in a pulmonary vein by an open surgical procedure. In yet another embodiment, the transducer system is optimized for placement through the free wall of the left atrium, or through the wall of the left atrial appendage, or across the right atrial free wall or right atrial appendage or transmurally into the main or branch pulmonary arteries by a minimally invasive thorascopic surgical procedure or by a traditional open surgical approach. Intrathoracic pressure may be monitored by placement of the pressure transducer system through the chest wall or diaphragmatic respiratory muscles by local puncturing techniques, under direct or fiberoptic endoscopic vision, or by robotic surgical manipulation. In one embodiment, output from an intrathoracic pressure transducer may be used to compensate for arterial pressure fluctuations caused by a patient's breathing rate and effort. In one embodiment, the intrathoracic pressure transducer can be used to validate and/or error check the operating status of other pressure transducers located in the thoracic cavity by comparing pressure tracings and checking for analogous respiratory fluctuations. In one embodiment, the intrathoracic pressure transducer is used to measure the respiratory efforts to assess respiratory status.

It will be apparent to those skilled in the art that transmural pressure monitoring refers in general to monitoring pressure anywhere in the body with a pressure transducer system that is placed through the wall of or traversing a septum, membrane or any other dividing structure that physically separates or represents a barrier or boundary of the location with the desired pressure to be monitored and other body structures. It will also be apparent that several methods of reaching the desired location can be used in accordance with several embodiments of this invention depending on the suitability of the specific anatomy to a particular method. These methods include, but are not limited to, catheter delivery, endoscopic delivery, minimally invasive surgery, and open surgery. One of skill in the art will understand that any location and transmural routes and methods of positioning implanted pressure transducer systems can be used in accordance with several embodiments of the present invention.

Pressure Sensor Designs

In one embodiment, the internal transducer components including the transducer, power, and communications components are enclosed in a hermetic casing or housing called a transducer module. In one embodiment, the casing comprises metal, ceramic, or glass, alone or in combination, or other constituents known to skilled artisans for constructing hermetic packaging. The transducer module has proximal and distal ends. Referring to FIG. 23B, in one embodiment, the distal end of the module comprises at least one hermetic diaphragm 302 designed to translate or flex in response to pressure changes at the desired location. In one embodiment, the diaphragm or membrane is mechanically coupled to enclosed transducer components.

In one embodiment, the enclosed transducer components comprise semiconductors that control power, pressure signal transduction, local signal processing, and data telemetry. In one embodiment, resistive strain gauges 303, 304 are bonded, or otherwise coupled, to the inside surface of the diaphragm 302. In one embodiment, a titanium cylindrical housing 306 comprises an application-specific integrated circuit (ASIC) 307 or "measurement electronics." Measurement electronics 307 are contained within the housing and electrically connected to the strain gauges by fine gold wires 308 or other means of electrical connection. In one embodiment, the proximal end of the housing is sealed by a zirconia ceramic feed-through 310 that is brazed to a titanium cylinder. In one embodiment, the housing contains a gaseous atmosphere. The gaseous atmosphere may comprise helium, argon, or any other advantageous gas or combination of gases known to skilled artisans. In one embodiment, the housing is evacuated prior to sealing. In another embodiment, an electrical insulating liquid such as an oil or other electrically insulating liquids known to skilled artisans is contained within the housing.

In one embodiment, the implanted module contains an internal power source, such as a battery. In another embodiment, the module is powered transcutaneously by induction of radio frequency current in an implanted wire coil connected directly to the module or connected by a flexible lead containing electrical conductors, to charge an internal power storage device such as a capacitor.

In one embodiment, the pressure transducer is contained within a hermetically sealed sensor package, or module. The sensor package may be provided in a wide range of sizes and shapes. In one embodiment, the sensor package is a cylindrical in shape with a distal end and a proximal end. In one embodiment, the module is between about 1 mm and 5 mm long, and 3 mm in diameter. In another embodiment, the module is between about 5 mm and about 15 mm long. In another embodiment, the package is about 8 mm long, and about 3 mm in diameter. In one embodiment, the package is less than about 1 mm in diameter. In another embodiment, the package is less than about 10 mm long. In one embodiment, the package may be rectangular, square, spherical, oval, elliptical, or any other shape suitable for implantation. In one embodiment, the sensor package is rigid, and in another embodiment, the sensor package is flexible.

In one embodiment, the sensor module includes a cylindrical housing comprising one or more component pieces of titanium CP, titanium 6-4, or other suitable biocompatible metallic alloy or other material suitable for making a hermetic package such as ceramic material like alumina or zirconia. Titanium pieces can be hermetically affixed to each other by laser welding and ceramic materials may be hermetically bonded to metallic components by brazing techniques. In one embodiment, the housing is closed at one end by a membrane called a diaphragm. In one embodiment, comprising a titanium cylindrical housing, the diaphragm comprises a titanium foil that is diffusion bonded or otherwise hermetically affixed to the titanium housing. In another embodiment, the membrane may be machined, lapped, or otherwise manufactured from titanium bar or rod stock so that part of the cylindrical housing and the diaphragm are one piece. One skilled in the art will understand that any construction techniques and material for creating a hermetic package can be used in accordance with several embodiments of the present invention. As used herein, the term hermetic shall be given its ordinary meaning and shall also mean a device enclosure with a helium leak rate from about $1 \times 10^{-11}$ to about $5 \times 10^{-13}$ std. cc/sec.

In another embodiment, the pressure sensor is fabricated by micro electro-mechanical systems (MEMS) techniques, as taught by, for example U.S. Pat. No. 6,331,163, herein incorporated by reference. Electronic and mechanical devices are frequently placed in environments that may damage the components unless some form of protection is provided. For example, some electronic medical devices implanted into a body may be exposed to body fluids that may cause unprotected semiconductor circuits and non-electronic components to fail. Such devices may benefit from a hermetic packaging to limit exposure to these harmful elements. Traditional approaches to creating a protective hermetic package for an implantable medical device generally involve the complete encasement of the silicon or semiconductor components of the device in the hermetic package. Such packages typically utilize a metal such as titanium, or a ceramic material like alumina or zirconia. Various glass materials have also been employed. For example, hermetic cavities have been created to form small vacuum chambers for pressure transducers by bonding silicon components to either silicon or glass. The silicon component is usually fixed into a package with epoxy or soldered into the package. The complete encasement of the silicon component with a separate package adds to the size of the device and also increases its cost.

Similarly, other approaches that have been used for pressure transducers by enclosing the sensor in a metal packaging and coupling the environmental pressure to the sensor through a diaphragm bonded to the packaging. Such approaches place an interface between the environment and the sensor for the electronic components to interact with the environment and to protect the integrity of the device. Such a diaphragm may be made from the same or similar materials as the housing which protects the inner components to facilitate bonding and hermetic sealing of the diaphragm with the housing or protective barrier of the device.

In light of the above discussion, there still remains a need in the art for a system to accommodate medical devices that function effectively by having direct contact of the silicon component with the environment (in many cases, the body). The effective operation of some of these devices precludes complete encasement of the sensor in a protective package. Newer semiconductor components, however, such as semiconductor chemical sensors, may require such direct contact of the silicon component, thereby precluding complete encasement of the sensor. Similarly, pressure sensors fabricated by micro electromechanical systems (MEMS) techniques, as described in U.S. Pat. No. 6,331,163, herein incorporated by reference, require either direct contact with the environment or adequate transmission of environmental pressure through a medium to the sensor.

Accordingly, in one embodiment of the present invention, a method for hermetically sealing a silicon device is provided. The silicon device is coupled to a sensor, such as a pressure transducer, which benefits from having direct contact with its environment (the body). Thus, a method is provided to hermetically seal the non-sensing portion of a silicon device while allowing the sensing portion (e.g. the pressure transducer) to have direct contact with the body. In one embodiment, a silicon chip, a gold preform and a metallic housing are each primed for sealing and are assembled. The assembly is then heated to react the gold preform to the silicon chip and to form a molten gold-silicon alloy in-situ to bind said metallic housing to the non-sensing portion of the silicon chip. In this way, the non-sensing portion of the silicon chip is hermetically sealed, while still permitting exposure of the sensing portion of the silicon chip to the environment.

In one embodiment, the physiological sensor system is configured similarly to a cardiac pacemaker, with a hermetically sealed housing implanted under the patient's skin (subcutaneous) and a flexible lead containing signal conductors with a hermetically sealed pressure transducer module at or near its distal end. The signal conductors may be electrical, fiber optic, or any other means of signal conduction known to skilled artisans. The lead may have a stylet lumen to aid with transducer deployment in the body of a medical patient. The lead may have a lumen for connection of the sensor module to a reference pressure. In one embodiment, the housing contains a battery, microprocessor and other electronic components, including transcutaneous telemetry means for transmitting programming information into the device and for transmitting physiological data out to an external programmer/interrogator. In another embodiment, the implanted pressure sensor lead combination is an integral part of a cardiac rhythm management system such as a pacemaker or defibrillator or various other implantable cardiovascular therapeutic systems know to skilled artisans.

In another embodiment, the signal processing, and patient signaling components are located in a device external to the patient's body in communication with the implanted subcutaneous housing via one of various forms of telemetry well known in the art, such as two-way radio frequency telemetry. In this embodiment, the subcutaneous housing can comprise only a tuned electrical coil antenna, or a coil antenna in conjunction with other components. Other designs for antennae are well known to those skilled in the art and are can be used in accordance with several embodiments of the present invention.

In still another embodiment, the sensor module is directly connected to a coil antenna by short lead or lead of zero length such that the entire system resides in the heart. Such a system may have a small internal battery or power could be delivered transcutaneously by magnetic inductance or electromagnetic radiation of a frequency suitable for penetrating the body and inducing a voltage in the implanted coil antenna. In one embodiment, radiofrequency electromagnetic radiation is used with a frequency of about 125 MHz.

In one embodiment, the sensor module comprises one or more sensors in addition to a pressure transducer at its distal end. These sensors may include a plurality of pressure transducers to measure pressures in the transmural space or locations proximal to the transmural space, or to measure differential pressure between the distal diaphragm and another location. Other types of sensors include, but are not limited to, accelerometers, temperature sensors, electrodes for measuring electrical activity such as the intracardiac electrogram (IEGM), oxygen partial pressure or saturation, colorimetric sensors, chemical sensors for glucose or for sensing other biochemical species, pH sensors, and other sensor types that may be advantageous for diagnostic purposes, or for controlling therapy. Pressure sensors with a frequency response of from about 500 to about 2000 Hz are adequate to detect a wide range of cardiac or respiratory sounds such as valvular closure, opening, murmurs due to turbulent blood flow, pulmonary rates due to congestion, etc. A frequency response of less than about 500 Hz and greater than 2000 Hz can also be used in accordance with several embodiments of the instant invention. Alternatively, a separate hydrophone sensor may be placed in the sensor module. In one embodiment, the sensor module may serve dual diagnostic and therapeutic functions. In one embodiment, the sensor module contains at least one electrode for stimulating the organ in which it is placed. For example, such an electrode or electrodes may be used for electrical pacing the left atrium. Other combinations with therapeutic applications will be known to skilled artisans.

Signals

Left Atrial Pressure Signals

In one embodiment, one of the physiological sensors is a pressure transducer that is used to generate a signal indicative of pressure in the left atrial chamber of the patient's heart (the "left atrial pressure," or LAP). In one embodiment, a LAP versus time signal is processed to obtain one or more medically useful parameters. These parameters include, but are not limited to, mean LAP, temporally filtered LAP (including low-pass, high-pass, or band-pass filtering), heart rate, respiratory variations of LAP, respiration rate, and parameters related to specific features of the LAP waveform such as the so-called a, v, and c waves, and the x, x', and y descents. All these parameters are well known to those skilled in the art. Examples of parameters derived from specific LAP waveform features include the mechanical A-V delay interval, as defined below (as distinct from the electrical A-V interval derived from the electrocardiogram); the relative peak pressures of the a and v waves, and the pressure values at specific times in the LAP waveform, as are understood by those skilled in the art.

In one embodiment, signals indicative of left atrial pressure are periodic signals that repeat with a period the length of which is equal to the period in between heartbeats. Any portion of the signal or a summary statistic of that periodic signal may be indicative of left atrial pressure and provide diagnostic information about the state of the heart. For example, the a, c, and v waves and the x, x', and y descents, described above, correlate with mechanical events such as heart valves closing and opening. Any one of these elements can yield useful information about the heart's condition. Each discrete element represents an individual signal indicative of left atrial pressure. A summary statistic such as the arithmetic mean left atrial pressure also represents a signal indicative of left atrial pressure. One skilled in the art will appreciate that there are additional discrete elements and summary statistics that are valuable indicators of left atrial pressure. Advantageously these components of left atrial pressure are relative to each other and therefore do not have to be compensated for atmospheric pressure and are not subject to offset drift inherent in most pressure transducers. Another such index will be the pressure differential between the mean and respiratory minima.

In one embodiment, the relative heights and/or shapes of the left atrial "a," "c," and "v" waves are monitored to detect and diagnose changes in severity of cardiovascular disease. This information permits differentiation between worsening symptoms of CHF due to volume overload versus impaired left ventricular pump function (such as decrease left ventricular compliance, or acute mitral regurgitation), allowing medical therapy to be appropriately targeted. For example, pure volume overload is usually manifest with a progressive elevation of the mean left atrial pressure and generally responds to fluid removal by taking a diuretic medication, natriuretic peptide, or an invasive technique known as ultrafiltration of the blood. Decreased left ventricular compliance is the diagnosis when the "a" wave increases without shortening of the atrioventricular (AV) delay or in the presence of mitral stenosis. Acutely decreased compliance may be indicative of left ventricular (LV) ischemia, while chronically decreased compliance may be indicative of LV wall thickening know as hypertrophy. The former may respond to nitrates or coronary artery interventions, while the latter may respond to beta or calcium antagonist drugs, or chemical septal ablation. Increases in the "v" wave amplitude and merging with the "c" wave to produce a "cv" wave is usually indicative of acute mitral valve regurgitation. This may be due to a sudden mechanical failure of the valve or its supporting apparatus or it may be due to acute ischemia of the supporting papillary muscles as part of an acute coronary artery syndrome. Sudden mechanical failure requires surgical repair or replacement, while ischemia may require anti-ischemic medications such as nitroglycerin or coronary artery interventions such as angioplasty or bypass surgery. In another embodiment, atrial fibrillation and atrial flutter are detected by analysis of the LAP waveform. In another embodiment, spectral analysis of the LAP versus time signal is performed.

Measurement of Relative Pressure (Gauge Pressure)

In one embodiment, the system contains components to obtain a signal indicative of pressure relative to atmospheric pressure. An implanted apparatus for measuring absolute pressure at a location within the body is provided as above, which further communicates this information, as either an analog or digital signal, to an external signal analyzer/communications device. The external signal analyzer/communications device further contains a second pressure transducer configured to measure the atmospheric (barometric) pressure. The analyzer/communications device performs a calculation using the absolute pressure from the implanted module and the atmospheric pressure to obtain the internal pressure relative to atmospheric pressure, that is, the difference between the absolute pressure at the location within the body and the absolute barometric pressure outside the body. This pressure, also known as the gauge pressure, is known to those skilled in the art to be the most physiologically relevant pressure measure.

In one embodiment, gauge pressure measurements are performed only when the implanted apparatus is queried by the external analyzer/communications device, advantageously assuring that the atmospheric pressure at the time and patient's location is available and correctly matched with the absolute internal pressure reading. It will be clear to those skilled in the art that unmatched internal and barometric pressure readings would render the gauge pressure measurement inaccurate or useless. In this embodiment, internal absolute measurements are made only when the external analyzer/communications device is physically present. In one embodiment, this is accomplished by having the external device supply operating power to the implant module to make the measurement. In another embodiment, this is accomplished by requiring a proximity RF link to be present between the external and implantable modules, immediately before, after and/or during the measurement.

In another embodiment, differential pressure is obtained by the lead containing a lumen that communicates a reference pressure to the sensor module as well known to skilled artisans.

Anchoring/Fixation Apparatus

In several embodiments, the physiological sensor system is coupled to surrounding tissue by one or more anchoring mechanisms. In one embodiment, tissue anchoring apparatus is used to affix the transducer module in the desired transmural position, to prevent sensor module migration, to promote rapid tissue overgrowth without thrombus formation, and to be mechanically and biologically compatible with the tissue so as not to induce an inflammatory reaction or cause device erosion. In several embodiments, a pressure measurement device is anchored within an atrial septum wall. However, the skilled artisan will recognize that the methods described for anchoring a pressure transducer to a septal wall can also be applied to affix any suitable sensing module to any wall of an organ or a vessel within a patient.

In one embodiment, the module is associated with proximal and distal anchoring systems that assure localized fixation of the distal end of the module and transducer diaphragm essentially coplanar with the plane of the blood contacting surface of the desired chamber or vessel so as to promote rapid tissue overgrowth. One such a system is described in U.S. patent application Ser. No. 10/672,443, herein incorporated by reference.

In one embodiment, an anchoring device is configured to cross the septum between the right and left atrium and trap itself between the two chambers such that a pressure-sensing member is exposed to the left atrium. The device is configured in a manner that will allow positioning of the pressure-sensing member at a desired location relative to the septal wall while conforming to anatomical variations. In one embodiment, the diaphragm is essentially coplanar with the left atrial side of the intra-atrial septum. In one embodiment, the term "essentially coplanar" is defined as the plane defined by the outer surface of the diaphragm is within about ±0.5 mm distance of the plane tangential to the left atrial side of the intra-atrial septum at the location it is traversed by the pressure-monitoring module. In another embodiment, this distance is defined as about ±1 mm. In yet another embodiment of the present invention, this distance is defined as about ±2 mm.

In one embodiment, the device is designed such that the diaphragm will not be recessed within the septal wall. This embodiment is particularly advantageous because thrombi are more likely to form in regions of blood stasis within the recess. A thicker layer of neointima will tend to form as the tissue remodels, creating an optimal blood flow pattern by eliminating the recess. Likewise, a diaphragm that protrudes into the left atrium may cause microscopic high shear zones where high velocity blood flow interacts with the device. High shear is known to activate platelet thrombus formation. Also, the longer distance for tissue in-growth from the surrounding septum may delay tissue coverage and healing. Nonetheless, one skilled in the art will understand that, in accordance with a few embodiments of the current invention, a portion of the diaphragm may be recessed within the septal wall or may protrude through the left atrium.

According to one embodiment, the sensor system comprises a proximal anchor having one or more helical legs extending between a proximal ring and a distal ring. In one embodiment, the device also comprises a distal anchor having one or more legs. The device further includes a hermetically sealed pressure transducer module configured to be supported by the proximal and distal anchors. The proximal and distal anchors of this embodiment are preferably configured to be movable between a collapsed delivery position and an expanded position in which the proximal and distal anchors secure the module to a wall of an organ within a patient.

In one embodiment of the current invention, a system for diagnosing and/or treating a medical condition in a patient using a device to measure pressure is provided. One embodiment comprises a pressure-sensing module configured to be implanted within a patient, a proximal anchor comprising at least one helical leg configured to expand from a compressed state to a relaxed state, and a distal anchor comprising at least one leg configured to expand from a compressed state to an expanded state. The proximal anchor and the distal anchor of this embodiment are preferably configured to sandwich an atrial septum wall (or the left atrial free wall, the pulmonary vein wall, or any other suitable wall of a heart or a blood vessel) between the proximal anchor leg and the distal anchor leg and to support the module in the septum wall. In one embodiment, the system also comprises a delivery system, such as a catheter, configured to deploy the sensor, the proximal anchor, and the distal anchor in the septum wall. In one embodiment, the system is particularly suited to monitor congestive heart failure in the patient.

Another embodiment provides a system for monitoring a patient for congestive heart failure, comprising an implantable pressure transducer and a means for anchoring the pressure transducer to an organ wall. In one embodiment, the means for anchoring comprises one or more anchoring members adapted to contact a proximal side and a distal side of a wall of an organ to anchor the pressure transducer to the organ wall. The system can further comprise a means for delivering the implantable transducer and means for contacting the organ wall.

In another embodiment, a method of monitoring congestive heart failure in a patient is provided. In one embodiment, the method comprises providing a pressure sensor secured to a proximal anchor and a distal anchor, and delivering the pressure sensor to a hole in an atrial septum of the patient's heart. The method further comprises deploying the pressure sensor with the proximal anchor on a proximal side of the septum, and the distal anchor on a distal side of the septum; monitoring a fluid pressure in the left atrium of the patient's heart.

Another embodiment provides a method of monitoring congestive heart failure within a patient. In one embodiment, the method comprises providing an implantable pressure transducer and coupling said implantable pressure transducer to a means for anchoring said pressure transducer in an organ wall. The method further comprises delivering said pressure transducer and said means for anchoring to said organ wall, and causing said means for anchoring said pressure transducer in said organ wall to expand, thereby capturing said organ wall and anchoring said pressure transducer thereto.

According to still another embodiment, a method of anchoring a device in the heart of a patient is provided. The method includes providing an implantable cardiac anchoring device comprising a proximal anchor having at least one helical leg and a distal anchor having at least one linear leg. The method comprises attaching an implantable pressure-sensing module to the implantable cardiac anchoring device, positioning a tubular delivery catheter in a wall of a patient's heart, and inserting the implantable module and the implantable cardiac anchoring device into the tubular delivery catheter. The method further includes deploying the sensor and the implantable cardiac anchoring device such that the sensor is retained in a transverse orientation relative to the wall.

Turning to the figures, embodiments of cardiovascular anchoring devices for use in anchoring an implantable pressure sensor module to an organ wall (such as an atrial septum wall) will now be described. In some embodiments, the module comprises a sensor, and in one particular embodiment, the module is a pressure sensor, such as a pressure transducer. Several figures included herein illustrate a straight device and deployment apparatus for the purpose of demonstration. However, one skilled in the art will understand that, in use, the delivery catheter and contained components will typically be substantially flexible or may assume other non-straight shapes. For example, a delivery catheter can be configured to include a pre-shaped curve or a pre-shaped stylet in order to facilitate navigation of a patient's tortuous vasculature. As will also be clear to the skilled artisan, the flexibility of certain components will be particularly advantageous for navigation through tortuous anatomy.

FIG. 1 illustrates embodiments of a distal anchor 110. In one embodiment, the distal anchor 110 is part of an anchor and sensor assembly, such as the anchor and sensor assembly 100 illustrated in FIGS. 10-12. In one embodiment, the anchor and sensor assembly 100 includes a distal anchor 110 and a proximal anchor 112 configured to secure a sensor 120 to a wall of an internal organ (such as a left atrium of a heart)

within a patient. The distal and proximal anchor components 110 and 112 are configured to be compressed to a delivery state such that they can be placed within a tubular delivery catheter. The anchors 110 and 112 are further configured such that when they are released from their compressed state, they will relax to assume a preformed, expanded configuration in which they engage opposite sides of a septum wall 210 (e.g., see FIGS. 20 and 21) in order to support the sensor 120 in an operative position.

In order to allow the proximal and distal anchors 110 and 112 to self-expand from a compressed state to an expanded state, they are preferably made from materials that exhibit superelastic and/or shape memory characteristics. Alternatively, the anchors could be made from other non-superelastic or non-shape memory materials as desired. For example, suitable materials for fabrication of the proximal and distal anchors include, but are not limited to, nickel titanium alloys (NiTi or NITINOL), cobalt-chromium alloys, stainless steel, ELGILOY, MP35N or other biocompatible, superelastic, and/or shape memory materials that are well known to those skilled in the art of clinical medical devices. The anchors can be made by any suitable process appropriate for a particular material. For example, the anchors could be molded, machined, laser cut, etc as desired.

Figure 2:
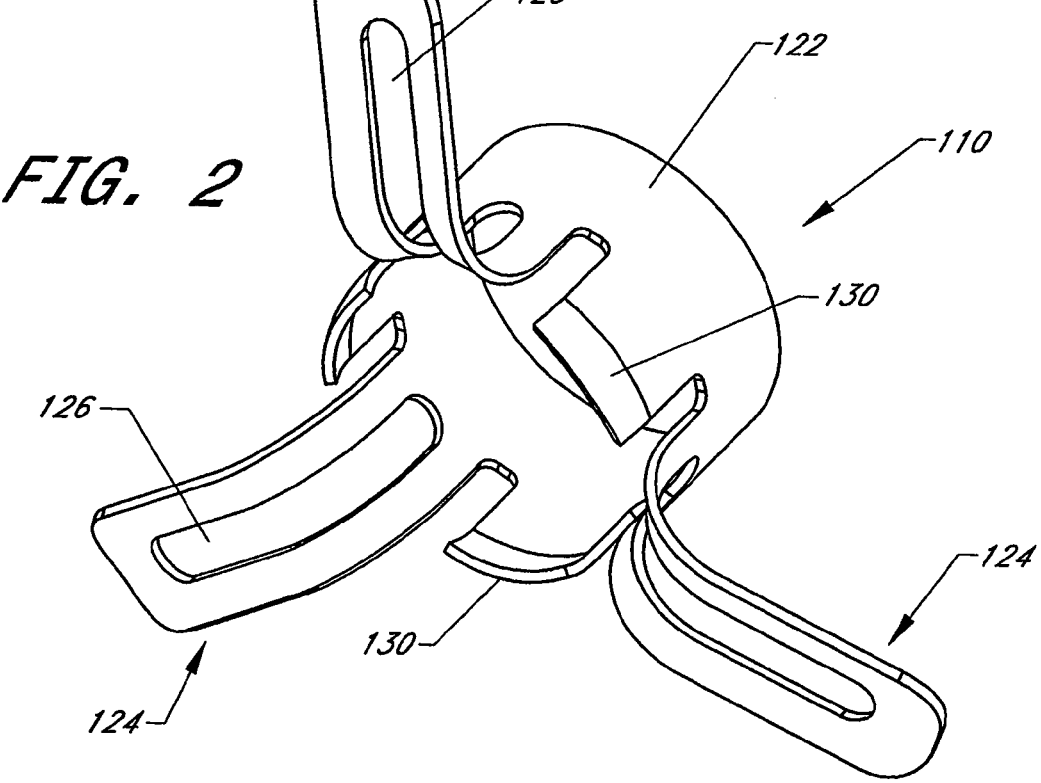
FIG. 2 is a perspective view of the distal anchor of FIG. 1 in an expanded state.

FIGS. 1 and 2 illustrate one embodiment of a distal anchor 110 in a compressed state and an expanded state respectively. The distal anchor 110 generally comprises a cylindrical base portion 122 with a plurality of legs 124 extending distally therefrom. In the illustrated embodiment, the legs 124 include slots 126 for the purpose to advantageously promote more rapid tissue overgrowth in a deployed position, which will advantageously aid in securement of the device to the septum wall and prevent thrombus formation. Referring to FIG. 26, any of a variety of keyed or slotted anchor configurations may be used. In another embodiment, the slots in legs 124 can vary in width. In another embodiment, the slots in legs 124 can be curved or serpentine. In another embodiment, the slots in legs 124 may be replaced by one or more holes of equal or diverse diameters. In an alternative embodiment, the legs 124 can be solid. In yet another embodiment, the legs 124 can be keyed or slotted at right angles to their long axes from one or both sides. Referring back to FIGS. 1 and 2, the distal anchor 112 also comprises struts or locking tabs 130 configured to engage a portion of the sensor 120 as will be further described below. In its compressed state, as shown in FIG. 1, the distal anchor 124 occupies a substantially cylindrical shape with its legs orient forward or distally, thereby allowing it to be placed within a cylindrical, tubular delivery catheter or delivery sheath. The forward orientation of the distal anchors legs project distally beyond the pressure-sensing diaphragm, and protect the diaphragm from being damaged during handling or catheter passage into the body.

In an expanded shape, as shown in FIG. 2, the legs 124 of the distal anchor 110 bend outwards and proximally. In one embodiment, the legs 124 bend outwards until they are substantially perpendicular to the longitudinal axis of the cylindrical base portion 122. In alternative embodiments, the legs bend proximally until they are oriented at more than 90° to the longitudinal axis of the cylindrical base 122 as shown for example in FIG. 8. In such embodiments, the angle $\theta$ (which represents the amount beyond perpendicular to the longitudinal axis that the legs 124 can bend) can be between about 0° and about 20°. In some embodiments, the angle $\theta$ can be between about 5° and about 15°, and in one specific embodiment, the angle $\theta$ can be about 10°. In one embodiment, the angle $\theta$ will preferably be reduced to zero degrees when the distal anchor 110 is deployed on a distal side of a septum wall 210 (see FIG. 20) with a proximal anchor 112 on the proximal side of the wall 210 due to the opposing force of the proximal anchor 112. Thus, in one embodiment, the angle $\theta$ is selected along with a spring constant of the distal anchor legs 124 such that an opposing force applied by the proximal anchor 112 through a septum wall of a particular thickness (as will be further described below) will cause the angle $\theta$ to be substantially reduced to zero or to deflect a small amount in the distal direction so as to conform with a substantially concave left atrial septal surface. In doing so, wall contact is distributed over the entire proximal side surface area of the distal anchor legs to minimize pressure induced necrosis of the septum.

FIGS. 3-6 illustrate one embodiment of a proximal anchor 112 in compressed (FIG. 3) and expanded (FIGS. 4 through 6) states. In its compressed state, the proximal anchor 112 occupies a substantially cylindrical space such that it can be placed in a cylindrically tubular delivery catheter. The proximal anchor 112 generally includes a proximal ring 140 and a distal ring 142 with a plurality of legs 144 extending therebetween. The proximal anchor 112 can include any number of anchor legs 144 as desired. For example, in the embodiment illustrated in FIG. 3, the proximal anchor comprises six anchor legs 144. Alternatively, the proximal anchor 112 can include a greater or lesser number of anchor legs 144. The proximal anchor 112 can also include struts or locking tabs 150 which can be used to secure the sensor 120 to the proximal anchor as will be further described below.

In the embodiment of FIG. 3, the anchor legs 144 are configured to follow a helical path between the proximal ring 140 and the distal ring 142. In one embodiment, the helical path of the anchor legs 144 passes through 360 degrees between the proximal ring 140 and the distal ring 142. In alternative embodiments, the proximal anchor 112 can be longer and/or the legs 144 can pass through 720 degrees. In general, it is desirable that the legs pass through a substantially whole number of complete circles between the proximal and distal rings 140, 142. This configuration allows the proximal anchor 112 to negotiate the tortuous path that is typically encountered during delivery of the device to a desired location within a patient. The spiral or helical shape of the proximal anchor is particularly advantageous because this configuration equalizes bending stresses experienced by the anchor legs 144 in order to maintain an internal lumen (typically with a circular cross-section) of the proximal anchor 112 as the device is navigated through a tortuous path. Additionally, the illustrated configuration advantageously increases flexibility of the proximal anchor 112 and reduces its diameter to allow the anchor to be more effectively negotiated through a tortuous anatomy without damaging the device or injuring the patient.

FIGS. 4-6 illustrate the proximal anchor 112 in its expanded state. As shown, proximal anchor 112 preferably assumes a substantially "mushroomed" shape in its expanded state. In moving between the compressed and expanded states (assuming the distal ring 142 is held substantially stationary), the anchor legs 144 preferably unwind and buckle outwards and distally relative to the proximal ring 142. As shown, the proximal anchor 112 preferably "unwinds" such that the proximal ring 140 rotates relative to the distal ring 142 as the anchor 112 moves between its compressed and expanded states. The amount of rotation of the proximal ring relative to the distal ring will typically be a function of the final resting distance between the proximal ring and the distal ring.

In their fully expanded state, the anchor legs 144 preferably bend outwards and distally until each leg 144 forms a loop 152 with a distal most edge 154 that is positioned substantially distally from the distal edge of the distal ring 142. In some embodiments, the anchor assembly can be configured such that, in free space (i.e. with no tissue or material between the proximal and distal anchors), the distal edge 154 of the proximal anchor leg loops 152 and the proximal tissue-contacting surface of the distal anchor 110 can actually overlap by up to about 0.06". In some embodiments the overlap can be between about 0.03" and about 0.05", and in one embodiment, the distance is about 0.04". In some non-overlapping embodiments (as shown in FIG. 5), the distance 156 between the distal edge 154 of the proximal anchor leg loops 152 and the distal edge of the distal ring 142 of the proximal anchor can be between about 0.040" and about 0.070". In some embodiments, the distance 156 is between about 0.050" and about 0.060", and in one particular embodiment, the distance 156 is about 0.054". By providing the proximal and distal anchor legs 144 and 124 with sufficient resilience that they relax to overlapping positions, it can be assured that the assembly will be able to securely anchor to even the thinnest of septum walls. By selecting certain mechanical properties of the proximal anchor, its elasticity can be matched to that of the tissue wall it is to contact, thus minimizing the chances for pressure induced tissue necrosis and subsequent erosion of the device through the septum.

FIGS. 7-9 illustrate the distal anchor 110 mounted to a sensor module 120. In the illustrated embodiment, the sensor 120 is a pressure transducer having a substantially cylindrical body 160 with a pressure-sensing face 162 at its distal end, and a lead-attachment interface 164 at its proximal end. In one embodiment, as shown, the lead-attachment interface comprises a series of annular notches which can be engaged by a tightly-wound coil to secure the electrical lead. In some embodiments, a lead-attachment mechanism can be welded in place (such as by laser welding) on the sensor 120 in order to provide a more secure connection. In another embodiment, the lead-attachment interface 164 can comprise screw threads. Alternatively, the skilled artisan will recognize that any number of suitable alternative interfaces could also be used. Additional details of a suitable pressure sensor are provided, for example, in U.S. Pat. No. 6,328,699 to Eigler et al., which is incorporated herein by reference. In alternative embodiments, the sensor 120 can be configured to sense and/or monitor any desired parameter within a patient.

In the embodiment of FIGS. 7-9, the distal anchor 110 is secured to the sensor 120 by struts or locking tabs 130 on the anchor, which engage an angled annular groove 170 which circumscribes a distal portion of the sensor 120. The locking tabs 130 extending distally from the distal anchor 110 (as shown in FIGS. 1 and 2) are preferably bent slightly radially inwards such that they will engage the distal annular groove 170 in the sensor as shown in the detail view of FIG. 9. Similarly, a proximal annular groove 172 is provided to be engaged by the locking tabs 150 of the proximal anchor 112 (shown in FIG. 3). The anchor-to-sensor attachment system illustrated in FIGS. 7-9 allows the anchors 110 and 112 to rotate about the sensor 120. In some situations it is desirable to prevent rotation of the anchors relative to the sensor 120 by spot-welding the proximal and/or distal anchors to an annular flange 174 provided on the sensor 120. Alternatively, in place of an annular groove, the sensor could comprise angled notches for receiving the locking tabs in a single rotational orientation on the sensor 120. Alternatively still, other attachment systems can also be used, such as welds, adhesives, and other mechanical fasteners.

FIG. 8 illustrates a cross-sectional view of the sensor 120 attached to a distal anchor. In some embodiments, it may be desirable to vary the distance 166 between a distal most edge of a distal anchor leg 124 (in an expanded state as shown) and the pressure-sensing face 162 of the sensor 120. In one embodiment, the distance 166 is preferably zero, i.e., the pressure-sensing face 162 is preferably substantially co-planar with the distal most point of a deployed distal anchor leg 124. Such a configuration will preferably advantageously place the pressure-sensing face 162 substantially flush with the atrium wall, thereby reducing the hemodynamic effect experienced by the sensor 120, minimizing the effect of the sensor 120 on blood flow patterns, thus reducing the initiation of thrombus formation, and minimizing the path lengths for tissue to overgrow the sensor diaphragm. In alternative embodiments, it may be desirable that the sensor 120 be moved distally such that the pressure-sensing face extends distally outwards from the distal anchor. Alternatively still, it may be desirable to support the sensor 120 within the distal anchor 110 such that the sensor face 162 is recessed within the distal anchor 110. The location of the sensor face relative to the distal anchor can be varied by changing a location of the distal annular groove 170 and/or by varying a size of the locking tabs 130.

FIGS. 10-14 illustrate an alternative embodiment of an anchor and sensor assembly 100 wherein the components are attached to one another with interlocking mechanical fasteners. As shown, the proximal anchor 112, the distal anchor 110, and the sensor 120 include interlocking structures configured to mechanically interconnect the assembly components in such a way as to limit both axial and rotational movement of the components relative to one another.

The distal anchor of FIGS. 10-12 comprises a plurality of fingers 180 which extend proximally from the cylindrical base portion 122. As shown, each finger 180 can include a narrow neck section 182 and a wider proximal tab section 184. The proximal anchors 112 can include correspondingly shaped slots 186 in the distal ring 142 to receive the fingers 180. The sensor 120 can also include corresponding interlocking structures configured to engage structures on the distal and/or proximal anchors 110, 112. As shown the sensor 120 can include raised sections 188 around the circumference of the cylindrical body 160. The raised sections 188 can be positioned so as to leave gaps 190 for receiving the neck sections 182 of the fingers 180. The raised sections 188 can be machined into the cylindrical body 160 of the sensor, or they can comprise independent segments welded, adhered, or otherwise secured to the cylindrical body 160 of the sensor 120. The components can be assembled as shown in FIG. 10 to provide a secure and substantially immobile connection between the proximal anchor 112, the sensor 120 and the distal anchor 110. The specific geometry of the interlocking structures of FIGS. 10-12 are intended to be merely exemplary, and the specific shapes of the fingers 180, slots 186, and spaces 190 can alternatively include a variety of different geometric shapes in order to provide a secure connection between the components. If desired, the interlocking structures can also be welded together once they are assembled, thereby further securing the connection.

Radiopaque Markers

Figure 13:
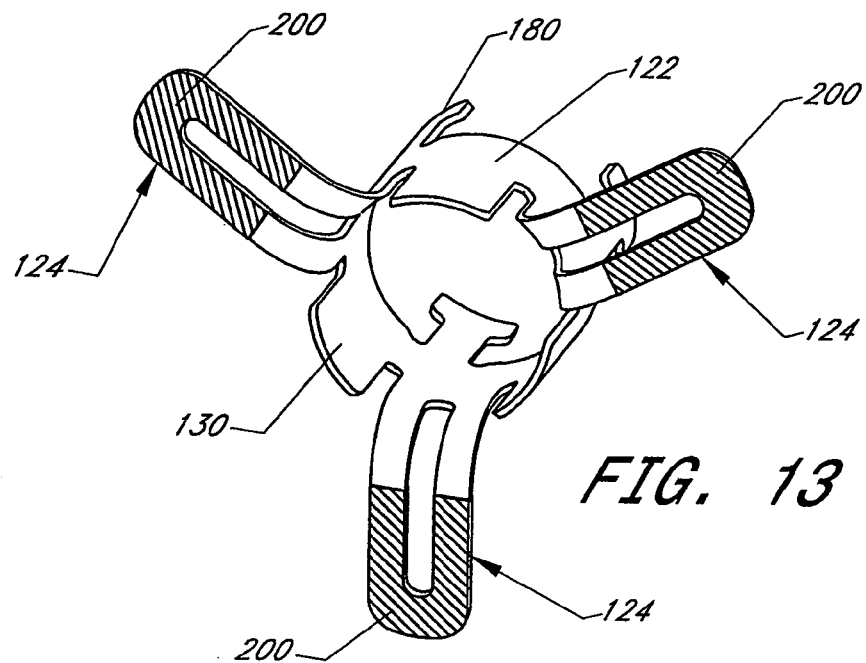
FIG. 13 is a perspective view of an alternative embodiment of a distal anchor in an expanded state.
Figure 14:
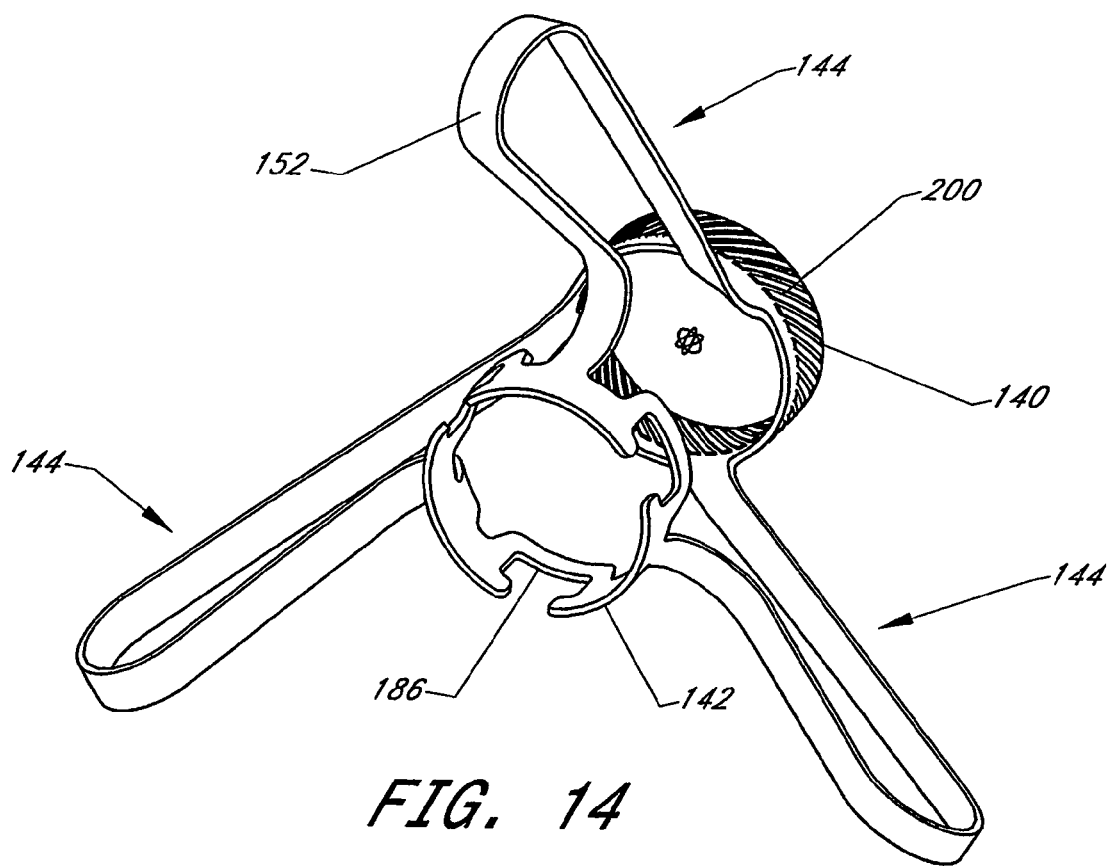
FIG. 14 is a perspective view of an alternative embodiment of the proximal anchor.

In one embodiment, one or more radiopaque markers are used in conjunction with deployment of the physiological sensor. FIGS. 13 and 14 illustrate the proximal and distal anchors of FIGS. 10-12 with the addition of a plurality of radiopaque markers 200 for facilitating visualization of the assembly under fluoroscopy during deployment. As shown, radiopaque markers 200 can be applied to the legs 124 of the distal anchor 110 and/or to the proximal ring 140 of the proximal anchor 112. Radiopaque markers can also be provided on other portions of the proximal anchor 112, the distal anchor 110 and/or the sensor 120. The radiopaque markers are preferably placed in "low flex zones," such as the tips of the distal anchor legs 124 and the proximal ring 140 of the proximal anchor. Generally, "low flex zones" are portions of the anchor that experience substantially minimal flexing or bending. One advantage of this embodiment is that the materials used in the radiopaque markers will not negatively affect the elasticity of the flexing anchor sections. Another advantage is that the radiopaque markers will not separate from the anchor within a patient.

Radiopaque markers are typically made of noble metals, such as gold, platinum/ iridium, tantalum, etc, and are typically attached to the anchor by selective plating or ion beam deposition. Alternatively, the markers could be micro rivets and/or rings that are mechanically attached to portions of the system components. In order to reduce the risk of galvanic corrosion which can be experienced by dissimilar metals exposed to blood, the radiopaque material can be selected to have a galvanic corrosion potential that is substantially similar to a galvanic corrosion potential of the material from which the anchors and/or sensor are made. For example, if the anchors 110, 112 are to be made of NITINOL, the radiopaque markers 200 can be made of tantalum. Alternatively, an electrically insulating coating (conformal coatings) such as parylene or other biocompatible synthetic material can be used to cover the radiopaque markers in order to isolate the marker and anchor section from exposure to the blood or other bodily fluid.

Figure 20:
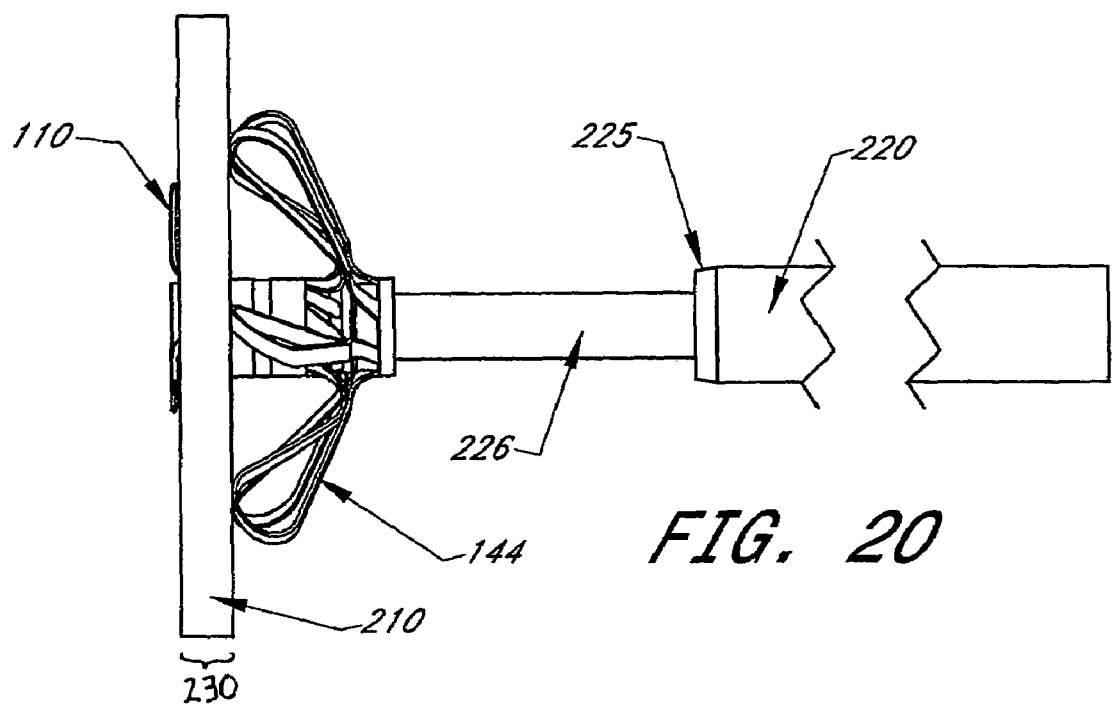
FIG. 20 is a side view of an anchor and sensor assembly deployed and anchored to a thin atrial septum wall (shown in cross-section).
Figure 21:
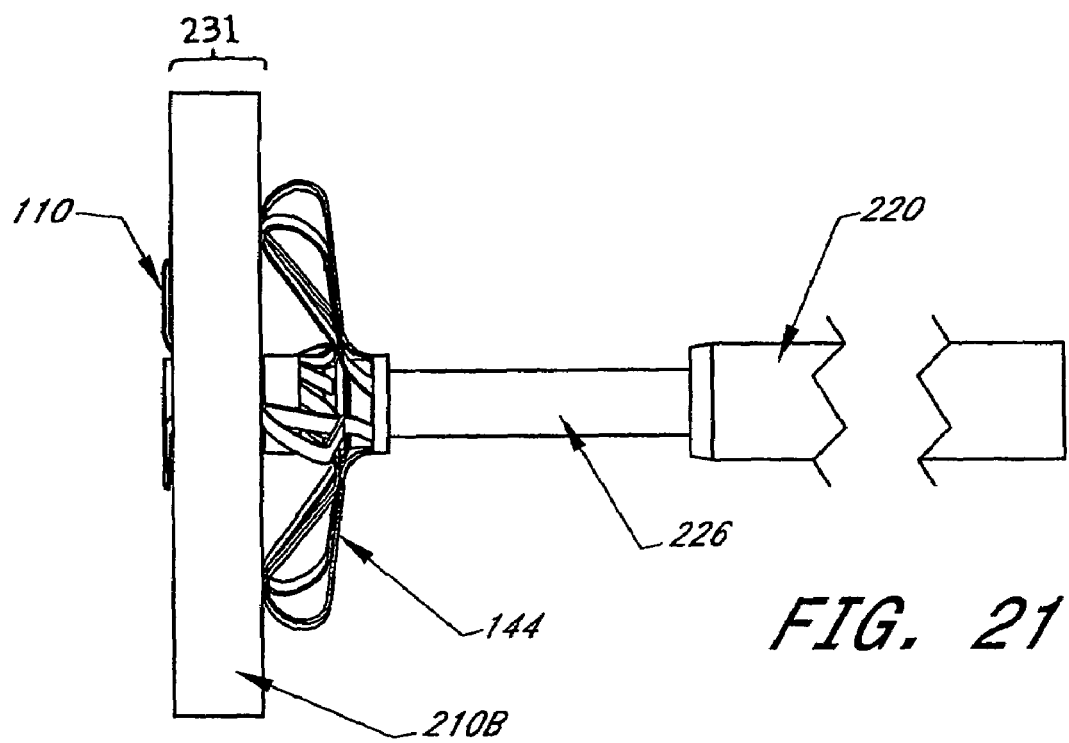
FIG. 21 is a side view of an anchor and sensor assembly deployed and anchored to a thicker atrial septum wall (shown in cross-section).

In one embodiment, the legs 144 of the proximal anchor 112 apply a lower spring force to the septum wall 210 than the legs 124 of the distal anchor 110 so that variations in septum wall thickness are accommodated by variations in the position of the proximal anchor legs 144 as shown in FIGS. 20 and 21. FIG. 20 shows a relatively thin septum wall 210 with a thickness 230. In order to securely anchor the sensor, the legs 144 of the proximal anchor 112 will extend distally until their distal motion is stopped by the pressure of the septum wall 210. In the embodiment of FIG. 21, the septum wall 210 is substantially thicker 231, thereby causing the legs 144 of the proximal anchor 112 to extend a shorter distance distally than in the embodiment of FIG. 20.

FIGS. 27A-C, 28 and 29A-B show another embodiment of the proximal anchoring assembly. In this embodiment, the legs 320 of the proximal anchor 322 attach in a similar manner to the embodiment shown in FIGS. 10-12, but the outer ends 324 of the anchor legs are left free. The legs are preformed into a predetermined shape such that when a delivery sheath 326 is withdrawn the legs 320 return to the desired deployed shape. In this embodiment, the proximal anchors are configured to fold forward (distally) upon retraction of the system into the delivery sheath, advantageously allowing the device to be retrieved and possibly re-deployed if necessary.

Figures 30, 31:
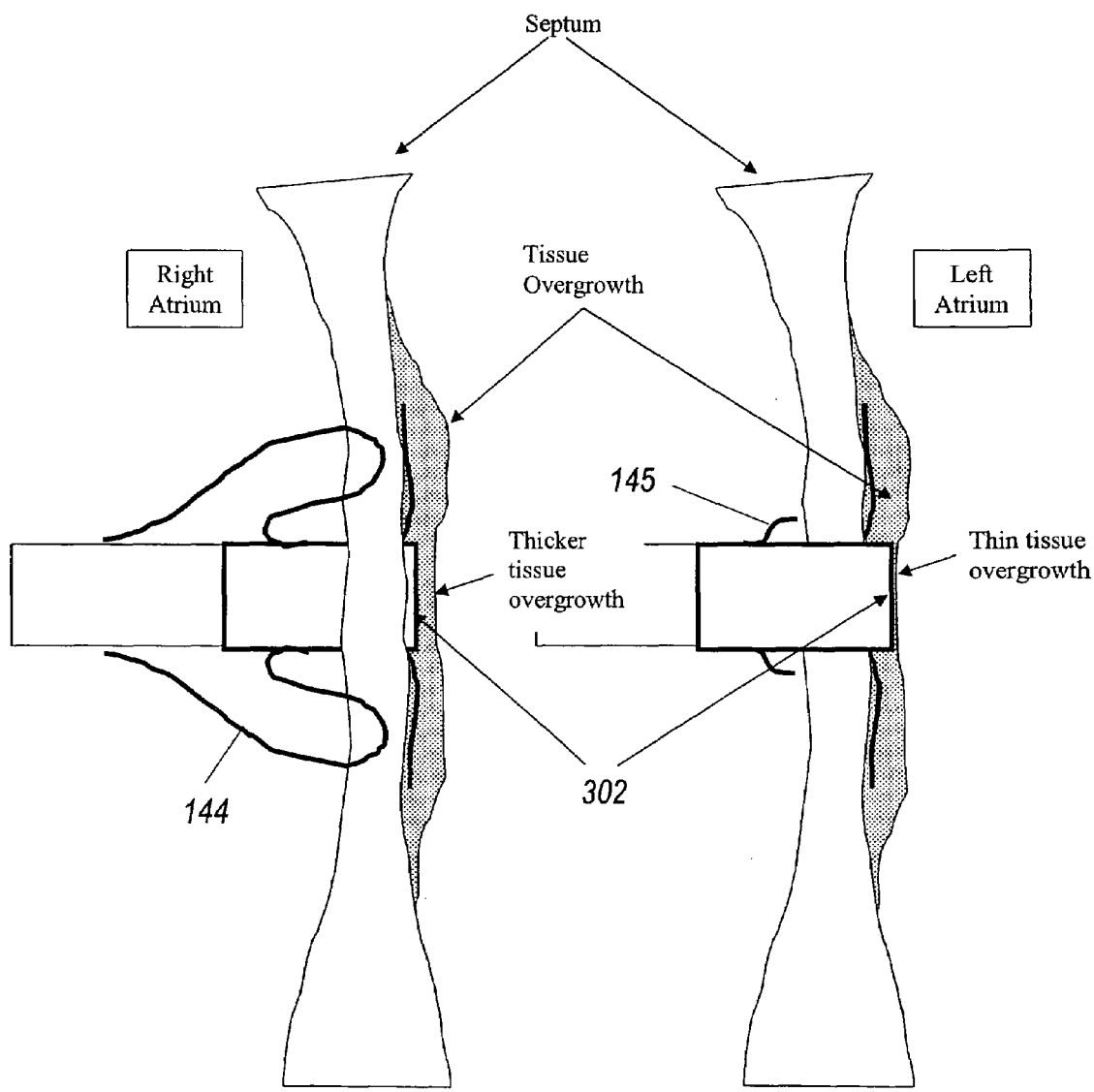
FIG. 30 is a side view of an anchor and sensor assembly where the sensor diaphragm is generally coplanar with the distal anchor and the left atrial surface of the septal wall, showing thick tissue overgrowth of the diaphragm and distal anchors.
FIG. 31 is a side view of an anchor and sensor assembly where the sensor diaphragm is extended distally from the plane of the distal anchors and the left atrial surface of the septal wall, showing reduced thickness of tissue overgrowth of the sensor diaphragm.

FIGS. 30 and 31 show two embodiments of the present invention. The system shown in FIG. 30 is configured with a proximal anchor having helical legs 144 and with the diaphragm 302 essentially coplanar with the distal anchor legs 124. FIG. 31 shows another embodiment of the present invention, comprising small, barb-like, proximal anchors 145 and configured with the sensor diaphragm 302 protruding distally from the plane of the distal anchor legs 124. The neointima depicted in FIG. 31 is not as thick as in Figure NF30 because in some embodiments, the small barb-like proximal anchors 145 may reduce chronic irritation compared to the larger, spring-loaded helical proximal anchors 144. The tissue thickness overlying the sensor diaphragm 302 is further reduced in the configuration of FIG. 31 due to the protrusion of the diaphragm 302 away from the septal wall.

Diaphragm Mechanics and Material Properties

In one embodiment, the transducer module distal diaphragm is a relatively thick titanium membrane such that its compliance (defined as the change in displacement of the center portion of the diaphragm per change in unit pressure) is substantially lower than the compliance of the overlying tissue encapsulation thus assuring that the motion of the diaphragm in response to changes in fluid pressure is only minimally reduced by tissue overgrowth. In one embodiment, a 2.5 mm diameter diaphragm is between about 0.001 to 0.003 inches (25 to 76 microns) thick. In another embodiment, the diaphragm thickness is between about 0.003 to 0.005 inches (76 to 127 microns). Diaphragms of this type have relatively low compliance, meaning that they exhibit relatively little strain, or displacement, in response to changes in pressure. For example, in one embodiment, a 2.5 mm diameter by 50-micron thick titanium foil diaphragm has a displacement at its center of only about 4 nm per mm Hg pressure change. One advantage of using a low compliance diaphragm is that tissue overgrowth will minimally affect the relatively reduced range of motion, thus minimizing errors in the sensed pressure reading. Generally, the more non-compliant a diaphragm is, the more sensitive or higher gain the internal transducer components may need to be to maintain the output signal amplitude.

In general, the motion of the center of the diaphragm, assuming uniform diaphragm thickness, small deflections, infinitely rigid clamping around the diaphragm periphery, perfectly elastic behavior and negligible stiffening and mass effects due to presence of strain gauges on the diaphragm, is given by the equation $$Y_c = \frac{3PR_o^4(1-v^2)}{16t^3 E}$$

where: $Y_c$=center deflection (mm), P=pressure (Pa), $R_o$=diaphragm radius (mm), v=Poisson's ratio (dimensionless), t=diaphragm thickness (mm), and E=modulus of elasticity (Pa).

In one embodiment, the pressure transducer diaphragm is constructed of Ti 6-4 with material properties comprising of approximately $R_o$=1.1 mm, v=0.31, t=0.05 mm, and E=100 GPa. Such a titanium diaphragm will have very small deflections, about $2.4 \times 10^{-6}$ mm/mm Hg. Tissue growth over such a diaphragm can be modeled by the material properties of the aorta where v=0.30, t=0.5 mm (10 times the diaphragm thickness), and E=1 MPa or 100,000 times more elasticity than titanium. Such tissue will be displaced approximated $2.6 \times 10^{-4}$ mm/mm Hg, or about 100 times more than the titanium diaphragm. Thus, such tissue overgrowth will inhibit the motion of the titanium diaphragm by less than about 1.0%, thus having a clinically negligible effect on sensor gain over the range of physiologic pressures expected in the left atrium. Halving the diaphragm thickness to about 0.025 would cause similar tissue overgrowth to inhibit the motion of the diaphragm by more than about 7% and, if other adjustments are not made, may cause clinically significant errors over the physiologic range of expected left atrial pressures.

In one embodiment, the pressure transducer membrane is designed to have very low compliance. In one embodiment, a low compliance pressure transducer is fabricated using titanium foil as described above. In another embodiment, a low compliance pressure transducer is fabricated from, for example, silicon, using micro electromechanical systems (MEMS) techniques.

Figure 32:
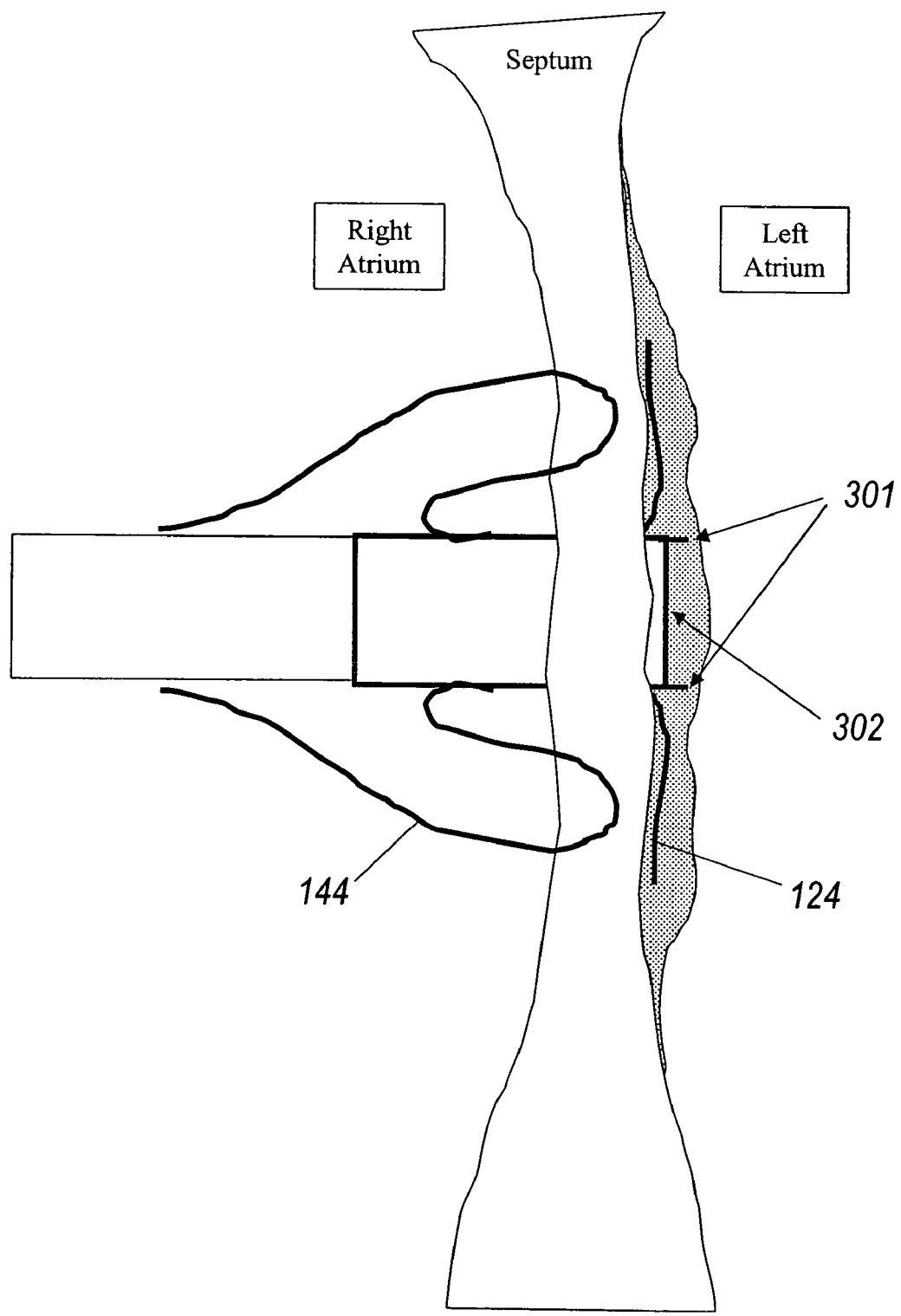
FIG. 32 is a side view of an anchor and sensor assembly where the sensor diaphragm is surrounded by a cupped distal rim on the sensor housing to minimize coupling between stresses in the septal wall and the diaphragm.
Figure 33:
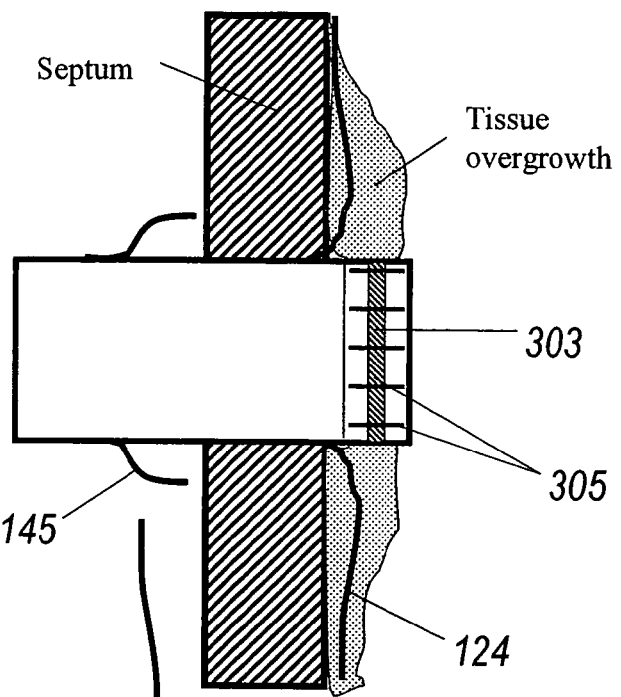
FIG. 33 is a side view of an anchor and sensor assembly where a drug-eluting band surrounding the distal circumference of the sensor housing is provided. Crossing channels are provided parallel to the long axis of the housing perpendicular to the drug-eluting band to allow for limited ingrowth of endothelial cells to cover the sensor diaphragm.
Figure 34:
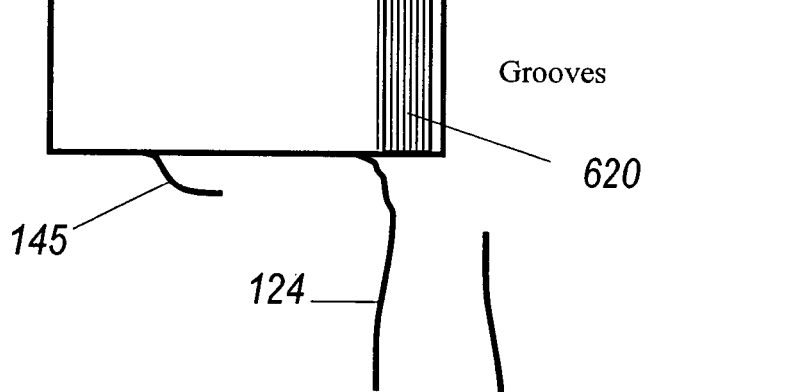
FIG. 34 is a side view of an anchor and sensor assembly in which grooves are provided around the sensor housing distal circumference to anchor tissue overgrowth to reduce the coupling of stress between the tissue and the sensor diaphragm.
Figure 35:
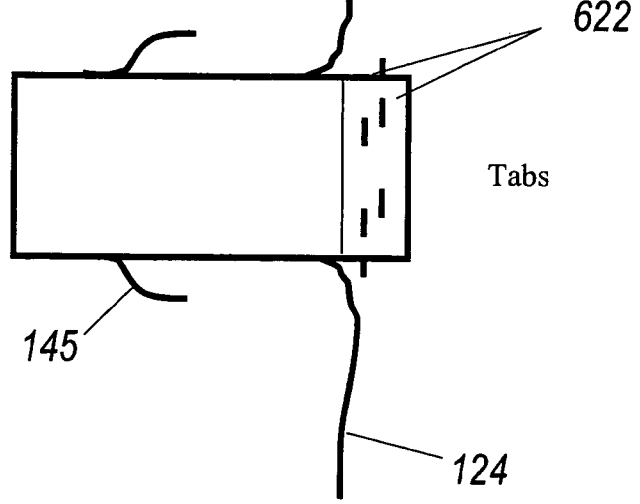
FIG. 35 is a side view of an anchor and sensor assembly in which tabs are provided around the sensor housing distal circumference to anchor tissue overgrowth to reduce the coupling of stress between the tissue and the sensor diaphragm.

While the effect of tissue overgrowth on sensor gain may be minimized by aspects of this invention described above, the skilled artisan will recognize that any force on the sensor produced by contact with tissue will cause a positive offset in the sensed pressure. If such tissue-contact force is constant, then it will be clear to one skilled in the art that the offset produced thereby may be simply subtracted once its magnitude is determined by comparison of the measured pressure with a known pressure. However, if the tissue-contact force is not constant, a time-varying pressure waveform artifact will be produced. Such may be the case if changes in the stretch or wall tension of the intra-atrial septum produce changes in tissue-contact force on the diaphragm. In embodiment of the invention, the sensor assembly is designed to decouple intra-atrial stretching or tension from the tissue in contact with the diaphragm. As shown in FIG. 32, in one embodiment a distal rim or ring 301 is provided surrounding the sensor diaphragm 302, such that the stretching is opposed by the ring rather than being forced against the diaphragm 302. The ring 301 serves to isolate the tissue over the diaphragm 302 within it, so that tension within the surrounding tissue is not transmitted to the diaphragm 302. FIGS. 33 to 35 show additional embodiments designed to decouple the diaphragm 302 from surrounding tissue. In FIG. 33 drug delivery is provided on a drug-eluting structure or band 303 about the sensor housing. It will be familiar to those skilled in the art that antiproliferative drugs such as paclitaxel or sirolimus have been used successfully to reduce neointimal proliferation within intravascular stents. In one embodiment of the present invention, a band 303 of drug is provided to limit the ingrowth of tissue over the sensor diaphragm. The skilled artisan will recognize that in some embodiments, a thin neointimal covering is advantageous for reducing the risk of thrombosis. Therefore, in one embodiment, channels 305 free of antiproliferative drug are provided across the drug band 303 to allow for a thin layer of neointima to form over the portion of the sensor that protrudes into the blood within the left atrium.

FIG. 34 shows an embodiment of the present invention comprising circumferential grooves 620 to which ingrowing tissue will adhere, providing mechanical isolation of the diaphragm 302 from the surrounding tissue. FIG. 35 shows another embodiment, where protruding tabs 622 are provided to which ingrowing tissue may adhere, providing mechanical isolation of the diaphragm 302.

Implantation Apparatus and Techniques

Many of the embodiments of implantable devices shown and described herein are preferably configured to be deployed via a tubular, flexible delivery catheter that can be guided either alone or over a guidewire to a delivery location within a patient. A delivery catheter for use in delivering and deploying an implantable device preferably comprises an internal diameter that is at least as large as the outer diameter of the distal and proximal anchors in their compressed states. In some embodiments, a delivery catheter can be configured to be sufficiently large in diameter to allow the catheter to be filled with a continuous cylindrical column of fluid surrounding the sensor module and its lead. This advantageously allows for simultaneous monitoring of a fluid pressure at the distal end of the catheter through the continuous fluid column surrounding the anchoring system in the catheter. Such an arrangement would also advantageously allow for the injection of a radiographic contrast medium through the delivery catheter in order to determine the precise location of the catheter tip in the cardiovascular system. The proximal portion of the catheter may contain a hemostatic adaptor to prevent back bleeding through the catheter around the pressure transducer system and to prevent the entrainment of air during transducer insertion and advancement. The skilled artisan will recognize that other embodiments of delivery catheters incorporating additional fluid-carrying lumens can also be used to deliver an implantable anchoring device. FIGS. 15-21 illustrate several embodiments of systems and methods for delivering and deploying the anchor assembly 100 to secure a sensor 120 in a septum wall 210. According to one embodiment, a traditional transseptal catheterization is performed using the Brockenbrough needle/catheter system. Thereafter a guidewire is placed through the septum wall 210 at the target site. A dilator/hemostatic delivery catheter combination can then be fed over the guidewire and into the left atrium. The guidewire and dilator can then be removed, and the distal tip of the hemostatic delivery catheter crosses the septum and remains in the left atrium. Positioning can be determined under fluoroscopy by contrast injection and pressure measurement thought side arm port the delivery catheter.

As shown in FIGS. 15 and 16, an assembly 100 of a proximal anchor 112, a distal anchor 110 and a sensor 120 is provided within an introducer sheath configured to introduce the anchor assembly into the proximal end of the delivery catheter 220. In one embodiment, the introducer sheath is made of transparent tubing, such as acrylic, advantageously allowing the operator to verify that all air bubbles have been flushed from the introducer sheath before it is inserted through the hemostatic adaptor of the delivery catheter. A stylet 224 is advanced through a central lumen of the electrical lead 226 to provide column strength and guidance to the device.

The introducer sheath containing the anchor and sensor assembly is then inserted into the proximal end of the delivery catheter, and the introducer sheath is retracted and withdrawn. The anchor assembly is then guided through the delivery catheter 220 (which was previously positioned through the septum wall) until the legs of the distal anchor 110 are positioned at the distal end of the delivery catheter 220, which can be visually verified under fluoroscopy by noting the alignment of the distal radiopaque marker 225 on the distal edge of the delivery catheter 220 with the distal end of the sensor assembly 100. The delivery catheter 220 can be withdrawn while holding the anchor and sensor assembly 100 in place with the stylet 224 that extends through the center of the sensor lead 226. The stylet 224 is preferably configured to provide sufficient column strength to allow the anchor and sensor assembly 100 to be held in place relative to the septum 210 while the catheter 220 is retracted to expose and deploy the distal anchor legs 124, as shown in FIG. 17. Alternatively, the catheter 220 can be held in place and the stylet 224 and sensor assembly 100 can be advanced to deploy the distal anchor legs 124.

Figure 18:
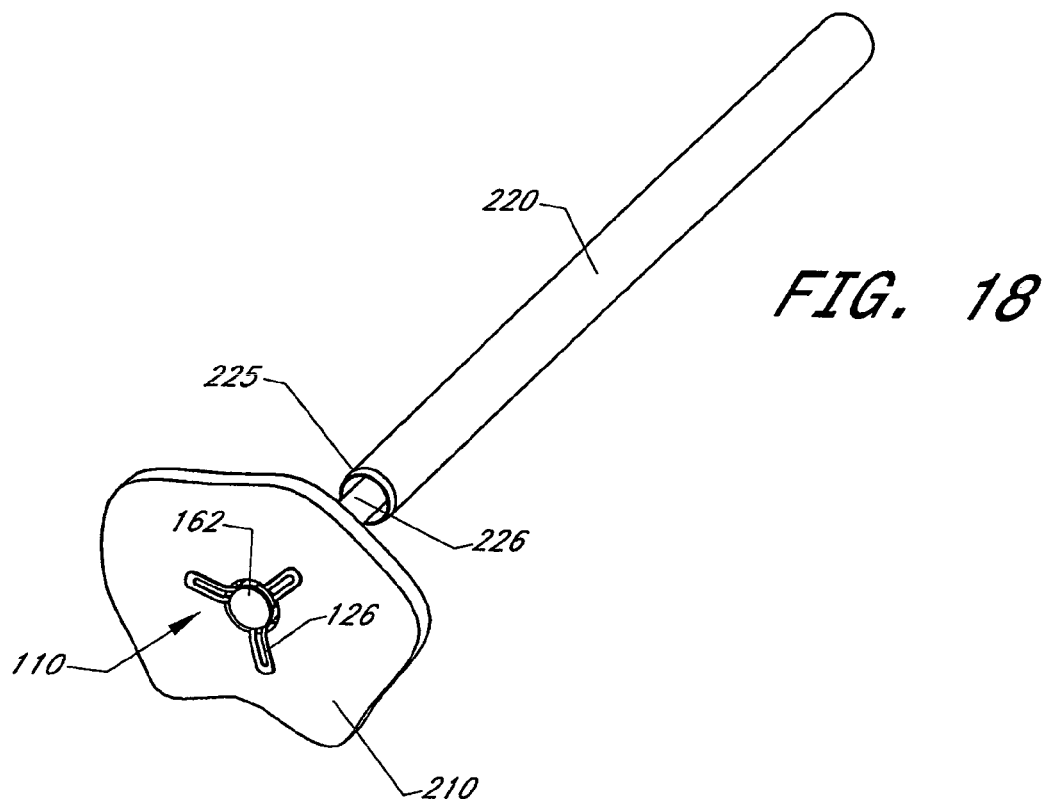
FIG. 18 is a perspective view of the distal anchor and sensor of FIG. 17 with the delivery catheter further retracted.
Figure 19:
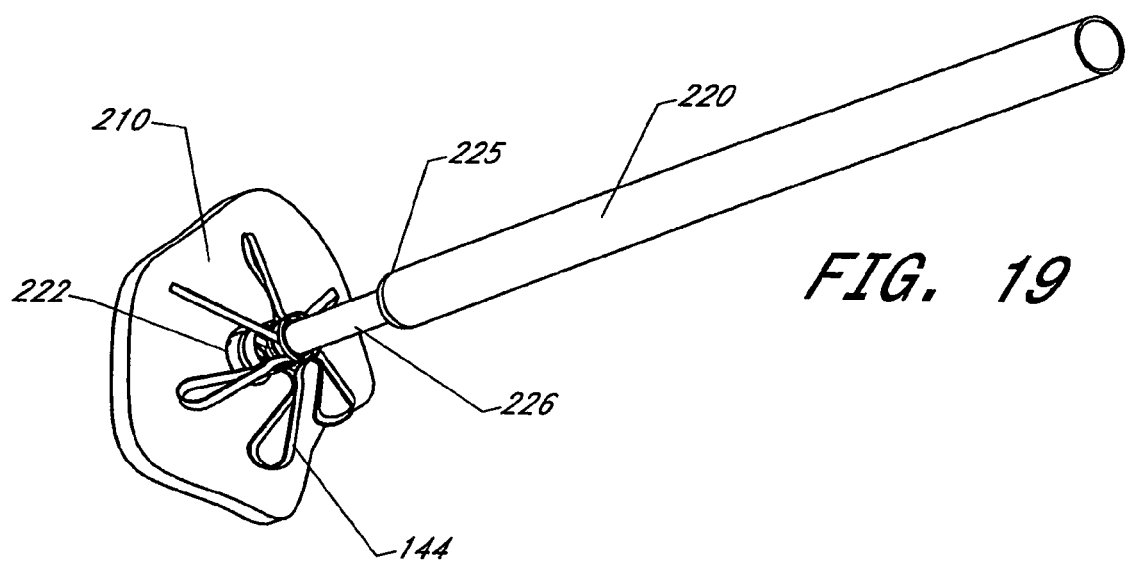
FIG. 19 is a perspective view illustrating a delivery catheter deploying an anchor and sensor assembly as viewed from a proximal side of an atrial septum wall.

In one embodiment, after the distal anchor legs 124 expand to assume their expanded state on a distal side of the septum wall 210, contrast material is injected to assure correct positioning in the left atrium. The catheter 220 is further retracted while holding the stylet 224 and sensor assembly 100 in place until the distal edge of the catheter 220 is coincident with the proximal end of the sensor assemble 100. Further contrast is injected while the entire catheter 220, stylet 224 and sensor assembly 100 are retracted in 1 to 2 mm increments until contrast material exiting the tip of the catheter 220 is observed on fluoroscopy to exit into the right atrium. At this point further retraction of the catheter 220 will expose the proximal anchor 112, allowing it to relax to its expanded state on a proximal side of the septum wall 210 as shown in FIGS. 18 and 19. The fully deployed proximal 112 and distal 110 anchors preferably resiliently engage the septum wall 210 in order to firmly secure the sensor 120 to the septum wall 210.

In one embodiment, to facilitate tissue overgrowth, the path lengths for tissue to in-grow over the distal anchor fixated to the left atrial side of the septum is minimized by creating one or more perforations, holes, pores, or slots in the distal anchor legs 124. For example, FIGS. 1, 2 and 7 show slots 126 in the legs 124 of the distal anchor 110. In one embodiment, surface grooves or channels are used in at least a portion of the device to facilitate tissue growth. In another embodiment, shown in FIG. 26, at least one groove is placed on the diaphragm surface or on the anchor legs to serve a similar purpose. The groove's long axes can be linear, circumferential, and serpentine or any other beneficial shape and the groove's cross section can be rectangular, semi-round, or any other beneficial shape.

Exemplary modes of operation for one embodiment of the invention are described as follows. The following Example illustrates various embodiments of the present invention and is not intended in any way to limit the invention.

EXAMPLE 1

In Vivo Studies

Several of the discoveries in this patent application results from the inventor's first hand experience percutaneously implanting transmural pressure transducer and anchor systems with catheter delivery systems similar to those depicted in FIGS. 1 through 21, in the left atrium of 3 anesthetized pigs. In these experiments, a transseptal catheterization was performed from the right internal jugular vein placing the distal tip of an 11 French×25 cm long, peel-away, hemostatic valve, side-arm delivery catheter in the left atrium under fluoroscopic guidance (Pressure Products). The pressure transducer systems were delivered to the desired location traversing the septum each time. Pigs were observed with transducer system in situ for 0 days, 3 weeks, and 18 weeks and periodic ambulatory pressure readings were obtained using a radiofrequency telemetry system coupled to a palm type computer. The pigs survived for 3 and 18 weeks were returned to the catheterization laboratory at the time of euthanasia for repeat catheterization with a fluid filled catheter to validate pressure readings from the implants. After euthanasia, the hearts were opened and photographs of the gross specimens obtains. The hearts with the pressure transducer and anchoring system in place were fixed in formalin for more 72 hours. These specimens with transducers in situ were placed in a controlled pressure chamber and calibration functions obtained. After calibration, microscopic sections stained with hematoxylin and eosin, and trichrome stains were reviewed by an expert cardiovascular pathologist After opening the left atrial free wall in the pig sacrificed immediately after implantation it was observed that the diaphragm was coplanar, protruding less than 0.5 mm from the surrounding left atrial surface. The distal anchor was flat against the left side of the septum and the proximal anchor was contacting the right side of the septum. Perturbation of the system along any axis was counterbalanced such that when the perturbation force was relieved, the transducer/anchor system restored itself to the original coplanar position.

Figure 25:
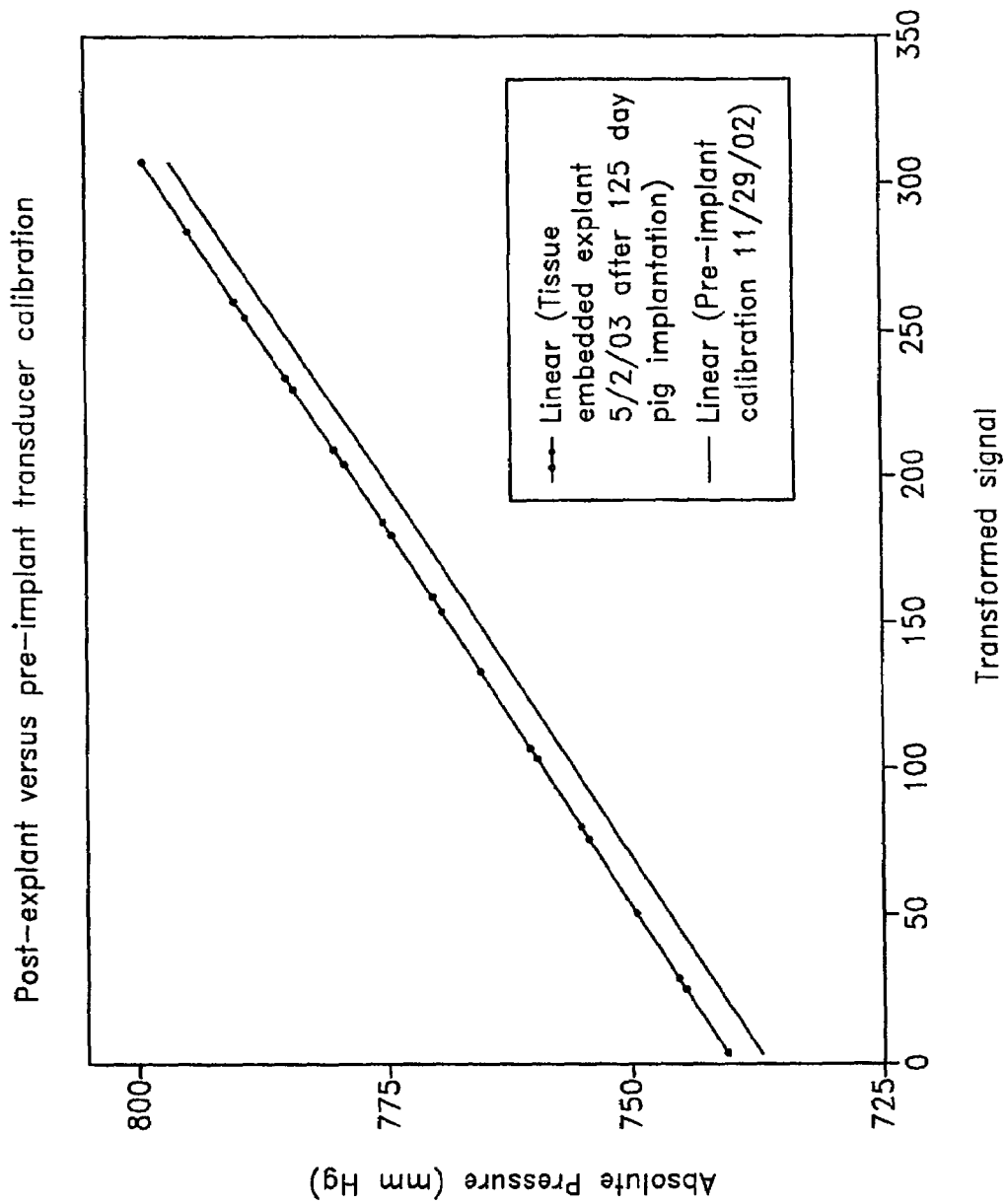
FIG. 25 is a graph comparing transducer calibration functions 1 month before deployment and 18 weeks following deployment in a pig.

For the pig euthanized 3 weeks after transducer deployment, the diaphragm and all 3 legs of the distal anchor were again ideally oriented coplanar with the left atrial wall. It was noted that the location of transmural puncture was somewhat posterior of the thinnest portion and probably made from a non-orthogonal approach. Nevertheless, the device was orthogonally oriented related to its internal restorative force configuration. On the left atrial side of the septum, the transducer diaphragm and the distal anchor legs were entirely covered with a thin, translucent layer of neoendocardium. Histologic sections reveal that the covering tissue was comprised of normal granulation tissue, morphologic smooth muscle cells and fibrocytes without a chronic inflammatory reaction. We obtained ambulatory recordings of the left atrial pressure repeatedly during the 3 week survival. After sacrifice, with the transducer in situ covered with tissue, repeat calibration showed that in comparison to the pre-implantation calibration, there was no change in gain and small change in offset of less than about 2 mm Hg For the pig euthanized 18 weeks after transducer deployment it was noted again that the location of transmural puncture was somewhat posterior of the thinnest portion and probably made from a non-orthogonal approach. Once again, the device was correctly oriented related to its internal restorative force configuration. On the left atrial side of the septum, the transducer diaphragm and the distal anchor legs were now entirely covered with a much thicker, opaque layer of neoendocardium. Histologic sections reveal that the covering tissue was comprised of fibrous tissue staining positively for collagen and there was no inflammatory reaction. We obtained ambulatory recordings of the left atrial pressure repeatedly during the 18 week survival. As shown in FIG. 25, after euthanasia, with the transducer in situ covered with tissue, repeat calibration showed that in comparison to the pre-implantation calibration, there was a 0.5% reduction in gain and a clinically insignificant change in offset of less than about 3 mm Hg The apparatus and methods of several embodiments of the present invention may be embodied in other specific forms and for other applications without departing from its spirit or essential characteristics. The described embodiments are to be considered in all respects only as illustrative and not restrictive.

Although certain embodiments and examples have been described herein, it will be understood by those skilled in the art that many aspects of the methods and devices shown and described in the present disclosure may be differently combined and/or modified to form still further embodiments. Additionally, it will be recognized that the methods described herein may be practiced using any device suitable for performing the recited steps. Such alternative embodiments and/or uses of the methods and devices described above and obvious modifications and equivalents thereof are intended to be within the scope of the present disclosure. Thus, it is intended that the scope of the present invention should not be limited by the particular embodiments described above, but should be determined only by a fair reading of the claims that follow.

Additionally, the skilled artisan will recognize that the embodiments of anchoring devices and methods described herein may be advantageously applied for implanted pressure transducers transmurally positioned on, in or through a wall of any organ or vessel within a patient. It will also be apparent to one skilled in the art that the field of use of the embodiments of devices and methods described herein extends beyond the specific condition of heart failure to any cardiovascular condition or other condition in a medical patient where a device is implanted through a wall of a chamber or vessel or is affixed to a wall of that chamber of vessel.

What is claimed is:

1. A physiological lead system, comprising:
   an elongate member having a proximal end and a distal end;

a lead located generally at the distal end of said elongate member; and a distal anchor assembly engaged to said elongate member, said distal anchor assembly comprising at least one protruding member, said distal anchor assembly configured to change shape from a first state to a second state, wherein the at least one protruding member is substantially parallel to a longitudinal axis of the distal anchor assembly in the first state and bent at an angle with respect to the longitudinal axis of the distal anchor assembly in the second state, and wherein the at least one protruding member further comprises at least one non-linear tissue ingrowth path.

2. The physiological lead system of claim 1, wherein at least one said non-linear tissue ingrowth path comprises a hole in said protruding member.

3. The physiological lead system of claim 2, wherein said protruding member comprises a plurality of holes of similar diameters.

4. The physiological lead system of claim 2, wherein said protruding member comprises a plurality of holes of different diameters.

5. The physiological lead system of claim 1, wherein at least one said non-linear tissue ingrowth path comprises a curved slit or variable width slit.

6. The physiological lead system of claim 1, wherein at least one said tissue ingrowth path comprises a groove.

7. The physiological lead system of claim 1, wherein at least one said protruding member has a curved or angled configuration.

8. The physiological lead system of claim 7, wherein the curved or angled configuration of said protruding member is curved or angled radially about a longitudinal axis of said elongate member.

9. The physiological lead system of claim 7, wherein the curved or angled configuration of said protruding member lies in the same plane as a perpendicular radial cross section of said elongate member.

10. The physiological lead system of claim 1, wherein said distal anchor assembly is engaged to said elongate member at a separation distance from said lead such that said lead is substantially unaffected by forces acting on said distal anchor assembly.

11. The physiological lead system of claim 1, further comprising a proximal anchor assembly engaged to said elongate member generally between said distal anchor assembly and the proximal end of said elongate member.

12. The physiological lead system of claim 1, wherein at least a portion of said distal anchor assembly has a biocompatible coating.

13. The physiological lead system of claim 12, wherein at least a portion of one said tissue ingrowth path has a biocompatible coating.

14. The physiological lead system of claim 12, wherein said biocompatible coating is bio-stable.

15. The physiological lead system of claim 12, wherein said biocompatible coating is bio-erodable.

16. The physiological lead system of claim 12, wherein said biocompatible coating is resistant to thrombus formation.

17. The physiological lead system of claim 12, wherein said biocompatible coating is configured to control tissue ingrowth.

18. The physiological lead system of claim 12, wherein said biocompatible coating is resistant to corrosion.

19. The physiological lead system of claim 12, wherein said biocompatible coating is configured to reduce formation of fibrous tissue.

20. The physiological lead system of claim 19, wherein said biocompatible coating does not prevent growth of endothelial tissue.

21. The physiological lead system of claim 1, further comprising a drug-eluting system.

22. The physiological lead system of claim 21, wherein said drug-eluting system comprises a coating on said distal anchor assembly.

23. The physiological lead system of claim 22, wherein the drug-eluting coating is configured for a particular elution rate or elution duration.

24. The physiological lead system of claim 22, wherein said drug-eluting system further comprises a drug for controlling neointimal thickness.

25. The physiological lead system of claim 1, wherein said elongate member further comprises a removable stylet and a stylet lumen.

26. The physiological lead system of claim 1, wherein at least one ingrowth path is non-linear when the distal anchor assembly is in the second state.

27. The physiological lead system of claim 1, wherein the at least one protruding member comprises a substantially planar tissue-contacting surface.

28. The physiological lead system of claim 1, wherein the at least one protruding member comprises a tissue-contacting surface configured to contact a tissue surface at an implant site without puncturing the tissue surface.

29. A physiological lead system, comprising:
an elongate member having a proximal end and a distal end;
a lead located generally at the distal end of said elongate member; and
means for anchoring said lead system to an organ wall in a body, wherein said means for anchoring is configured to change shape from a first state to a second state, and wherein the means for anchoring comprises at least one non-linear tissue ingrowth path.

30. A physiological sensor system, comprising:
an elongate member having a proximal end and a distal end;
a sensor located generally at the distal end of said elongate member; and
a distal anchor assembly engaged to said elongate member, said distal anchor assembly comprising at least one protruding member, said distal anchor assembly configured to change shape from a first state to an second state,
wherein the at least one protruding member is substantially parallel to a longitudinal axis of the distal anchor assembly in the first state and bent at an angle with respect to the longitudinal axis of the distal anchor assembly in the second state, and
wherein the at least one protruding member further comprises at least one non-linear tissue ingrowth path.

* * * * *